US012589262B2

(12) United States Patent
Puleo et al.

(10) Patent No.: US 12,589,262 B2
(45) Date of Patent: Mar. 31, 2026

(54) NEUROMODULATION TECHNIQUES

(71) Applicant: GE PRECISION HEALTHCARE LLC, Waukesha, WI (US)

(72) Inventors: Christopher Michael Puleo, Niskayuna, NY (US); Victoria Eugenia Cotero, Troy, NY (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 18/612,667

(22) Filed: Mar. 21, 2024

(65) Prior Publication Data

US 2024/0226609 A1 Jul. 11, 2024

Related U.S. Application Data

(63) Continuation of application No. 16/978,987, filed as application No. PCT/US2019/021018 on Mar. 6, 2019, now Pat. No. 11,938,348.

(Continued)

(51) Int. Cl.
| | |
|---|---|
| *A61N 7/00* | (2006.01) |
| *A61B 5/00* | (2006.01) |
| *A61B 5/145* | (2006.01) |

(52) U.S. Cl.
CPC ............ *A61N 7/00* (2013.01); *A61B 5/14532* (2013.01); *A61B 5/4836* (2013.01);
(Continued)

(58) Field of Classification Search
CPC .... A61N 7/00; A61N 7/02; A61N 2007/0026; A61N 2007/0052; A61N 2007/0073; A61N 2007/0078; A61N 2007/0095; A61N 1/36121; A61N 1/36132; A61N 1/36007; A61N 1/05; A61N 1/36139; A61B 5/14532; A61B 5/4836
See application file for complete search history.

(56) References Cited

U.S. PATENT DOCUMENTS

| | | | |
|---|---|---|---|
| 8,591,419 B2 | 11/2013 | Tyler | |
| 8,903,501 B2 * | 12/2014 | Perryman | A61N 1/36057 607/62 |

(Continued)

FOREIGN PATENT DOCUMENTS

| | | |
|---|---|---|
| CN | 104254366 A | 12/2014 |
| WO | 2015069446 A1 | 5/2015 |
| WO | 2016090175 A1 | 6/2016 |

OTHER PUBLICATIONS

Thorens, B. "Brain glucose sensing and neural regulation of insulin and glucagon secretion." Diabetes, Obesity and Metabolism 13 (2011): 82-88. (Year: 2011).*

(Continued)

*Primary Examiner* — Sean D Mattson
(74) *Attorney, Agent, or Firm* — Fletcher Yoder, P.C.

(57) ABSTRACT

The subject matter of the present disclosure generally relates to techniques for neuromodulation of a tissue (e.g., an organ) that include applying energy (e.g., ultrasound energy) into the tissue to cause altered activity at a synapse between a neuron and a non-neuronal cell. In one embodiment, the energy is applied to cause competing or opposing effects for bi-directional control of physiological processes.

14 Claims, 41 Drawing Sheets

Related U.S. Application Data

(60) Provisional application No. 62/641,050, filed on Mar. 9, 2018.

(52) U.S. Cl.
CPC .................. *A61N 2007/0026* (2013.01); *A61N 2007/0052* (2013.01); *A61N 2007/0073* (2013.01); *A61N 2007/0078* (2013.01)

(56) References Cited

U.S. PATENT DOCUMENTS

| | | | | |
|---|---|---|---|---|
| 10,974,079 | B2 * | 4/2021 | Puleo ....................... | A61N 7/00 |
| 11,167,154 | B2 | 11/2021 | Alford et al. | |
| 11,938,348 | B2 * | 3/2024 | Puleo ................... | A61B 5/4836 |
| 2004/0236375 | A1 | 11/2004 | Redding | |
| 2004/0249421 | A1 | 12/2004 | Harel et al. | |
| 2009/0131993 | A1 * | 5/2009 | Rousso .............. | A61N 1/36017 |
| | | | | 607/2 |
| 2009/0234417 | A1 | 9/2009 | Pastena et al. | |
| 2011/0178441 | A1 * | 7/2011 | Tyler ....................... | A61N 5/062 |
| | | | | 601/2 |
| 2013/0144165 | A1 * | 6/2013 | Ebbini ................ | G01S 7/52046 |
| | | | | 600/439 |
| 2013/0178910 | A1 * | 7/2013 | Azamian .............. | A61K 9/0019 |
| | | | | 607/33 |
| 2014/0058292 | A1 * | 2/2014 | Alford ................. | A61B 5/0036 |
| | | | | 601/2 |
| 2018/0028841 | A1 | 2/2018 | Konofagou et al. | |
| 2018/0207450 | A1 * | 7/2018 | Sanchez ................... | A61N 7/00 |

OTHER PUBLICATIONS

Berthoud, Hans-Rudolf. "Anatomy and function of sensory hepatic nerves." The Anatomical Record Part A: Discoveries in Molecular, Cellular, and Evolutionary Biology: An Official Publication of the American Association of Anatomists 280.1 (2004): 827-835. (Year: 2004).*

Tavakkolizadeh, Ali, et al. "Differential Role of Vagus Nerve in Maintaining Diurnal Gene Expression Rhythms in the Proximal Small Intestine 1." Journal of Surgical Research 129.1 (2005): 73-78. (Year: 2005).

Cotero, Victoria E. et al., "Insulin blunts the response of glucose-excited neurons in the ventrolateral-ventromedial hypothalamic nucleus to decreased glucose", American Journal of Physiology-Endocrinology and Metabolism, vol. 296, Issue: 5, pp. E1101-E1109, 2009.

Cotero, V.E., et al.; "The Response of Glucose-Excited Neurones in the Ventromedial Hypothalamus to Decreased Glucose is Enhanced in a Murine Model of Type 2 Diabetes Mellitus", Journal of Neuroendocrinology, vol. 22, Issue 2, pp. 65-74, Feb. 2010.

Juan, Eduardo J., et al.; "Vagus Nerve Modulation Using Focused Pulsed Ultrasound: Potential Applications and Preliminary Observations in a Rat", Int J Imaging Syst Technol, vol. 24, Issue: 1, pp. 67-71, Mar. 2014.

Thorens, B. "Neural regulation of pancreatic islet cell mass and function." Diabetes, Obesity and Metabolism 16.S1 (2014): 87-95. (Year: 2014).

Frangos, Eleni, et al.; "Non-invasive Access to the Vagus Nerve Central Projections via Electrical Stimulation of the External Ear: fMRI Evidence in Humans", Brain Stimul, vol. 8, Issue: 3, pp. 624-636, 2015.

Castellanos, Ivan Suarez, et al.; "Ultrasound stimulation of insulin release from pancreatic beta cells", VII Latin American Congress on Biomedical Engineering CLAIB 2016, pp. 62-65, vol. 60, Columbia, Oct. 26-28, 2016.

Downs, Matthew E. et al., "Non-invasive peripheral nerve stimulation via focused ultrasound in vivo", Phys Med Biol, vol. 63, Issue: 3, Jan. 26, 2018.

\* cited by examiner

50

| Spatially select region of interest of a target tissue | 52 |

| Focus energy application device on region of interest of the target tissue | 54 |

| Cause energy application device to apply one or more energy pulses to the region of interest | 56 |

| Preferentially activate synapses as a result of the energy pulses to cause targeted physiological outcome | 58 |

12

74

Pulse length

T

NEUROMODULATION TECHNIQUES

CROSS-REFERENCE TO RELATED APPLICATIONS

This application is a Continuation Application of U.S. application Ser. No. 16/978,987, entitled "NEUROMODULATION TECHNIQUES" and filed Sep. 8, 2020, which claims priority to and is a national stage filing of International Application No. PCT/US2019/021018, filed on Mar. 6, 2019, which claims priority to and the benefit of U.S. Provisional Application No. 62/641,050, entitled "NEUROMODULATION TECHNIQUES" and filed Mar. 9, 2018, the disclosures of which are incorporated herein by reference for all purposes.

BACKGROUND

The subject matter disclosed herein relates to neuromodulation and more specifically, to techniques for modulating a physiological response using energy applied from an energy source.

Neuromodulation has been used to treat a variety of clinical conditions. For example, electrical stimulation at various locations along the spinal cord has been used to treat chronic back pain. Such treatment may be performed by an implantable device that periodically generates electrical energy that is applied to a tissue to activate certain nerve fibers, which in turn may result in a decreased sensation of pain. In the case of spinal cord stimulation, the stimulating electrodes are generally positioned in the epidural space, although the pulse generator may be positioned somewhat remotely from the electrodes, e.g., in the abdominal or gluteal region, but connected to the electrodes via conducting wires. In other implementations, deep brain stimulation may be used to stimulate particular areas of the brain to treat movement disorders, and the stimulation locations may be guided by neuroimaging. Such central nervous system stimulation is generally targeted to the local nerve or brain cell function and is mediated by electrodes that deliver electrical pulses and that are positioned at or near the target nerves. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more targeted modulated effect may be more clinically useful.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a modulation system is provided. The system includes at least one energy application device; and a controller configured to focus the at least one energy application device on a first region of interest of a first tissue, the first tissue comprising a first plurality of axon terminals of respective neurons, one or more of the plurality of axon terminals forming synapses between individual axon terminals and respective non-neuronal cells, wherein the first region of interest comprises a first subset of the first plurality of axon terminals; adjustably control the at least one energy application device to apply a first energy to the first region of interest to selectively modulate a first molecule of interest; focus the at least one energy application device on a second region of interest, wherein the second region of interest comprises a second subset of axon terminals; and adjustably control the at least one energy application device to apply a second energy to the second region of interest to selectively modulate the first molecule of interest or a second molecule of interest.

In another embodiment, a modulation system is provided that includes at least one energy application device configured to apply energy to a first region of interest of a first tissue in a subject, the first tissue comprising a plurality of axon terminals of respective neurons, the axon terminals forming synapses between individual axon terminals and respective non-neuronal cells and to a second region of interest of a second tissue in the subject. The system also includes a controller configured to spatially select the first region of interest of the first tissue and the second region of interest in the second tissue; focus the energy on the first region of interest and the second region of interest; and adjustably control application of the energy via the at least one energy application device to the first region of interest to induce preferential activation of a subset of the synapses, the subset being located in the first region of interest, to cause a first molecule concentration of a first molecule to change and control application of the energy via the at least one energy application device to the second region of interest to cause a second molecule concentration of a second molecule to change.

In another embodiment, a modulation system is provided that includes an energy application device configured to apply energy to a region of interest of a pancreas in a subject, the region of interest being a subregion of the pancreas comprising synapses between neuronal cells and respective non-neuronal cells. The system also includes a controller configured to spatially select the region of interest of the pancreas; focus the energy on the region of interest; and adjustably control application of the energy via the energy application device to the region of interest of the pancreas to induce preferential activation at the synapses between neuronal cells and non-neuronal cells in the region of interest to selectively modulate or cause a change in concentration of one or more molecules of interest.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
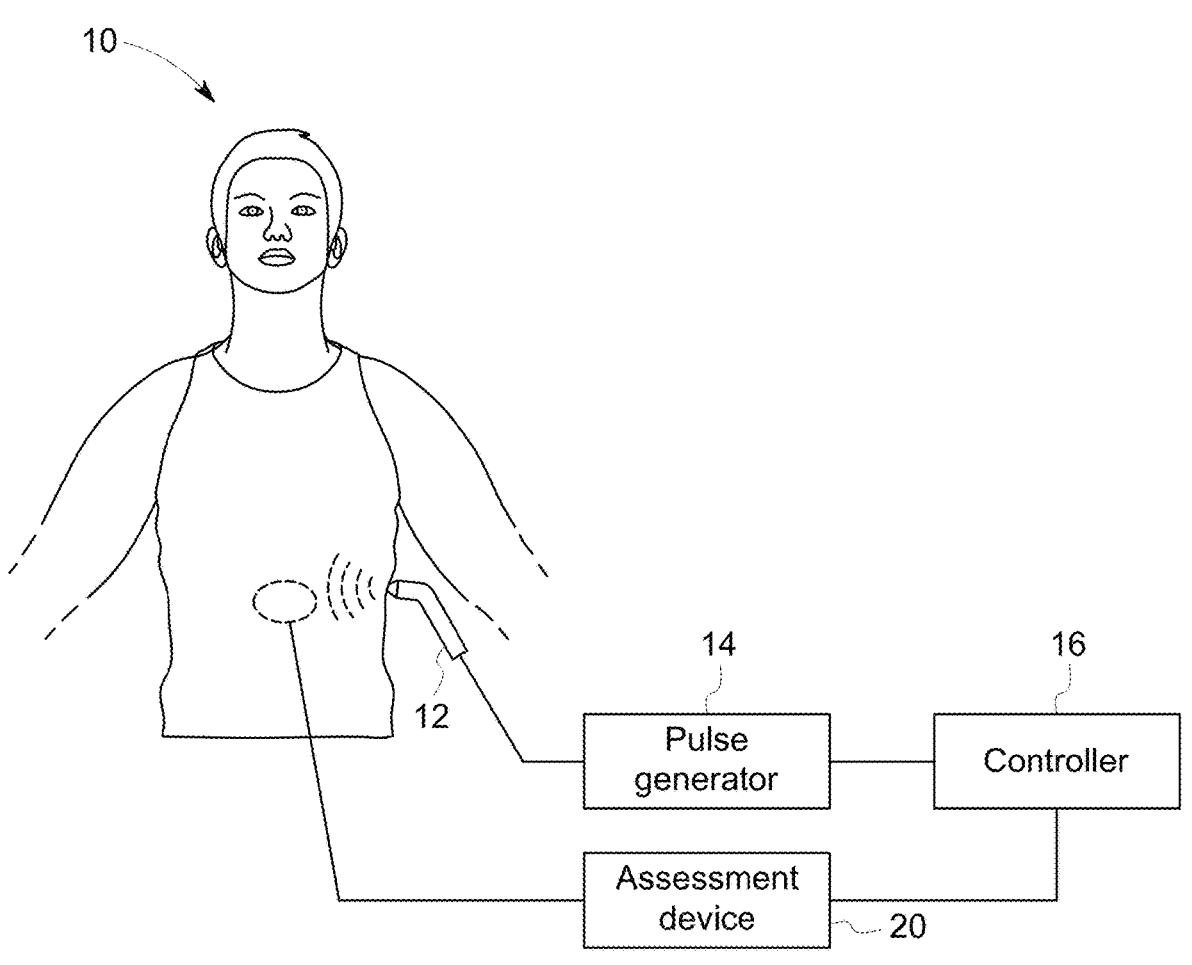
FIG. 1 is a schematic representation of a neuromodulation system using a pulse generator according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments", "in some embodiments", and "in one (an) embodiment."

Provided herein are techniques for neuromodulation based on direct and focused modulation of targeted regions of interest and to cause targeted physiological outcomes that are the result of the modulation. The targeted region or regions of interest may be any tissue or structure in the body having axon terminals forming synapses with non-neuronal cells or fluids. In one example, the region of interest may be in an organ or structure, such as a spleen, liver, pancreas, or gastrointestinal tissue. In another example, the regions of interest may be in a lymph system tissue. Neuromodulation of regions of interest permits a local, limited, and nonablative application of energy to only the targeted regions of interest and without the energy being applied outside of the regions of interest. Energy application may trigger downstream effects outside of the targeted regions of interest, e.g., in the same organ, tissue or structure containing the region of interest or in other organs and structures that do not contain the targeted region of interest. In some embodiments, the downstream effects may be induced in areas of a hypothalamus by way of example. The energy application may also induce effects along the targeted nerve upstream from the site of the energy application. In some embodiments, the effects outside of the targeted region/s of interest may be achieved without direct energy application to areas outside of the region/s of interest where the downstream effects or upstream effects are induced. Accordingly, local energy application may be used to realize or achieve systemic effects which may include local effects, downstream effects and/or upstream effects.

Further, the present techniques relate to bi-directional control of complex physiological processes. For example, to avoid excess activation of one pathway and excess change of physiological outcomes as a result of energy application at a particular region of interest, energy may be applied to a different region of interest that is associated with a competing pathway or a deactivation pathway to induce change of physiological outcomes in an opposite direction and to maintain a dynamic equilibrium of the physiological outcomes for achieving desired physiological outcomes. In a specific example, to achieve a desired circulating glucose concentration or concentration range in a hyperglycemic subject, energy may be applied to a region of interest that causes a decrease in a circulating glucose concentration. However, to avoid overcorrection of glucose and resulting hypoglycemia, energy may also be applied to a second region of interest that causes an increase in the circulating glucose concentration to maintain a dynamic equilibrium of the circulating glucose concentration and stabilize the circulating glucose concentration to a desired level. For example, if direct energy application to the liver causes a decrease in glucose beyond a clinically acceptable level, then energy may also be applied to the pancreas to increase glucagon production to compensate. Bi-directional stimulation may be implemented as provided herein to a first region of interest in a first organ and a second region of interest in a second organ. In another embodiment, multi-site neuromodulation may be neuromodulation performed on different sites that enhance same pathways. The energy application to the first region of interest and the second region of interest may be simultaneous or at different times (e.g., separated by seconds, minutes, day, or hours) and may be performed by the same or different energy application device.

The disclosed techniques may be used to exert external control on physiological processes of the body to cause targeted physiological outcomes in subjects. Via neuromodulation to the targeted regions of interest, physiological processes may be altered, slowed, halted, or reversed. Also provided herein are techniques that may be applied to subjects to promote dynamic equilibrium or homeostasis of physiological processes, such as glucose regulation. The targeted neuromodulation may function in opposition to ongoing pathogenesis or disease progression to provide treatment and to improve outcomes relative to control (i.e., relative to untreated subjects). In some embodiments, the targeted neuromodulation may be preventative and may be initiated prior to certain events. For example, targeted neuromodulation may be used to prevent appetite loss associated with certain medical treatments or conditions or may be applied before or during meals to alter the body's response to the meal.

Neuromodulation to the targeted regions of interest may exert a change in physiological processes to interrupt, decrease, or augment one or more physiological pathways in a subject to yield the desired physiological outcome. Further, because the local energy application may result in systemic changes, different physiological pathways may be changed in different ways and at different locations in the body to cause an overall characteristic profile of physiological change in the subject caused by and characteristic of the targeted neuromodulation for a particular subject. While these changes are complex, the present neuromodulation techniques provide one or more measurable targeted physiological outcomes that, for the treated subjects, are the result of the neuromodulation and that may not be achievable without the application of energy to the targeted region/s of interest or other intervention. Further, while other types of intervention (e.g., drug treatment) may yield a subset of the physiological changes caused by neuromodulation, in certain embodiments, the profile of the induced physiological changes as a result of the neuromodulation may be unique to the neuromodulation (and its associated modulation parameters) at the targeted region/s of interest and may differ from patient to patient.

The neuromodulation techniques discussed herein may be used to cause a physiological outcome of a change in concentration (e.g., increased, decreased) of a molecule of interest and/or a change in characteristics of a molecule of interest. That is, selective modulation of one or more molecules of interest (e.g., a first molecule of interest, a second molecule of interest, and so on) may refer to modulating or influencing a concentration (circulating, tissue) or characteristics (covalent modification) of a molecule as a result of energy application to one or more regions of interest (e.g., a first region of interest, a second region of interest, and so on) in one or more tissues (e.g., a first tissue, a second tissue, and so on). Modulation of a molecule of interest may include changes in characteristics of the molecule such as expression, secretion, translocation of proteins and direct activity changes based on ion channel effects either derived from the energy application itself or as a result of molecules directly effecting ion channels. Modulation of a molecule of interest may also refer to maintaining a desired concentration of the molecule, such that expected changes or fluctuations in concentration do not occur as a result of the neuromodulation. Modulation of a molecule of interest may refer to causing changes in molecule characteristics, such as enzyme-mediated covalent modification (changes in phosphorylation, aceylation, ribosylation, etc.). That is, it should be understood that selective modulation of a molecule of interest may refer to molecule concentration and/or molecule characteristics. The molecule of interest may be a biological molecule, such as one or more of carbohydrates (monosaccharaides, polysaccharides), lipids, nucleic acids (DNA, RNA), or proteins. In certain embodiments, the molecule of interest may be a signaling molecule such as a hormone (an amine hormone, a peptide hormone, or a steroid hormone).

Certain embodiments described herein provide neuromodulation techniques that cause targeted physiological outcomes for the treatment of glucose metabolism and associated disorders. Glucose regulation is complex and involves different local and systemic metabolic pathways. Application of energy to targeted region/s of interest causes characteristic changes in these metabolic pathways to improve glucose regulation. In some embodiments, modulation at one or more regions of interest may be used to treat disorders including but not limited to, diabetes (i.e., type 1 or type 2 diabetes), hyperglycemia, sepsis, trauma, infection, physiologic stress, diabetes-associated dementia, obesity, or other eating or metabolic disorders. In some embodiments, neuromodulation may be used to promote weight loss, control appetite, treat cachexia, or increase appetite. In one example, physiologic stress may be medically defined to include a variety of acute medical conditions (infection, severe injury/trauma, heart attack, bypass) as well as surgical instances with presentation of hyperglycemia. For example, direct pancreatic stimulation may result in increased appetite, while direct liver stimulation may cause a decrease in NPY, which in turn promotes signals of satiety. The targeted physiological outcome may include tuning circulating (i.e., blood) glucose concentrations in a subject to be within a desired concentration range associated with normal glucose levels and avoiding hyperglycemia or hypoglycemia. In this manner, selective modulation of a molecule of interest may be achieved. The tuning may be a result of induced changes in glucoregulatory hormones in the blood or tissue via targeted neuromodulation to cause the desired glucose concentration (i.e. desired glucose end point). Further, glucose regulation may be beneficial for healthy patients without a disease diagnosis, but who are pre-diabetic or who are hoping to maintain a healthy weight.

A benefit of the targeted neuromodulation as provided herein is flexibility of adjustable or tunable treatment level (i.e., modulation parameters may be adjusted), for example, location, application frequency, and duration of the energy application may be adjusted to facilitate tuning of the targeted physiological outcome in response to physiological condition changes in the subject. For example, food intake causes changes in endocrine hormone levels. The targeted neuromodulation may be used to induce desired changes in the body's response to food intake, whether the response is healthy or diseased and that may be calibrated to a particular subject's characteristic response to food intake or other physiological conditions. For example, some patients may benefit from a neuromodulation treatment to cause an increase in circulating insulin and a resultant circulating glucose to decrease while other patients may benefit from bi-directional treatment that also induces glucagon increases in the tissue and/or blood to avoid a hypoglycemic endpoint of treatment. That is, it may be desirable to avoid a concentration of circulating glucose post-treatment that is associated with hypoglycemia. Accordingly, the neuromodulation treatment as provided herein may be implemented to be single site or multi-site as appropriate to achieve the desired concentration of circulating glucose. Because glucose concentration varies in response to eating, sleep, and other physiological inputs, the desired glucose concentration may fall within an acceptable range for fasting or postprandial glucose levels as appropriate for the subject.

To that end, the present techniques relate to targeted modulation of synapses at axon terminals in a tissue via a direct application of energy by an energy source to cause a change that results in a measurable physiological outcome (e.g., a change in a circulating molecule concentration or a suite of concentrations changes forming a characteristic physiological profile). The targeted synapses may include axoextracellular synapses formed between presynaptic axon terminals and postsynaptic non-neuronal cells. In addition, while certain disclosed embodiments are discussed in the context of axoextracellular synapses, it should be understood that the axon terminals may form axosecretory, axosynaptic, axosomatic or axoextracellular synapses, and that additionally or alternatively, these synaptic types are contemplated as being selectively modulated, as provided herein. Further, certain axon terminals may terminate in interstitial or body fluid that may also experience neurotransmitter release as a result of the modulation. The disclosed synapses may be modulated to alter an activity in the synapses, e.g., a release of neurotransmitters from the presynaptic axon terminals, as a result of the energy application. Accordingly, the altered activity may lead to local effects and/or non-local (e.g., systemic) effects to cause the overall profile of physiological changes associated with the desired or targeted physiological outcome. The present techniques permit energy to be focused in a targeted manner on a volume of tissue that includes certain axon terminals to preferentially directly activate the targeted axon terminals to achieve desired outcomes. In this manner, the targeted axon terminals within a region of interest are activated while, in certain embodiments, axon terminals in the same organ or tissue structure but that are outside of the region of interest are not activated. Because organs and tissue structures may include different types of axon terminals that form synapses with different types of postsynaptic non-neuronal cells, the region of interest may be selected that includes particular types of axon terminals that, when activated, yield the desired targeted physiological outcome. Accordingly, the modulation may target a specific type of axon terminal on the basis of the presynaptic neuron type, the postsynaptic cell type, or both.

For example, in one embodiment, the type of axon terminal may be an axon terminal forming an axoextracellular synapse with a resident (i.e., tissue-resident or non-circulating) liver, pancreatic, or gastrointestinal tissue cell. That is, the axoextracellular synapse is formed at a junction between an axon terminal and a nonneuronal cell or interstitial or body fluid. Accordingly, the application of energy leads to modulation of function in the region of interest. However, it should be understood that, based on the population of axon terminal types and the characteristics of the presynaptic neuron type and postsynaptic cells (e.g., immune cells, lymph cells, mucosal cells, muscle cells, etc.) of the axoextracellular synapse, different targeted physiological effects may be achieved. Accordingly, applying energy to a region of interest in a tissue of a subject may activate axon terminals and their associated axoextracellular synapse within the region of interest while untargeted axon terminals (and associated synapses) outside of the region of interest may be unaffected. However, because modulation may result in systemic effects, untargeted axon terminals outside of the region of interest may experience certain systemic changes as a result of the activation of the axon terminals within the region of interest. As provided herein, preferential activation or direct activation may refer to the cells or structures (e.g., synapses) that experience direct application of energy (e.g., the energy is applied directly to the cells or structures) and are within a region of interest. For example, axon terminals, axoextracellular synapses, and/or postsynaptic non-neuronal cells or interstitial or body fluid within the region of interest may directly experience the applied energy as provided herein. Preferential or direct activation may be considered in contrast to areas outside of a region of interest that do not experience direct energy application, even if such areas nonetheless undergo physiological changes as a result of the energy application.

The human nervous system is a complex network of nerve cells, or neurons, found centrally in the brain and spinal cord and peripherally in the various nerves of the body. Neurons have a cell body, dendrites and an axon. A nerve is a group of neurons that serve a particular part of the body. Nerves may contain several hundred neurons to several hundred thousand neurons. Nerves often contain both afferent and efferent neurons. Afferent neurons carry signals to the central nervous system and efferent neurons carry signals to the periphery. A group of neuronal cell bodies in one location is known as a ganglion. Electrical signals generated in the nerves (e.g., via stimulation, which may be intrinsic or externally applied) are conducted via neurons and nerves. Neurons release neurotransmitters at synapses (connections) adjacent to a receiving cell to allow continuation and modulation of the electrical signals. In the periphery, synaptic transmission often occurs at ganglia.

The electrical signal of a neuron is known as an action potential. Action potentials are initiated when a voltage potential across the cell membrane exceeds a certain threshold. This action potential is then propagated down the length of the neuron. The action potential of a nerve is complex and represents the sum of action potentials of the individual neurons in it. The junction between the axon terminals of a neuron and the receiving cell is called a synapse. Action potentials travel down the axon of the neurons to its axon terminal, the distal termination of the branches of an axon nerve that forms a presynaptic ending or a synaptic terminal of the nerve fiber. The electrical impulse of the action potential triggers migration of vesicles containing neurotransmitters to a presynaptic membrane of the presynaptic axon terminal and ultimately the release of the neurotransmitters into a synaptic cleft (e.g., the space formed between the presynaptic and the postsynaptic cell) or the axoextracellular space. A synapse that reaches a synaptic terminal to convert the electrical signal of the action potential to a chemical signal of neurotransmitter release is a chemical synapse. Chemical synapses may be contrasted with electrical synapses in which the ionic currents flowing into a presynaptic axon terminal can cross the barrier of the two cell membranes and enter a postsynaptic cell.

The physiological effect of the action potential is mediated by ion movement across a cell membrane. Neurons actively maintain a resting membrane potential via ion pumps that facilitate movement of ions such as $Na^+$, $K^+$, and $Cl^-$ through the neuronal membrane. Different types of neurons may maintain different resting potentials, e.g., $-75$ mV to $-55$ mV. An action potential is generated by an influx of ions, i.e., a movement of charge to generate a large deviation in the membrane potential that is associated with a temporary rise in voltage across the membrane, e.g., a rise to a membrane potential in a range of 30-60 mV. The action potential in an individual neuron may be initiated in response to a neurotransmitter release from a presynaptic (e.g., upstream) neuron, which in turn results in receptor binding at the postsynaptic cell and a cascade of events which leads to an influx of ions and membrane depolarization that results in an action potential that is propagated through the nerve.

Synapses may be located at a junction between two neurons, which permits an action potential to be propagated down a nerve fiber. However, axon terminals may also form synapses at the junctions between neurons and non-neuronal cells or may terminate at interstitial fluid or body fluid. Examples of synapse types are synapses with immune cells at a neuroimmune junction, synapses with resident sensory cells within an organ, or synapses with gland cells. Release of neurotransmitters into a synaptic cleft and binding to receptors in a postsynaptic membrane of a postsynaptic cell results in downstream effects that are dependent on the nature of the presynaptic neuron and the specific neurotransmitters released as well as the nature of the postsynaptic cell, e.g., types of available receptors of the postsynaptic cell. In addition, an action potential may be excitatory or inhibitory. An excitatory postsynaptic action potential is a postsynaptic potential that makes the postsynaptic neuron more likely to fire or release a subsequent action potential while an inhibitory postsynaptic action potential is a postsynaptic potential that makes the postsynaptic neuron less likely to fire or release a subsequent action potential. Further, several neurons may work together to release neurotransmitters in concert that trigger downstream action potentials or inhibit downstream action potentials.

Neuromodulation is a technique in which energy from an external energy source is applied to certain areas of the nervous system to activate or increase the nerve or nerve function and/or block or decrease the nerve or nerve function. In certain neuromodulation techniques, one or more electrodes are applied at or near target nerves, and the application of energy is carried through the nerve (e.g., as an action potential) to cause a physiological response in areas of the downstream of the energy application site. However, because the nervous system is complex, it is difficult to predict the scope and eventual endpoint of the physiological response for a given energy application site.

While strategies for ultrasound modulation of the central nervous system (i.e. brain tissue) have demonstrated desired modulation of neural activity, attempts to modulate peripheral nerves have lagged. For example, ultrasound modulation of the central nervous system (CNS) involves stimulation of cortical regions of the brain, which are rich in synaptic structures while attempts at ultrasound stimulation of peripheral nerves have targeted nerve trunks that are less rich in or devoid of synaptic structures.

In the present technique, modulation of peripheral nerves involves applying energy to target one or more peripheral axon terminals and to in turn impact blood glucose levels and/or to impact glucose regulatory pathways and/or insulin production pathways. In present techniques, one or more energy pulses are applied to the subject's internal tissue comprising axon terminals that include axoextracellular synapses or neuronal junctions with other cell types, interstitial fluid, or body fluid, e.g., at synapses between a neuronal cell and a non-neuronal cell, whereby applying energy to synapse causes direct activation of the presynaptic axon terminals and/or direct activation at the postsynaptic cell to cause a targeted physiological outcome. In one example, stimulation of axon terminals releases neurotransmitter/neuropeptide or induces altered neurotransmitter release in a vicinity of neighboring non-neuronal cells such as secretory or other cells and modulates cell activity of the neighboring or nearby non-neuronal cells, including the postsynaptic cells. Further, via such modulation, modulation of other tissue structures or organs may be achieved, without direct stimulation. In one embodiment, direct energy application to a relatively small region of an organ (e.g., a volume less than 25% of the total organ volume) may be used to trigger action potentials in afferent neurons that project into different areas of the brain (e.g., the hypothalamus). However, this result may be achieved without direct brain stimulation of synapse-rich regions. The direct brain stimulation may result in undesired activation of other pathways that may interfere with or swamp a desired physiological outcome. Further, direct brain stimulation may involve invasive procedures. Accordingly, the present techniques permit granular activation of either brain activity or activity within an organ, tissue or structure in a manner that is more targeted and more specific than direct brain stimulation or electrical peripheral nerve stimulation. That is, granular activation permits activation of only certain molecules and not others and/or in certain tissues and not others in a predictable and targeted manner.

Benefits of the present techniques include local modulation at the region of interest of the tissue to achieve effects that change a concentration of one or more molecules of interest. Further, the local modulation may involve direct activation of a relatively small region of tissue (e.g., less than 25% of a total tissue volume) to achieve these effects. In this manner, the total applied energy is relatively small to achieve a desired physiological outcome. In certain embodiments, the applied energy may be from a non-invasive extracorporeal energy source (e.g., ultrasound energy source, mechanical vibrator). For example, a focused energy probe may apply energy through a subject's skin and is focused on a region of interest of an internal tissue. Such embodiments achieve the desired physiological outcome without invasive procedures or without side effects that may be associated with other types of procedures or therapy.

Further, the present techniques relate to multi-site control of complex physiological processes. In some embodiments, a first energy application at a first region of interest may induce a first outcome (e.g., increased/decreased concentration of one or more molecules that falls outside a desired range). A second energy application may be applied to a second, different region of interest, to cause an outcome in an opposite direction (e.g. decreased/increased concentration of the one or more molecules so that it falls in the desired range). In this manner, a concentration of a molecule of interest may be selectively modulated. The first and the second region of interest may be in the same organ, tissue or structure or may be in different organ, tissue or structure. In some embodiments, the first outcome may be associated with an excess activating of one pathway and second outcome may be associated with a competing pathway or a deactivation pathway, providing a compensation effect to the first outcome to achieve bi-directional control or tuning of a metabolic pathway or a concentration of a molecule of interest.

In a non-limiting example, to control a circulating glucose concentration in a hyperglycemic subject to be in a desired range, a first energy may be applied to a first region of interest that causes a decrease in circulating glucose concentration. However, to avoid overcorrection of glucose and resulting hypoglycemia, a second energy may also be applied to a second region of interest, different from the first region of interest, and that causes an increase or decrease in a circulating molecule concentration that may adjust or stabilize glucose concentration to a desired range. Accordingly, in one example, a first energy may be applied to a first region of interest in the liver to cause a decrease in circulating glucose concentration, i.e., a first molecule of interest. A second energy may also be applied to a second region of interest in a pancreas to cause an increase in glucagon, i.e., a second molecule of interest which in turn may result in an increase in circulating glucose, i.e., the first molecule of interest. However, size of the effect on circulating glucose based on the first energy application relative to the second energy application may be different in scale. That is, the first energy application may cause a relatively larger glucose concentration drop than the second energy application causes the glucose to increase in the same subject. In this manner, the glucose endpoint may be tuned by calibrating the treatment at the first region of interest and the second region of interest to achieve the desired targeted physiological outcome.

Further, to achieve targeted tuning, the modulation parameters of the energy application to the first region of interest may be the same or different than the modulation parameters at the second region of interest. This may be calibrated to the particular site of energy application. In some embodiments, a first region of interest may have a wider dynamic range of physiological outcomes relative to a second region of interest. Accordingly, adjustably controlling the energy application at the first region of interest may have more diverse effects, while adjustably controlling the energy application at the second region of interest may have a narrower range of effects. Further, this may differ from patient to patient. A diseased organ may respond differently to energy application relative to a healthy organ.

Selective modulation as provided herein may be triggered by a deviation of a concentration (e.g., a circulating concentration, a tissue concentration) of a molecule of interest from a desired range. Based on the nature of the deviation (above or below the desired range), energy may be applied to the appropriate region of interest. For example, a determination that a concentration of a molecule of interest is above a desired concentration may trigger application of energy to a region of interest to cause a decrease in the concentration of the molecule of interest. Bi-directional control may be achieved via application of energy to the region of interest associated with the competing pathway. Further, the determination that the concentration of the molecule of interest is within the target concentration range may yield instructions not to trigger application of energy or to trigger a lower level of energy application.

In one embodiment, while a direct energy application (i.e., direct stimulation) of a region of interest in the pancreas may be used to cause an increase in circulating insulin concentration as a result of increased pancreatic insulin production, energy may also be applied to a region of interest in the gastrointestinal tissue to cause a competing decrease in circulating insulin concentration. In certain embodiments, energy application to more than two regions of interest may be applied and may work in concert to control circulating insulin concentration to be in a desired range. For example, target regions of interest may be in the liver, pancreas, or gastrointestinal tissue.

In certain embodiments, techniques for neuromodulation are provided in which energy from an energy source (e.g., an external or extracorporeal energy source) is applied to axon terminals in a manner such that the induced physiological outcome, for example, neurotransmitter release, at the site of focus of the energy application, e.g., the axon terminals, is triggered in response to the energy application and not in response to an action potential. That is, the application of energy directly to the axon terminals acts in lieu of an action potential to facilitate neurotransmitter release into a neuronal junction (i.e., synapse) with a non-neuronal cell. The application of energy directly to the axon terminals further induces an altered neurotransmitter release from the axon terminal within the synapse (e.g., axoextracellular synapse) into the vicinity of neighboring non-neuronal cells. In one embodiment, the energy source is an extracorporeal energy source, such as an ultrasound energy source or a mechanical vibrator. In this manner, non-invasive and targeted neuromodulation may be achieved directly at the site of energy focus rather than via stimulation at an upstream site that in turn triggers an action potential to propagate to the downstream site target and to activate downstream targets.

In certain embodiments, the target tissues are internal tissues or organs that are difficult to access using electrical stimulation techniques with electrodes. Contemplated tissue targets include gastrointestinal (GI) tissue (stomach, intestines), muscle tissue (cardiac, smooth and skeletal), epithelial tissue (epidermal, organ/GI lining), connective tissue, glandular tissues (exocrine/endocrine), etc. In one example, focused application of energy at a neuromuscular junction facilitates neurotransmitter release at the neuromuscular junction without an upstream action potential. In one embodiment, Contemplated targets for modulation may include portions of a pancreas responsible for controlling insulin release or portions of the liver responsible for glucose regulation.

To that end, the disclosed neuromodulation techniques may be used in conjunction with a neuromodulation system. FIG. 1 is a schematic representation of a system 10 for neuromodulation to achieve neurotransmitter release and/or activate components (e.g., the presynaptic cell, the postsynaptic cell) of a synapse in response to an application of energy. The depicted system includes a pulse generator 14 coupled to an energy application device 12 (e.g., an ultrasound transducer). The energy application device 12 is configured to receive energy pulses, e.g., via leads or wireless connection, that in use are directed to a region of interest of an internal tissue or an organ of a subject, which in turn results in a targeted physiological outcome. In certain embodiments, the pulse generator 14 and/or the energy application device 12 may be implanted at a biocompatible site (e.g., the abdomen), and the lead or leads couple the energy application device 12 and the pulse generator 14 internally. For example, the energy application device 12 may be a MEMS transducer, such as a capacitive micromachined ultrasound transducer.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device, e.g., may operate to apply energy transdermally or in a noninvasive manner from a position outside of a subject's body, and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation to achieve targeted physiological outcome or clinical effects.

In certain embodiments, the system 10 may include an assessment device 20 that is coupled to the controller 16 and assesses characteristics that are indicative of whether the targeted physiological outcome of the modulation have been achieved. In one embodiment, the targeted physiological outcome may be local. For example, the modulation may result in local tissue or function changes, such as tissue structure changes, local change of concentration of certain molecules, tissue displacement, increased fluid movement, etc.

The modulation may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 20 may be configured to assess concentration changes in some embodiments. In some embodiments, the assessment device 20 may be an imaging device configured to assess changes in organ size and/or position. While the depicted elements of the system 10 are shown separately, it should be understood that some or all of the elements may be combined with one another. Further, some or all of the elements may communicate in a wired or wireless manner with one another.

Based on the assessment, the modulation parameters of the controller 16 may be altered. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 16, either by an operator or via an automatic feedback loop, for defining or adjusting the energy application parameters or modulation parameters of the pulse generator 14.

The system 10 as provided herein may provide energy pulses according to various modulation parameters. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. The treatment duration may last for various time periods, including, but not limited to, from a few minutes to several hours. In certain embodiments, treatment duration with a specified stimulation pattern may last for one hour, repeated at, e.g., 72 hour intervals. In certain embodiments, treatment may be delivered at a higher frequency, say every three hours, for shorter durations, for example, 30 minutes. The application of energy, in accordance with modulation parameters, such as the treatment duration and frequency, may be adjustably controlled to achieve a desired result.

Figure 2:
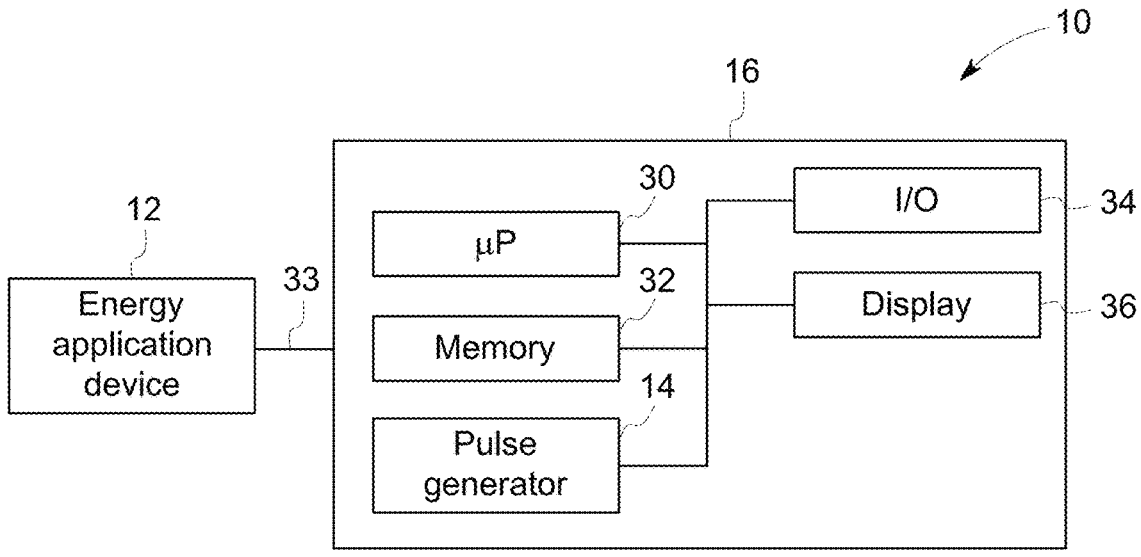
FIG. 2 is a block diagram of a neuromodulation system according to embodiments of the disclosure.

FIG. 2 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly.

The controller 16 also includes a user interface with input/output circuitry 34 and a display 36 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from controller device 16 to vary the stimulation characteristics of energy pulses transmitted through lead 33 to an subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times or cancelling/suppressing energy application at certain times. In one embodiment, the adjustable control of the energy application device is based on information about a concentration of one or more molecules in the subject (e.g., a circulating molecule). If the information is from the assessment device 20, a feedback loop may drive the adjustable control. For example, if a circulating glucose concentration, as measured by the assessment device 20, is above a predetermined threshold or range, the controller 16 may initiate energy application to a region of interest (e.g., liver) and with modulation parameters that are associated with a reduction in circulating glucose. The initiation of energy application may be triggered by the glucose concentration drifting above a predetermined (e.g., desired) threshold or outside a predefined range. In another embodiment, the adjustable control may be in the form of altering modulation parameters when an initial application of energy does not result in an expected change in a targeted physiological outcome (e.g., concentration of a molecule of interest) within a predetermined time frame (e.g., 1 hour, 2 hours, 4 hours, 1 day).

In one embodiment, the memory 32 stores different operating modes that are selectable by the operator. For example, the stored operating modes may include instructions for executing a set of modulation parameters associated with a particular treatment site, such as regions of interest in the liver, pancreas, gastrointestinal tract, spleen. Different sites may have different associated modulation parameters. Rather than having the operator manually input the modes, the controller 16 may be configured to execute the appropriate instruction based on the selection. In another embodiment, the memory 32 stores operating modes for different types of treatment. For example, activation may be associated with a different stimulating pressure or frequency range relative to those associated with depressing or blocking tissue function. In a specific example, when the energy application device is an ultrasound transducer, the time-averaged power (temporal average intensity) and peak positive pressure are in the range of 1 mW/cm²-30,000 mW/cm² (temporal average intensity) and 0.1 MPa to 7 MPa (peak pressure). In one example, the temporal average intensity is less than 35 W/cm² in the region of interest to avoid levels associated with thermal damage & ablation/cavitation. In another specific example, when the energy application device is a mechanical actuator, the amplitude of vibration is in the range of 0.1 to 10 mm. The selected frequencies may depend on the mode of energy application, e.g., ultrasound or mechanical actuator.

In another embodiment, the memory 32 stores a calibration or setting mode that permits adjustment or modification of the modulation parameters to achieve a desired result. In one example, the stimulation starts at a lower energy parameter and increases incrementally, either automatically or upon receipt of an operator input. In this manner, the operator may achieve tuning of the induced effects as the modulation parameters are being changed.

The system may also include an imaging device that facilitates focusing the energy application device 12. In one embodiment, the imaging device may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 32 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 12 may be focused on the selected volume corresponding to the region of interest. For example, the energy application device 12 may be configured to first operate in the targeting mode to apply a targeting mode energy that is used to capture image data to be used for identifying the region of interest. The targeting mode energy is not at levels and/or applied with modulation parameters suitable for preferential activation. However, once the region of interest is identified, the controller 16 may then operate in a treatment mode according to the modulation parameters associated with preferential activation.

The controller 16 may also be configured to receive inputs related to the targeted physiological outcomes as an input to the selection of the modulation parameters. For example, when an imaging modality is used to assess a tissue characteristic, the controller 16 may be configured to receive a calculated index or parameter of the characteristic. Based on whether the index or parameter is above or below a predefined threshold, the modulation parameters may be modified. In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 (e.g., an ultrasound transducer) may operate under control of the controller 16 to a) acquire image data of a tissue that may be used to spatially select a region of interest within the target tissue b) apply the modulating energy to the region of interest and c) acquire image to determine that the targeted physiological outcome has occurred (e.g., via displacement measurement). In such an embodiment, the imaging device, the assessment device 20 and the energy application device 12 may be the same device.

In another implementation, a desired modulation parameter set may also be stored by the controller 16. In this manner, subject-specific parameters may be determined. Further, the effectiveness of such parameters may be assessed over time. If a particular set of parameters is less effective over time, the subject may be developing insensitivity to activated pathways. If the system 10 includes an assessment device 20, the assessment device 20 may provide feedback to the controller 16. In certain embodiments, the feedback may be received from a user or an assessment device 20 indicative of a characteristic of the target physiological outcome. The controller 16 may be configured to cause the energy application device to apply the energy according to modulation parameters and to dynamically adjust the modulation parameters based on the feedback. For example, based on the feedback, the processor 16 may automatically alter the modulation parameters (e.g., the frequency, amplitude, or pulse width of an ultrasound beam or mechanical vibration) in real time and responsive to feedback from the assessment device 20.

In one example, the present techniques may be used to treat a subject with a metabolic disorder. The present techniques may also be used to regulate blood glucose level in subjects with disorders of glucose regulation. Accordingly, the present techniques may be used to promote homeostasis of a molecule of interest or to promote a desired circulating concentration or concentration range of one or more molecules of interest (e.g., glucose, insulin, glucagon, or a combination thereof). In one embodiment, the present techniques may be used to control circulating (i.e., blood) glucose levels. In one embodiment, the following thresholds may be used to maintain blood glucose levels in a dynamic equilibrium in the normal range:

Fasted:
    Less than 50 mg/dL (2.8 mmol/L): Insulin Shock
    50-70 mg/dL (2.8-3.9 mmol/L): low blood sugar/hypoglycemia
    70-110 mg/dL (3.9-6.1 mmol/L): normal
    110-125 mg/dL (6.1-6.9 mmol/L): elevated/impaired (pre-diabetic)
    125 (7 mmol/L): diabetic
    Non-fasted (postprandial approximately 2 hours after meal):
    70-140 mg/dL: Normal
    140-199 mg/dL (8-11 mmol/L): Elevated or "borderline"/ prediabetes
    More than 200 mg/dL: (11 mmol/L): Diabetes For example, the techniques may be used to maintain circulating glucose concentration to be under about 200 mg/dL and/or over about 70 mg/dL. The techniques may be used to maintain glucose in a range between about 4-8 mmol/L or about 70-150 mg/dL. The techniques may be used to maintain a normal blood glucose range for the subject (e.g., a patient), where the normal blood glucose range may be an individualized range based on the patient's individual factors such as weight, age, clinical history. Accordingly, the application of energy to one or more regions of interest may be adjusted in real time based on the desired end concentration of the molecule of interest and may be adjusted in a feedback loop based on input from an assessment device 20. For example, if the assessment device 20 is a circulating glucose monitor or a blood glucose monitor, the real-time glucose measurements may be used as input to the controller 16.

In another embodiment, the present techniques may be used to induce a characteristic profile of physiological changes. For example, the characteristic profile may include a group of molecules of interest that increase in concentration in the tissue and/or blood as a result of the energy application and another group of molecules of interest that decrease in concentration in the tissue and/or blood as a result of the energy application. The characteristic profile may include a group of molecules that do not change as a result of the energy application. The characteristic profile may define concurrent changes that are associated with a desired physiological outcome. For example, the profile may include a decrease in circulating glucose seen together with an increase in circulating insulin.

Figure 3:
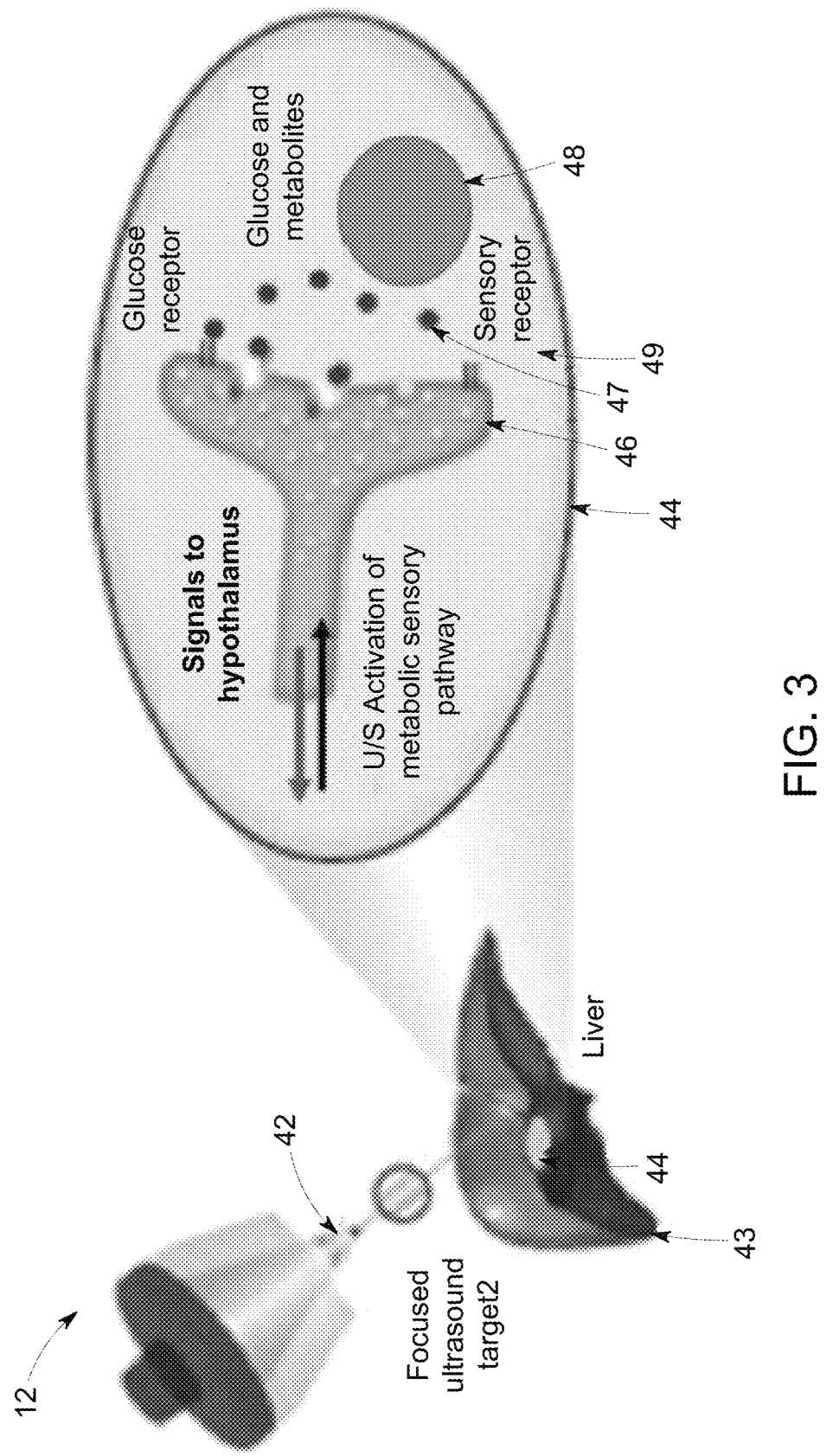
FIG. 3 is a schematic representation of an ultrasound energy application device in operation according to embodiments of the disclosure.

FIG. 3 is a specific example in which the energy application device 12 includes an ultrasound transducer 42 that is capable of applying energy to a target tissue 43, shown by way of non-limiting example as a liver. The energy application device 12 may include control circuitry for controlling the ultrasound transducer 42. The control circuitry of the processor 30 may be integral to the energy application device 12 (e.g., via an integrated controller 16) or may be a separate component. The ultrasound transducer 42 may also be configured to acquire image data to assist with spatially selecting a desired or targeted region of interest and focusing the applied energy on the region of interest of the target tissue or structure.

The desired target tissue 43 may be an internal tissue or an organ that includes synapses of axon terminals 46 and non-neuronal cells 48. The synapses may be stimulated by direct application of energy to the axon terminals within a field of focus of the ultrasound transducer 42 focused on a region of interest 44 of the target tissue 43 to cause release of molecules into the synaptic space 49. In the depicted embodiment, the axon terminal 46 forms a synapse with a liver cell, and the release of neurotransmitters 47 and/or the change in ion channel activity in turn causes downstream effects such as activation of glucose metabolism. The region of interest may be selected to include a certain type of axon terminal 46, such as an axon terminal 46 of a particular neuron type and/or one that forms a synapse with a certain type of non-neuronal cell. Accordingly, the region of interest 44 may be selected to correspond to a portion of the target tissue 43 with the desired axon terminals 46 (and associated non-neuronal cells 48). The energy application may be selected to preferentially trigger a release of one or more molecules such as neurotransmitters from the nerve within the synapse or directly activate the non-neuronal cell itself through direct energy transduction (i.e. mechanotransduction or voltage-activated proteins within the non-neuronal cells), or cause an activation within both the neural and non-neuronal cells that elicits a desired physiological effect. The region of interest may be selected as the site of nerve entry into the organ. In one embodiment, liver stimulation or modulation may refer to a modulation of the region of interest 44 at or adjacent to the porta hepatis.

The energy may be focused or substantially concentrated on a region of interest 44 and to only part of the internal tissue 43, e.g., less than about 50%, 25%, 10%, or 5% of the total volume of the tissue 43. In one embodiment, energy may be applied to two or more regions of interest 44 in the target tissue 43, and the total volume of the two or more regions of interest 44 may be less than about 90%, 50%, 25%, 10%, or 5% of the total volume of the tissue 43. In one embodiment, the energy is applied to only about 1%-50% of the total volume of the tissue 43, to only about 1%-25% of the total volume of the tissue 43, to only about 1%-10% of the total volume of the tissue 43, or to only about 1%-5% of the total volume of the tissue 43. In certain embodiments, only axon terminals 46 in the region of interest 44 of the target tissue 43 would directly receive the applied energy and release neurotransmitters while the unstimulated axon terminals outside of the region of interest 44 do not receive substantial energy and, therefore, are not activated/stimulated in the same manner. In some embodiments, axon terminals 46 in the portions of the tissue directly receiving the energy would induce an altered neurotransmitter release. In this manner, tissue subregions may be targeted for neuromodulation in a granular manner, e.g., one or more subregions may be selected. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 mm³. In certain embodiments, the energy may be focused or concentrated within a volume of about 0.5 mm³-50 mm³. A focal volume and a focal depth for focusing or concentrating the energy within the region of interest 44 may be influenced by the size/configuration of the energy application device 12. The focal volume of the energy application may be defined by the field of focus of the energy application device 12.

Figure 4A:
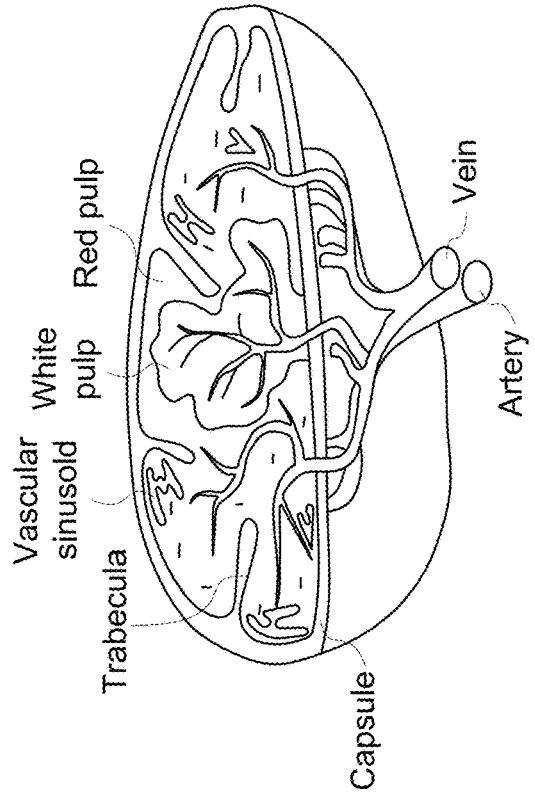
FIG. 4A is an ultrasound visualization of the spleen that may be used as spatial information to focus on a region of interest in a spleen according to embodiments of the disclosure.
Figure 4A:
Figure 4B:
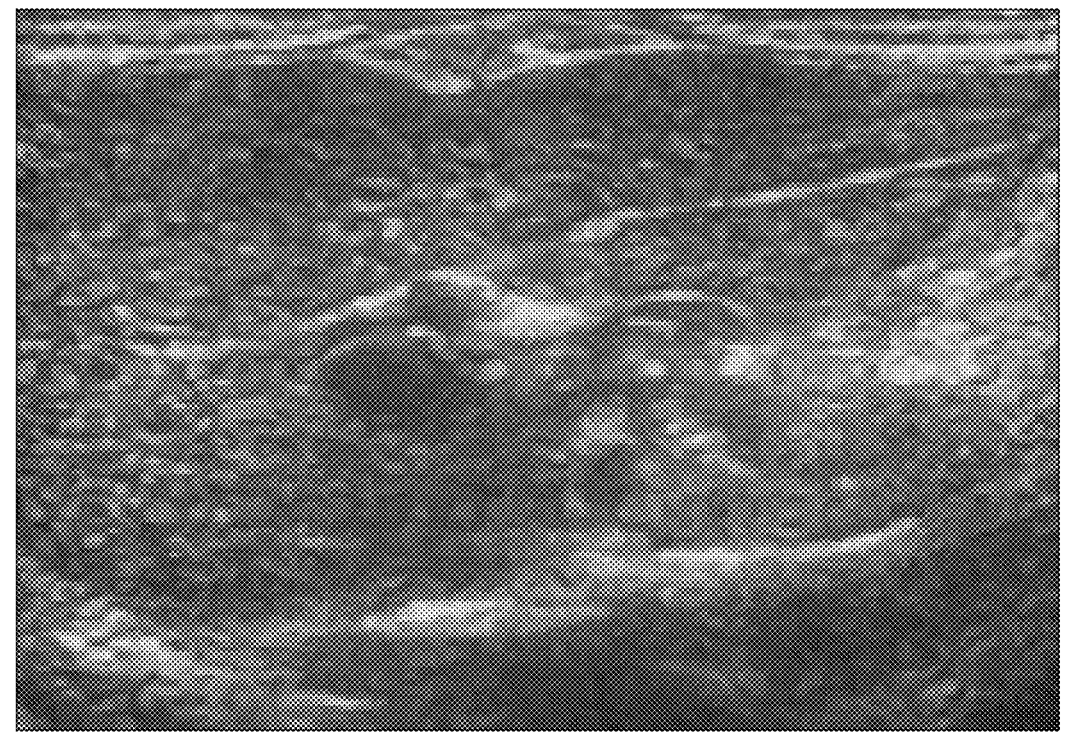
FIG. 4B is an ultrasound visualization of the liver that may be used as spatial information to focus on a region of interest in a liver according to embodiments of the disclosure.

As provided herein, the energy may be substantially applied only to the region or regions of interest 44 to preferentially activate the synapse in a targeted manner to achieve targeted physiological outcomes and is not substantially applied in a general or a nonspecific manner across the entire tissue 43. Accordingly, only a subset of a plurality of different types of axon terminals 46 in the tissue 43 is exposed to the direct energy application. FIG. 4 is an image of blood flow (as obtained with a Doppler ultrasound) within a spleen that may serve as spatial information for spatially selecting the region of interest of the targeted organ. For example, the regions of interest within organs containing either blood vessels, nerves, or other anatomical landmarks may be spatially selected and used to identify areas with specific axon terminals and synapses. In one embodiment, the region of interest is selected by identifying a splenic artery and spatially selecting an area close to or parallel to the splenic artery. Organ architectures may be segmented based on sub-organ tissue function, blood vessel, and neural innervation, and subsets of axon terminals may be selected to be included in a region of interest to which energy is directly applied. Other axon terminals may be outside of the region of interest and may not be exposed to the direct applied energy. The individual axon terminal or terminals to include in the region of interest may be selected based on factors including, but not limited to, historical or experimental data (e.g., data showing an association of a particular location with a desired or targeted physiological outcome). In another embodiment, the location of the axon terminals and their adjacent tissue or structures may be used to select an individual axon terminal from the total set of axon terminals for preferential activation. Alternatively or additionally, the system 10 may apply energy to individual axon terminals until the desired targeted physiological effect is achieved. It should be understood that the spleen image is by way of example only. The disclosed selection of axon terminals for preferential activation via a direct energy application to the region of interest using spatial information of visualized nerves may be used in conjunction with other organs or structures (e.g., liver, pancreas, gastrointestinal tissue).

The disclosed techniques may be used in assessment of neuromodulation effects, which in turn may be used as an input or a feedback for selecting or modifying neuromodulation parameters. The disclosed techniques may use direct assessments of tissue condition or function as the targeted physiological outcomes. The assessment may occur before (i.e., baseline assessment), during, and/or after the neuromodulation.

The assessment techniques may include at least one of functional magnetic resonance imaging, diffusion tensor magnetic resonance imaging, positive emission tomography, or acoustic monitoring, thermal monitoring. The assessment techniques may also include protein and/or marker concentration assessment. The images from the assessment techniques may be received by the system for automatic or manual assessment. Based on the image data, the modulation parameters may also be modified. For example, a change in organ size or displacement may be utilized as a marker of local neurotransmitter concentration, and used as a surrogate marker for exposure of local cells to phenotype modulating neurotransmitters, and effectively as a marker of predicted effect on glucose metabolic pathways. The local concentration may refer to a concentration within a field of focus of the energy application.

Additionally or alternatively, the system may assess the presence or concentration of one or more molecules in the tissue or circulating in the blood. The concentration in the tissue may be referred to as a local concentration or resident concentration. Tissue may be acquired by a fine needle aspirate, and the assessment of the presence or levels of molecules of interest (e.g., metabolic molecules, markers of metabolic pathways, peptide transmitters, catecholamines) may be performed by any suitable technique known to one of ordinary skilled in the art.

In other embodiments, the targeted physiological outcomes may include, but are not limited to, tissue displacement, tissue size changes, a change in concentration of one or more molecules (either local, non-local, or circulating concentration), a change in gene or marker expression, afferent activity, and cell migration, etc. For example, tissue displacement (e.g., liver displacement) may occur as a result of energy application to the tissue. By assessing the tissue displacement (e.g., via imaging), other effects may be estimated. For example, a certain displacement may be characteristic of a particular change in molecule concentration. In one example, a 5% liver displacement may be indicative of or associated with a desired reduction in circulating glucose concentration based on empirical data. In another example, the tissue displacement may be assessed by comparing reference image data (tissue image before application of energy to the tissue) to post-treatment image data (tissue image taken after application of energy to the tissue) to determine a parameter of displacement. The parameter may be a maximum or average displacement value of the tissue. If the parameter of displacement is greater than a threshold displacement, the application of energy may be assessed as being likely to have caused the desired targeted physiological outcome.

Figure 5:
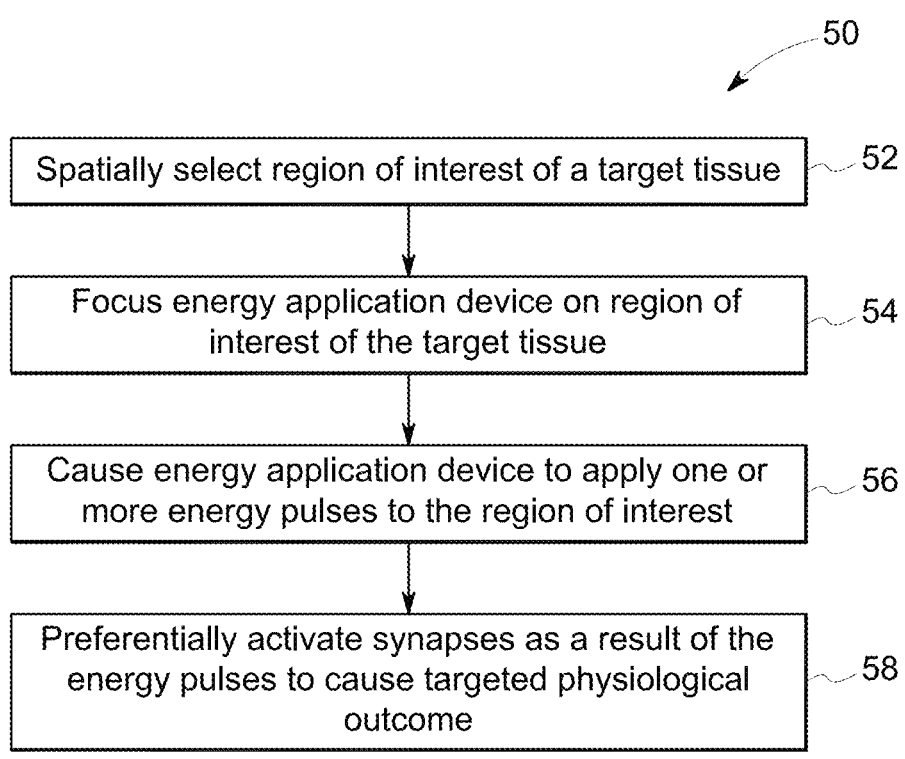
FIG. 5 is a flow diagram of a neuromodulation technique according to embodiments of the disclosure.

FIG. 5 is a flow diagram of a method 50 for stimulating a region of interest of a target tissue. In the method 50, the region of interest is spatially selected 52. The energy application device is positioned such that the energy pulses are focused at the desired region of interest at step 54, and the pulse generator applies a plurality of energy pulses to the region of interest of the target tissue at step 56 to preferentially activate a subset of synapses in the target tissue, e.g., to stimulate the axon terminal to release neurotransmitters and/or induce altered neurotransmitter release and/or induce altered activity in the non-neuronal cell (within the synapse) to cause a targeted physiological outcome at step 58 as provided herein. In certain embodiments, the method may include a step of assessing the effect of the stimulation. For example, one or more direct or indirect assessments of a state of tissue function or condition may be used. Based on the tissue function as assessed, the modulation parameters of the one or more energy pulses may be modified (e.g., dynamically or adjustably controlled) to achieve the targeted physiological outcome.

In one embodiment, assessments may be performed before and after applying energy pulses to assess a change in glucose concentration as a result of the modulation. If the glucose concentration is above or below a threshold, appropriate modification in the modulation parameters may be made. For example, if the glucose concentration with desired physiological outcome, the energy applied during neuromodulation may be stepped back to a minimum level that supports the desired outcome. If the change in the characteristic relative to the threshold is associated with insufficient change in glucose concentration, certain modulation parameters, including, but not limited to, the modulation amplitude or frequency, the pulse shape, the stimulation pattern, and/or the stimulation location may be changed.

Further, the assessed characteristic or condition may be a value or an index, for example, a flow rate, a concentration, a cell population, or any combination thereof, which in turn may be analyzed by a suitable technique. For example, a relative change exceeding a threshold may be used to determine if the modulation parameters are modified. The desired modulation may be assessed via a measured clinical outcome, such as a presence or absence of an increase in tissue structure size (e.g., lymph node size) or a change in concentration of one or more released molecules (e.g., relative to the baseline concentration before the neuromodulation). In one embodiment, a desired modulation may involve an increase in concentration above a threshold, e.g., above a about 50%, 100%, 200%, 400%, 1000% increase in concentration relative to baseline. For blocking treatments, the assessment may involve tracking a decrease in concentration of a molecule over time, e.g., at least a 10%, 20%, 30%, 50%, or 75% decrease in the molecule of interest. Further, for certain subjects, the desired blocking treatment may involve keeping a relatively steady concentration of a particular molecule in the context of other clinical events that may tend to increase the concentration of the molecule. That is, desired blocking may block a potential increase. The increase or decrease or other induced and measurable effect may be measured within a certain time window from the start of a treatment, e.g., within about 5 minutes, within about 30 minutes. In certain embodiments, if the neuromodulation is determined to be desired, the change in the neuromodulation is an instruction to stop applying energy pulses. In another embodiment, one or more parameters of the neuromodulation are changed if the neuromodulation is not desired. For example, the change in modulation parameters may be an increase in pulse repetition frequency, such as a stepwise increase in frequency of 10-100 Hz and assessment of the desired characteristic until a desired neuromodulation is achieved. In another implementation, a pulse width may be changed. In other embodiments, two or more of the parameters may be changed together, in parallel or in series. If the neuromodulation is not desired after multiple parameter changes, the focus (i.e., the site) of energy application may be changed.

Figure 6:
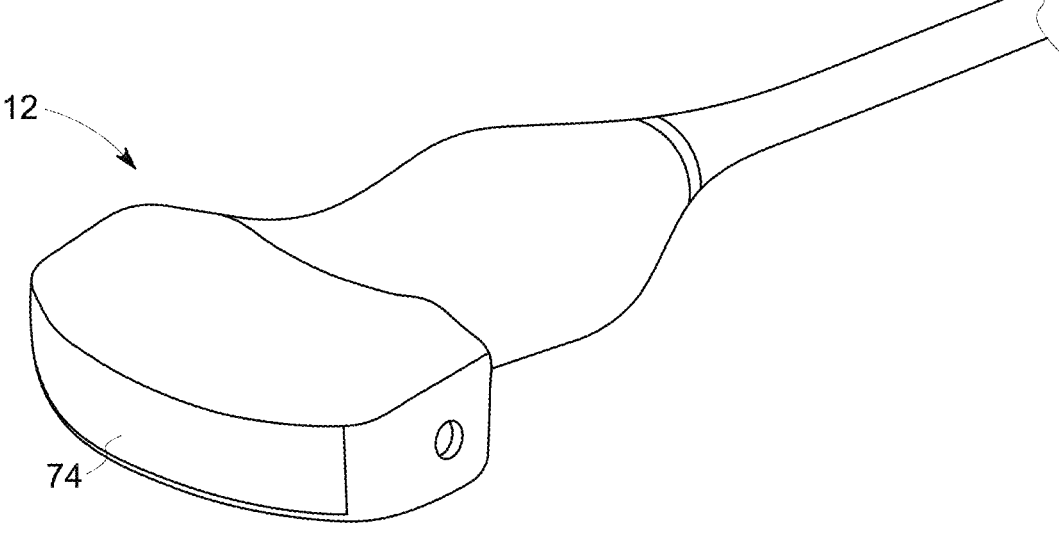
FIG. 6 is a schematic illustration of the energy application device configured as an extracorporeal device and including an ultrasound transducer.

The energy application device 12 may be configured as an extracorporeal non-invasive device or an internal device, e.g., a minimally invasive device. As noted, the energy application device 12 may be an extracorporeal noninvasive ultrasound transducer or mechanical actuator. For example, FIG. 6 shows an embodiment of the energy application device 12 configured as a handheld ultrasound probe including an ultrasound transducer 74. However, it should be understood that other noninvasive implementations are also contemplated, including other methods to configure, adhere, or place ultrasound transducer probes over an anatomical target. Further, in addition to handheld configurations, the energy application device 12 may include steering mechanisms responsive to instructions from the controller 16. The steering mechanisms may orient or direct the energy application device 12 towards the target tissue 43 (or structure), and the controller 16 may then focus the energy application onto the region of interest 44.

EXAMPLES

Figure 7:
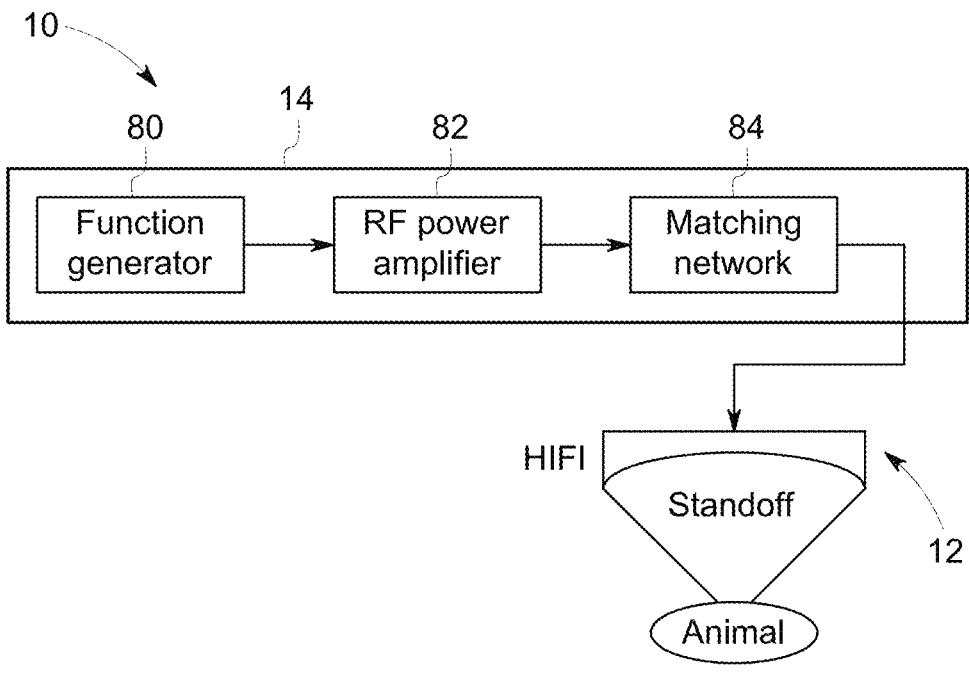
FIG. 7 is a schematic illustration of the energy application device and the pulse generator configured to apply high-intensity focused ultrasound.
Figure 8:
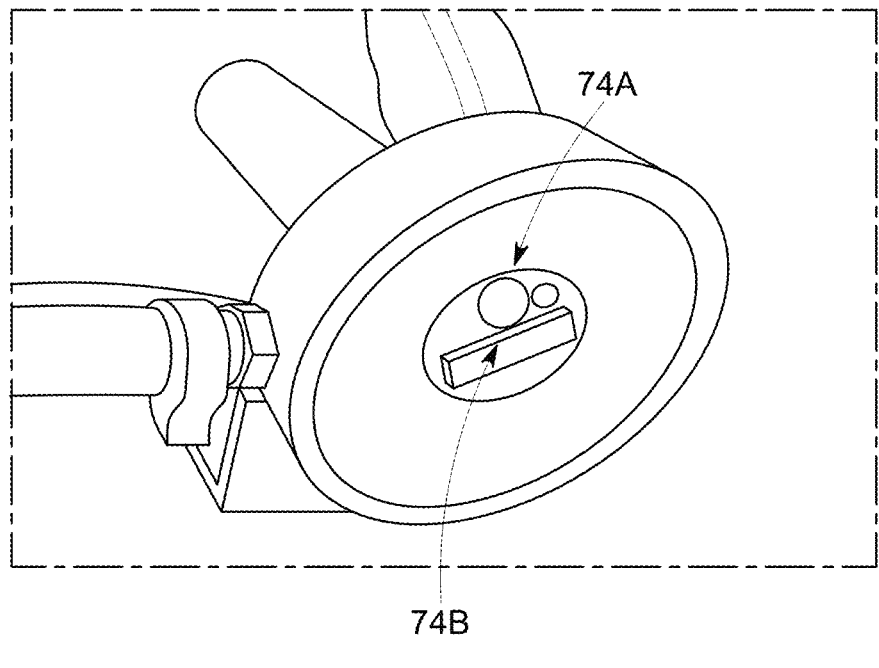
FIG. 8 is an example of an energy application device that may be used in conjunction with the system of FIG. 7.

FIG. 7 is a block diagram of the system 10 including the energy application device 12 and the pulse generator 14 configured to apply High-Intensity Focused Ultrasound (HIFU). In one embodiment, the system 10 includes, for example, a pulse generator including a function generator 80, a power amplifier 82, and a matching network 84. In one embodiment used to generate experimental results as provided herein, the pulse generator included a 1.1 MHz, high intensity focused ultrasound (HIFU) transducer (Sonic Concepts H106), a matching network (for example, Sonic Concepts), an RF power amplifier (ENI 350L) and a function generator (Agilent 33120A). In the depicted example, the 70-mm-diameter HIFU transducer has a spherical face with a 65-mm radius of curvature with a 20-mm-diameter hole in the center into which an imaging transducer can be inserted. The transducer depth of focus is 65 mm. The numerically simulated pressure profile has a full width at half amplitude of 1.8 mm laterally and 12 mm in the depth direction. The HIFU transducer 12 was coupled to the animal subject through a 6 cm tall plastic cone filled with degassed water. FIG. 8 is an example of an energy application device that may be used in conjunction with the system 10 of FIG. 7 including a HIFU transducer 74A and an imaging ultrasound transducer 74B arranged in a single energy application device 12 that may be controlled, e.g., by the controller 16, to apply energy and to image the target tissue as provided herein.

Figures 9, 10:
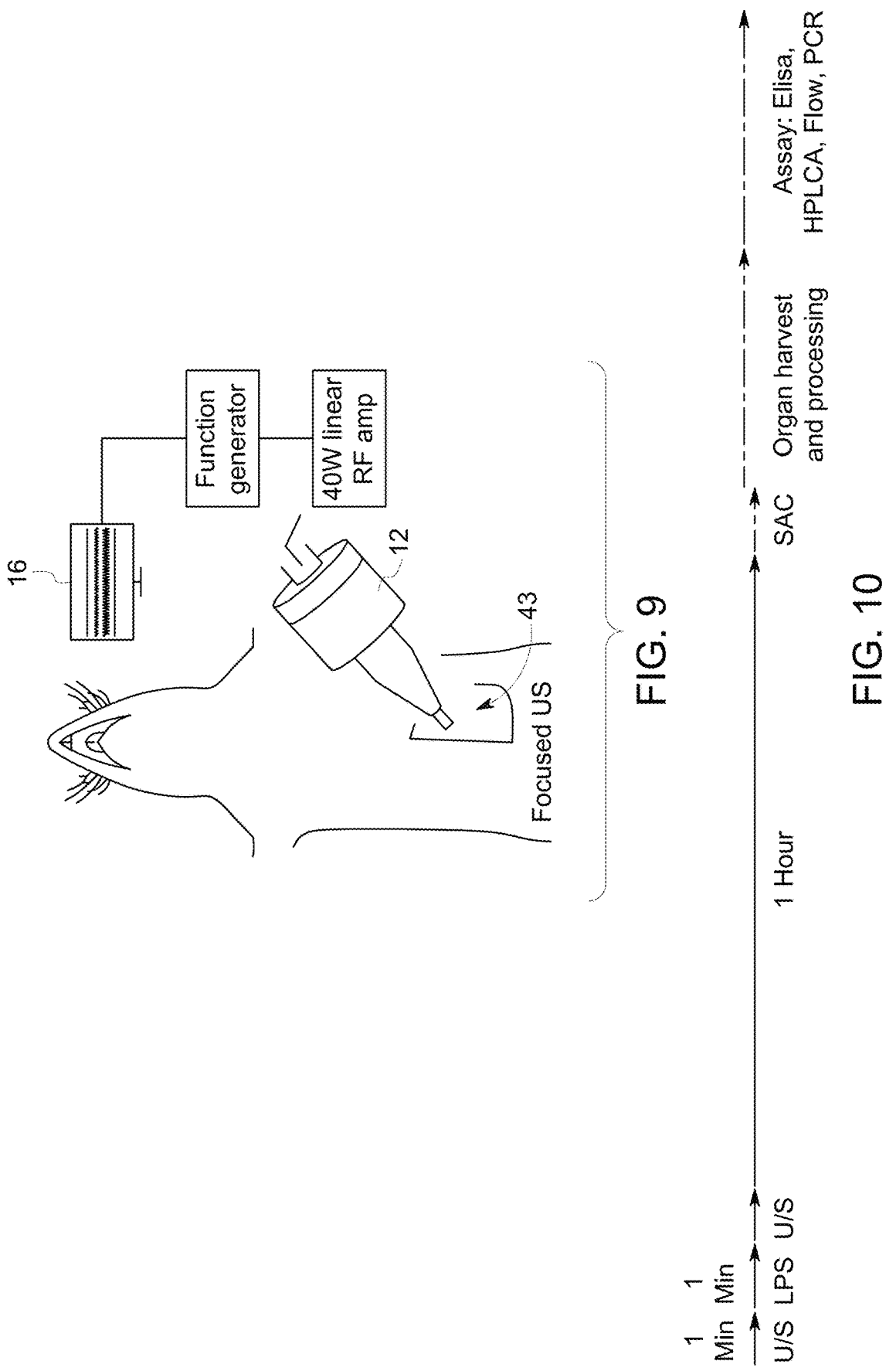
FIG. 9 is a schematic illustration of the experimental setup for ultrasound energy application to achieve target physiological outcomes.
FIG. 10 is an experimental timeline of ultrasound energy application.

FIG. 9 shows an experimental setup used to perform certain splenic modulation experiments as provided herein. While the depicted embodiment shows a splenic target tissue 43, it should be understood that certain elements of the experimental setup may be common between different target tissues 43. For example, the energy application device 12 may operate according to parameters set by the controller 16 to apply energy to a region of interest in the target tissue 43. As discussed herein, the target tissue may be a spleen, liver, pancreas, gastrointestinal tissue, etc. While the depicted experimental setup is shown with a 40 W RF amplifier, this is by way of example only, and other amplifiers (e.g., linear amplifiers) may be used. In certain setups, the rat heads are inserted in a birdcage coil FIG. 10 shows an experimental timeline for ultrasound energy application used to perform certain modulation experiments as provided herein. In the depicted embodiment, the ultrasound application was performed for 1 minute before and after lipopolysaccharide injection. Lipopolysaccharides (LPS) are bacterial membrane molecules that elicit a strong immune or inflammatory response. LPS from *Escherichia coli* 0111: B4 (Sigma-Aldrich) was used to produce a significant state of inflammation and metabolic dysfunction (e.g. hyperglycemia and insulin resistance) in naïve adult-Sprague Dawley (SD) rats. LPS was administered to animals (10 mg/kg) via intraperitoneal (IP) injection causing significant elevation in concentrations of TNF, circulating glucose, and insulin; these concentrations peaked in 4 hours but remained elevated as compared to control for up to 8 hours post injection. The animals were sacrificed at a time period after the ultrasound treatment for organ harvesting and processing. While the time period shown is 1 hour by way of example, it should be understood that, in other embodiments, the time period to assess induced changes may be variable.

Figure 11:
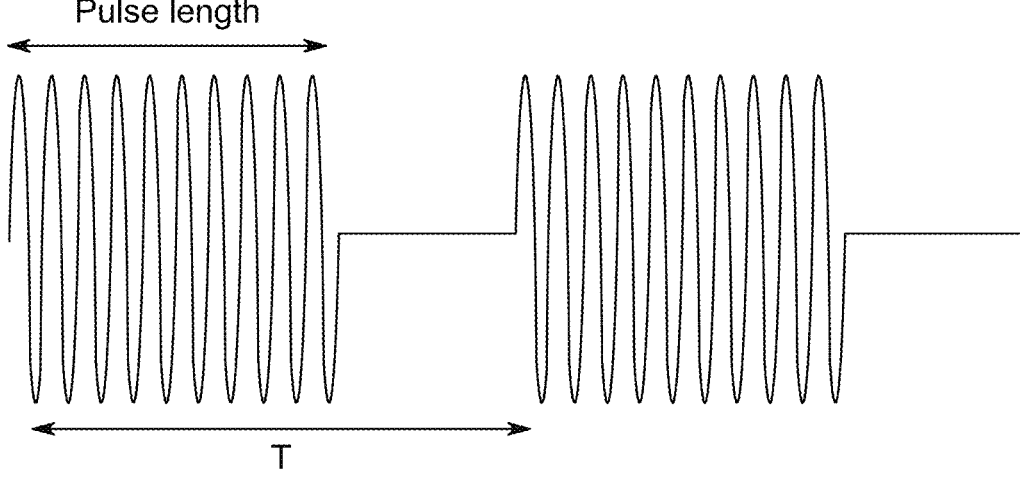
FIG. 11 shows pulse characteristics of the applied ultrasound energy pulses.

The function generator 80 generates a pulsed sinusoidal waveform, which is shown in FIG. 11. This pulsed sinusoidal waveform is amplified by the RF power amplifier and sent to the matching network of the HIFU transducer. Three ultrasound parameters can be adjusted during the animal experiment: pulse amplitude, pulse length and pulse repetition frequency. The pulse amplitude has a range of 0.5V-peak to 62V-peak. Three pulse lengths are used: 18.2 us, 136.4 us, and 363.6 us. In one embodiment, the pulse repetition frequency (1/T) is 2 kHz. The treatment time is 1 minute. The ultrasound modulation parameters are by way of example. In one embodiment, modulation is provided with an ultrasound stimulus having an ultrasound transducer frequency in a range of about 0.1 MHz to about 5 MHz and the ultrasound stimulus has an ultrasound frequency pulse repetition frequency in a range of about 0.1 Hz to about 10 kHz. The ultrasound cycles per pulse of the ultrasound energy may be in a range of about 1 to about 1000. In one embodiment, the pulse center frequency was 1.1 MHz, the pulse repetition period was 0.5 ms (corresponding to a pulse repetition frequency of 2000 Hz); the pulse amplitude and pulse length varied. Table 1 summarizes the HIFU ultrasound parameters.

| Transducer Frequency (MHz) | Pulse Amplitude (V-peak) | Pulse Length (us) | Repetition Frequency (Hz) | Peak Pressure (MPa) |
|---|---|---|---|---|
| 1.1 | 62 | 136.4 | 2000 | 1.72 |
| 1.1 | 46.5 | 136.4 | 2000 | 1.27 |
| 1.1 | 31 | 136.4 | 2000 | 0.83 |
| 1.1 | 15.5 | 136.4 | 2000 | 0.41 |
| 1.1 | 9.6 | 136.4 | 2000 | 0.25 |
| 1.1 | 7.75 | 136.4 | 2000 | 0.20 |
| 1.1 | 5 | 136.4 | 2000 | 0.13 |
| 1.1 | 0.5 | 136.4 | 2000 | 0.01 |
| 1.1 | 31 | 18.2 | 2000 | 0.83 |
| 1.1 | 31 | 363.6 | 2000 | 0.83 |

Figure 12:
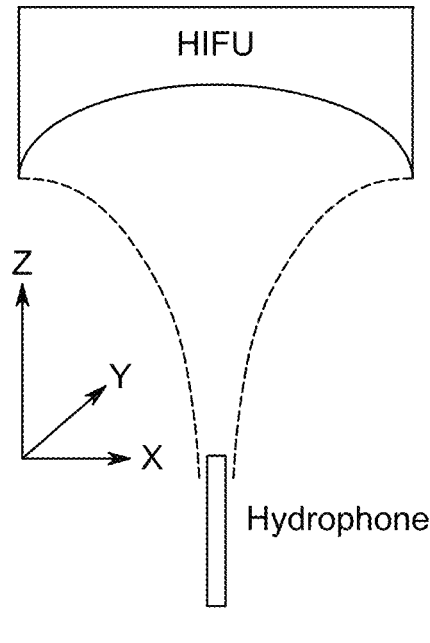
FIG. 12 shows a hydrophone measurement setup.

Pressure measurements were performed in degassed water using a HIFU hydrophone (HNA-0400) manufactured by Onda Corp. The HIFU transducer was driven by a 100-cycle sinusoidal waveform. The hydrophone was scanned through a focal spot with a grid size of 0.1 mm in the x-y plane and a step size of 0.2 mm along the z axis. FIG. 12 shows the hydrophone setup and FIG. 13A shows the scan result. The peak positive (negative) pressure is defined as the maximum positive (negative) pressure at the transducer focus in x-y plane. The input voltages were low enough to eliminate nonlinearity effects. Therefore, the value of the peak positive pressure was identical to the value of the peak negative pressure. In order to estimate the peak pressure at the full operating voltage, peak pressures were measured at several different driving voltages before cavitation occurs and performed curve fitting. The calculated peak pressures are shown in Table 1.

Ultrasound Targeting for Organ Specific Neuromodulation

A GE Vivid E9 ultrasound system and an 11 L probe were used for the ultrasound scan before neuromodulation started. The region of interest was labeled on animal skin. The HIFU transducer was positioned on the labeled area. Another ultrasound scan was also performed using a smaller imaging probe (3S), which was placed in the opening of the HIFU transducer. The imaging beam of the 3S probe was aligned with HIFU beam. Therefore, one could confirm that the HIFU beam was targeted at the region of interest using an image of the targeted organ (visualized on the ultrasound scanner).

Animal Protocols

Adult male Sprague-Dawley rats 8 to 12 weeks old (250-300 g; Charles River Laboratories) were housed at 25° C. on a 12-h light/dark cycle and acclimatized for 1 week before experiments were conducted. Water and regular rodent chow were available ad libitum.

Endotoxin (LPS from *Escherichia coli,* 0111: B4; Sigma-Aldrich) was used to produce a significant state of inflammation and metabolic dysfunction (e.g. hyperglycemia and hyperinsulemia) in naïve adult-Sprague Dawley rats. LPS was administered to animals (10 mg/kg; Rosa-Ballinas PNAS, 2008) via intraperitoneal (IP) injection causing significant elevation in TNF, circulating glucose and circulating insulin concentration which peaks 4-hours, but remains elevated as compared to control for up to 8 hours' post injection. Spleen, liver, hypothalamic, hippocampal and blood samples were harvested after 60 minutes (for power studies) and at 30, 60, 120, 240 or 480 minutes (for duration and kinetic studies) following LPS administration. Spleen and liver samples were homogenized in a solution of PBS, containing phosphatase (0.2 mM phenylmethylsulfonyl fluoride, 5 ug/mL of aprotinin, 1 mM benzamidine, 1 mM sodium orthovandate and 2 uM cantharidin) and protease (1 uL to 20 mg of tissue as per Roche Diagnostics) inhibitors. A targeted final concentration of 0.2 g tissue per mL PBS solution was applied in all samples. Blood samples were stored with the anti-coagulant (disodium) EDTA to prevent coagulation of samples. Samples were analyzed by ELISA assay for changes in cytokine (Bio-Plex Pro; Bio-Rad), TNF (Lifespan) and acetylcholine (Lifespan) concentration. Catecholamine concentrations were assessed using HPLC detection or ELISA (Rocky Mountain Diagnostic) analysis.

The effects of LPS on blood glucose and insulin levels were examined. Blood samples were obtained from the tail vein at 0, 60, 90, 120, 150, 180, and 240 min after LPS injection to measure glucose and insulin levels. Circulating blood glucose concentrations were measured by a OneTouch Elite glucometer (LifeScan; Johnson & Johnson). Insulin concentrations in plasma, obtained from blood, were determined using an ELISA kit (Crystal Chem, Chicago, IL) to determine the impact of LPS and subsequent ultrasound stimuli on systemic insulin resistance. Signal transduction changes were measured by assessment of biomarkers including: p38, p7056k, Akt, GSK3B, c-Src, NF-κβ, SOCS3, IRS-1, NPY, and POMC in liver, muscle, cardiac and hypothalamic tissue samples. The induced changes caused by ultrasound stimulation may include insulin-mediated glucose uptake as well as changes in associated molecules associated with inhibition/activity in metabolic activity.

The protocol used for ultrasound neuromodulation may be as follows:

Animals may be anesthetized with 2-4% isoflurane

The animal may be laid prone on a water circulating warming pad to prevent hyperthermia during the procedure.

The region above the targeted region of interest for ultrasound stimulus (nerve of interest) may be shaved with a disposable razor and animal clippers prior to stimulation.

Diagnostic imaging ultrasound may be used to spatially select the region of interest Liver: the porta hepatis as indicated by Doppler identification of the hepatic portal vein.

Spleen: visual identification of the spleen by diagnostic ultrasound. Location of stimuli may be maintained along the splenic axis as identified.

The area may be marked with a permanent marker for later identification.

Either the FUS ultrasound probe or LogiQ E9 probe may be placed at the designated region of interest previous identified by diagnostic ultrasound.

An ultrasound pulse may then be performed with total duration of a single stimulus not surpassing a single 1 minute pulse. At no point, energies would reach levels associated with thermal damage & ablation/cavitation (35 W/cm$^2$ for ablation/cavitation). That is, the temporal average intensity in the region of interest, in certain embodiments, is less than 35 W/cm$^2$.

LPS (10 mg/kg may then be injected intraperitoneal (for acute/kinetic studies). Alternatively, for duration of effect, LPS may not be injected here and may instead be injected at a later designated time point.

A second 1 minute ultrasound stimuli may be applied.

The animal may then be allowed to incubate under anesthesia for acute (1 hour) and kinetic (varying up to a maximum of 3 hours post LPS) studies. After which the animal is sacked and tissue, blood samples are collected.

For duration of effect studies, LPS is not injected at the time of ultrasound stimulus but rather at a designated time point after the ultrasound stimuli has been applied (e.g. 0.5, 1, 2, 4 or 8 hours). After which the animal is placed into an anesthetic holding chamber and monitored up until euthanasia and tissue/fluid collection.

An incision may be made starting at the base of the peritoneal cavity extending up and through to the pleural cavity. Organs may be rapidly removed and homogenized in a solution of PBS, containing phosphatase (0.2 mM phenyl-methylsulfonyl fluoride, 5 ug/mL of aprotinin, 1 mM benzamidine, 1 mM sodium orthovandate and 2 uM canthari-din) and protease (1 uL to 20 mg of tissue as per Roche Diagnostics) inhibitors. A targeted final concentration of 0.2 g tissue per mL PBS solution was applied in all samples. Blood samples were stored with the anti-coagulant (disodium) EDTA to prevent coagulation of samples. Samples are then stored at −80° C. until analysis. Samples were analyzed by ELISA assay for changes in cytokine (Bio-Plex Pro; Bio-Rad), TNF (Lifespan/Abcam/ThermoFisher) and acetylcholine (Lifespan) concentration.

Catecholamine concentrations were assessed using HPLC detection or ELISA (Rocky Mountain Diagnostic) analysis.

Electrode-based Vagal Nerve Stimulation Control Experimental Protocol

Male Sprague-Dawley rats were anesthetized with 2% isoflurane. A single incision was made along the neck exposing the cervical portion of the trapezius, sternocleido-mastoid and muscles for blunt dissection exposing the left cervical vagus nerve. The microelectrode was placed along the main trunk of the exposed cervical vagus nerve. Electrical stimulation (5V, 30 Hz, 2 ms; 5V, 5 Hz, 2 ms; 1V, 5 Hz, 2 ms) was generated using a BIOPAC MP150 module under the control of the of the AcqKnowledge software (Biopac Systems). Rats underwent 3 min of vagus nerve stimulation before and after IP injection of 10 mg/kg LPS. Rats were euthanized 60 min after LPS injection, and spleen and blood samples were obtained for TNF determination. In rats subjected to sham surgery, the vagus nerve was exposed, but not touched or manipulated.

HPLC Analyses

Serum samples were injected directly into the machine with no pre-treatment. Tissue homogenates were initially homogenized with 0.1M perchloric acid and centrifuged for 15 minutes, after which the supernatant was separated and the sample injected into the HPLC (Dhir & Kulkarni, 2007).

Catecholamines (Norepinephrine/Epinephrine) were analyzed by high performance liquid chromatograph (HPLC) with inline ultraviolet detector. The test column used in this analysis was a Supelco Discovery C18 (15 cm×4.6 mm I.D., 5 um particle size). A biphasic mobile phase comprised of [A] acetonitrile: [B] 50 mM KH2PO4, set to pH 3 (with phosphoric acid). The solution was then buffered with 100 mg/L EDTA and 200 mg/L 1-octane-sulfonic acid. Final concentration of mobile phase mixture was set at 5:95, A:B. A flow rate of 1 mL/min was used to improve overall peak resolution while the column was held to a consistent 20° C. to minimize pressure compaction of the column resulting from the viscosity of the utilized mobile phase. The UV detector was maintained at 254 nm, a wavelength known to capture the absorption for catecholamines including: nor-epinephrine, epinephrine and dopamine.

Chemical Inhibition of ultrasound Modulated Molecular Signaling Pathways

To further investigate the impact of mechanical vs. direct neural stimulation (and preferential modulation of nerve versus non-neural components of the axoextracellular synapse), a SRC inhibitor (common marker of direct mechanoreceptor) or PI3K inhibitor (common marker of neural signal transduction) prior to performing the ultrasound stimulation procedure outlined above.

Tissue Extraction and Paraffin Block Conversion:

Put tissue (Rat brain) into fixative immediately and fix ~24 hours in 10% formalin at 4° C.

Process tissue with the following protocol (with vacuum and pressure during each incubation):

a. 70% ethanol, 37° C., 40 min
b. 80% ethanol, 37° C., 40 min
c. 95% ethanol, 37° C., 40 min
d. 95% ethanol, 37° C., 40 min
e. 100% ethanol, 37° C., 40 min
f. 100% ethanol, 37° C., 40 min
g. Xylene, 37° C., 40 min
h. Xylene, 37° C., 40 min
i. Paraffin, 65° C., 40 min
j. Paraffin, 65° C., 40 min
k. Paraffin, 65° C., 40 min
l. Paraffin, 65° C., 40 min *leave in this paraffin until ready for embedding, however don't go more than ~12-18 hours.

Embed into Paraffin block for sectioning, allow block to cool/harden before sectioning. Section 5 micron thick, float on 50° C. water bath for collection. Use positive charged slides and try to position the tissue in the same orientation for every slide. Air dry slides. Overnight at room temperature seems to be the best for drying but the slides can place on a 40° C. slide warmer to speed up the drying process, but don't leave slides more than an hour on the warmer. Store slides at 4° C.

IHC Process

Formalin-fixed paraffin-embedded (FFPE) tissue samples (Rat brains) were baked at 65° C. for 1 h. Slides were deparaffinized with xylene, rehydrated by decreasing ethanol concentration washes, and then processed for antigen retrieval. A two-step antigen retrieval method was developed specifically for multiplexing with FFPE tissues, which allowed for the use of antibodies with different antigen retrieval conditions to be used together on the same samples. Samples were then incubated in PBS with 0.3% Triton X-100 for 10 min at ambient temperature before blocking against nonspecific binding with 10% (wt/vol) donkey serum and 3% (wt/vol) BSA in 1×PBS for 45 min at room temperature. Primary antibody cFOS (santa cruz-SC52) was diluted to optimized concentration (5 ug/mL) and applied for 1 h at room temperature in PBS/3% (vol/vol) BSA. Samples were then washed sequentially in PBS, PBS-TritonX-100, and then PBS again for 10 min, each with agitation. In the case of secondary antibody detection, samples were incubated with primary antibody species-specific secondary Donkey IgG conjugated to either Cy3 or Cy5. Slides were then washed as above and stained in DAPI (10 ug/mL) for 5 min, rinsed again in PBS, then mounted with antifade media for Image acquisition. Whole tissue mages were acquired on fluorescence Olympus IX81 microscope at 10× magnification.

Image Processing

Autofluorescence (AF), which is typical of FFPE tissues, should be characterized and separated from target fluorophore signals using autofluorescence removal processes, wherein an image of the unstained sample is acquired in addition to the stained image. The unstained and stained images are normalized with respect to their exposure times and the dark pixel value (pixel intensity value at zero exposure time). Each normalized autofluorescence image is then subtracted from the corresponding normalized stained image. AF removed image merged with registered 4',6-diamidino-2-phenylindole (DAPI) image is. The same region of interest in stimulated and control samples were imaged and images were qualitatively assessed for cFOS expression to detect changes nerve activation associated gene expression.

Histology assessment of spleen: Spleen from stimulated rats and control rats were processed into paraffin blocks as described above. Paraffin embedded sections were cleared and stained for H&E following standard protocol reported in the literature and scanned on bright field Olympus scanner. H&E images were qualitatively assessed for morphology difference and no significant difference noticed between stimulated and control samples.

Heart Rate Monitoring and Analysis

Heart rate (during either ultrasound or electrode stimulation experiments) was monitored using a commercial infrared oximeter and physiological monitoring system (Starr Lifesciences) using manufacturer's instructions. During the stimulation protocols the foot clip sensor (provided by manufacturer) was placed on the footpad of the animal. The animal was allowed to acclimate for at least 5 minutes prior to measurement, a time point found sufficient for animals to recover to normal heart rate activities and physiological reading in controls. Measurement were recorded before (2 minute recording periods), during, and after the stimulation (2 minutes recording periods) with either the electrical microelectrode or ultrasound probe, respectively.

Diffusion Functional MRI Measurements of Ultrasound Induced Activation

Neuronal activation may be detected using blood-oxygenation-level-dependent (BOLD) fMRI; brain regions with increased metabolic demand lead to higher cerebral blood flow, an increased supply of oxygenated blood, and decreased gradient echo signal. Sensitivity to the BOLD effect requires the use of fast gradient echo acquisitions; this causes undesired signal loss in brain areas next to air pockets, such as sinuses and ear canals, and hinders detection of neuronal activation near those specific brain areas. Alternatively, to minimize signal loss in areas characterized by large field inhomogeneities, spin echo (or double spin echo) diffusion weighted imaging (DWI) may be used. In DWI-fMRI, a volume increase in the slow-diffusing, presumably intracellular, water pool, or an increase in water diffusion (or apparent diffusion coefficient (ADC)) were both assigned to cell swelling and membrane expansion caused by neuronal activation.

Figures 13, 14:
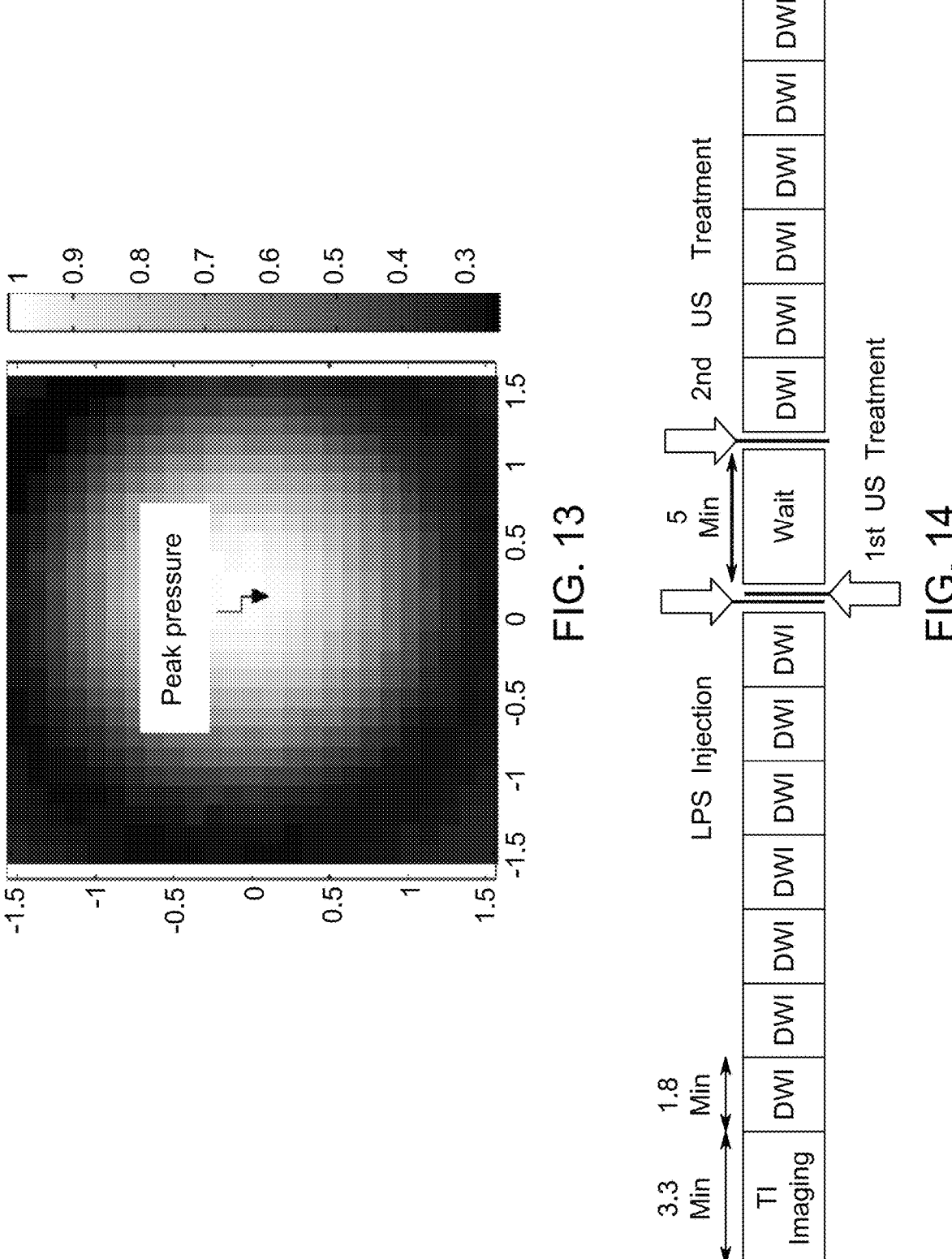
FIG. 13 shows an example of an ultrasound pressure field in x-y plane.
FIG. 14 shows experimental workflow for LPS injection for generating a model of inflammation and/or hyperglycemia/hyperinsulemia and ultrasound treatments.

Ten rats underwent a brain MRI scan using the paradigm of FIG. 14. Six of them received both the LPS injection (as described above) and the ultrasound treatment; four of them only received the LPS injection. Ten Sprague-Dawley rats were anesthetized using 3% Isoflurane and placed supine, with their heads inserted in a birdcage coil. The abdomen region was coupled through a gel/water filled cone to an MR-compatible ultrasound probe (f=1.47 MHz), focusing on the porta hepatis, a liver region previously containing glucose sensitive neurons.

Scans were performed in a 3T GE DV scanner (Waukesha, WI), using a Doty Scientific quadrature birdcage coil. The scans started with a T1 acquisition, using a spoiled gradient echo sequence, at a 0.4/1 mm in-plane/out-of-plane spatial resolution, using a TE/TR of 10/1475 ms, for a total acquisition time of 3:22 min. Six blocks of double spin echo diffusion weighted imaging (DWI) images (termed forward polarity gradient, or FPG) were acquired at 0.6/1 mm in-plane/out-of-plane spatial resolution, with a TE/TR of 82/3400 ms, using ¾ averages for the b=0/b=1000 s/mm², respectively, for a total acquisition time per block of 1:49 min. At the completion of the 6 pre-injection DWI acquisition, for distortion correction purposes, another DWI acquisition was performed, with the direction of the gradients reversed; this acquisition is referred to as a reverse polarity gradient (RPG) acquisition. Following the LPS injection, the 1st ultrasound treatment, a wait time of 5 minutes, and the second ultrasound treatment, other 6 blocks of FPG DWI images were acquired. For the control rats, only undergoing the LPS injection, the last 6 DWI blocks immediately followed the LPS injection.

The ultrasound treatment was performed using a MR compatible 1.47 MHz focused ultrasound transducer, coupled to the region of interest (e.g., gastrointestinal tissue, pancreas, liver, etc.) using a water-filled cone. Each ultrasound treatment lasted 60 seconds, during which pulsed sinusoidal ultrasound waveforms were applied. The pulse on time was 150 us and the pulse off-time was 350 us. The rats' abdomens were outside of the imaging coil; supine animal positioning ensured easy coupling of the ultrasound probe to the liver through the skin, using coupling gel. A cross-correlation coefficient (ccc) between the T1 images and the (distortion-corrected) b=0 DWI images of at least 0.5 was used to identify slices to be used for further analysis. Apparent diffusion coefficient (ADC)s were calculated for the pre- and post-treatment images; pre- and post-treatment image data were pooled together for statistical analysis. A rigid registration between the T1 images and a rat atlas was used to determine regions in which pixel-by-pixel t-tests indicated significant changes. The registration transformation from the T1 and atlas images was applied to the distortion-corrected DWI and ADC images.

Cholinergic Anti-Inflammatory Pathway

The present examples demonstrate a noninvasive method to stimulate specific axonal projections within organs using ultrasound energy application to achieve the simulation and associated physiological outcomes. Ultrasound was first applied to the spleen and found to stimulate the axons associated with the cholinergic anti-inflammatory pathway (CAP) to modulate systemic cytokine concentrations. When this pathway was chemically or mechanically blocked, the ultrasound-induced effect was suppressed. When ultrasound parameters were varied, extracellular neurotransmitter concentrations, intracellular kinase activity, and CAP-related cytokines were affected differently, demonstrating the capability to produce a desired physiological response by modifying ultrasound parameters. Next, hepatic ultrasound stimulation was shown to modulate sensory pathways that regulate blood glucose, and this effect was found to depend on stimulation of a specific anatomical site within the liver. Collectively, these data demonstrate that ultrasound neuromodulation within organs could offer a method for precision neuromodulation that facilitates stimulating small subsets of neurons within an organ or tissue to affect specific physiological functions, e.g., modulation of blood glucose (via liver neuromodulation) and systemic cytokines (via splenic neuromodulation).

Figure 15A:
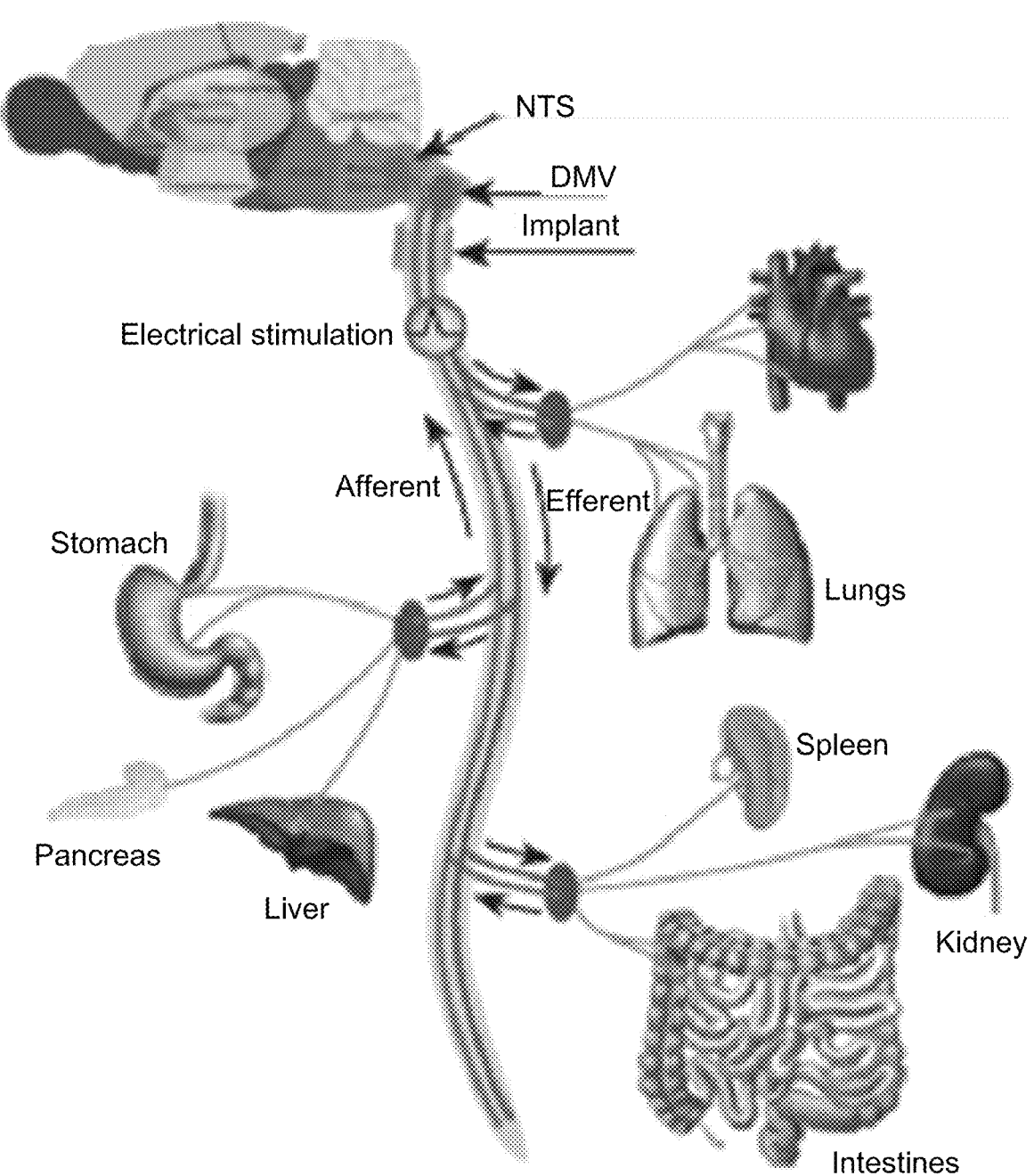
FIG. 15A is a schematic illustration of broad vagus nerve stimulation.

Within peripheral nerves, individual axons are tightly bundled in groups (fascicles) and wrapped within protective tissue. This makes it difficult to selectively stimulate subsets of axons that terminate in specific organs and uniquely modulate the function of communicating cells within that organ. Clinical implementation of precision peripheral nerve stimulation remains complex. FIG. 15A shows a partial schematic of the complex system of projecting efferent and afferent neurons within the vagus nerve, exemplary innervated organs, and the approximate position for stimulators used for cervical VNS. Efferent neurons originate from the dorsal motor nucleus of the vagus nerve (DMV) and afferent neurons enter the brain through the nucleus tractus solitarii (NTS). Peripheral nerves leading to visceral organs contain both efferent and afferent neurons, which are difficult to stimulate in isolation using distal cervical VNS implants.

Figure 15B:
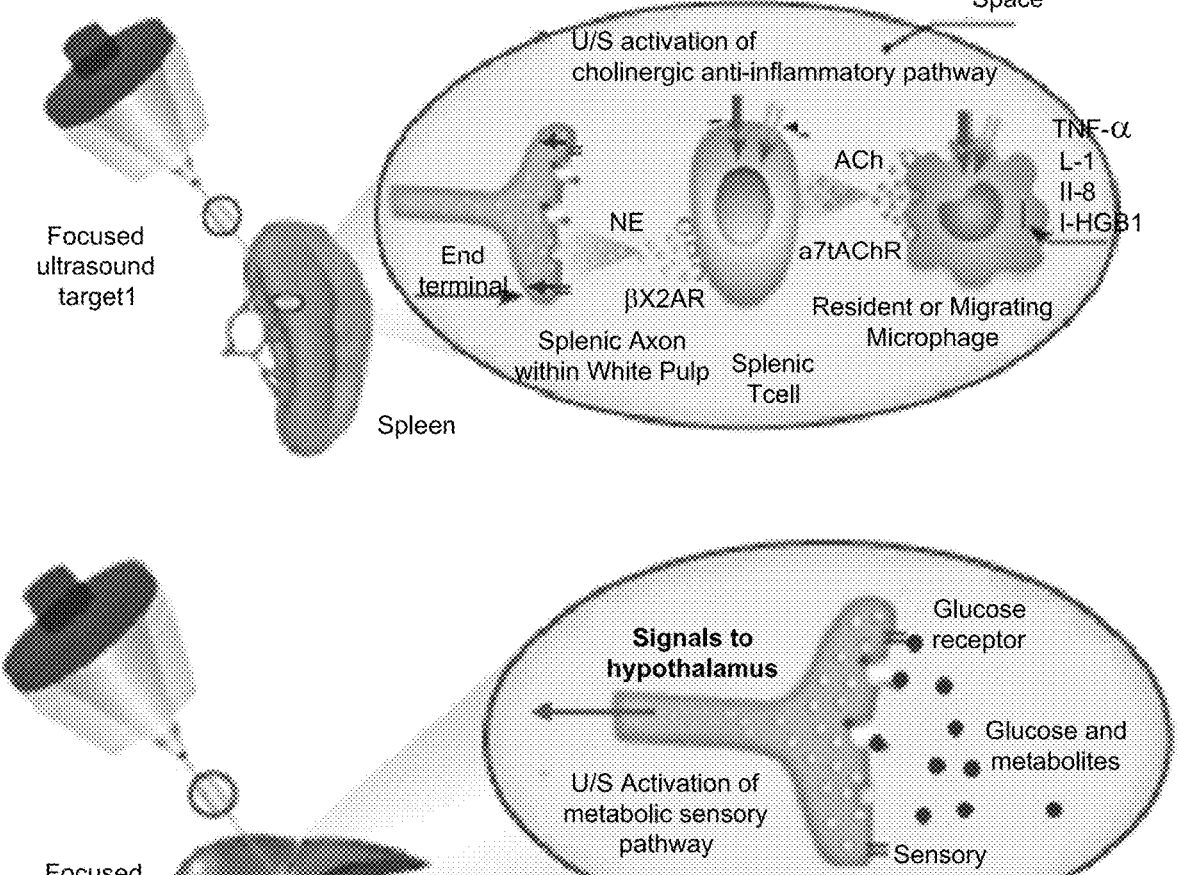
FIG. 15B is a schematic illustration of targeted organ-based peripheral neuromodulation.

FIG. 15B is a descriptive schematic of targeted organ-based peripheral neuromodulation, in which subsets of axons that terminate within organs are preferentially stimulated using focused pulsed ultrasound. Targets investigated herein include axon terminals within the spleen associated with the cholinergic anti-inflammatory pathway and sensory terminals within the liver associated with communicating metabolic information to the brain to aid in maintenance of glucose homeostasis. Focused pulsed ultrasound as provided herein stimulates axonal subsets terminating within organs (FIG. 15B). In certain examples provided herein, ultrasound energy was focused on axonal projections within the spleen (to affect systemic inflammation through the cholinergic anti-inflammatory pathway (CAP)) and liver (to communicate metabolic information to the brain and maintain glucose homeostasis).

Figure 16A:
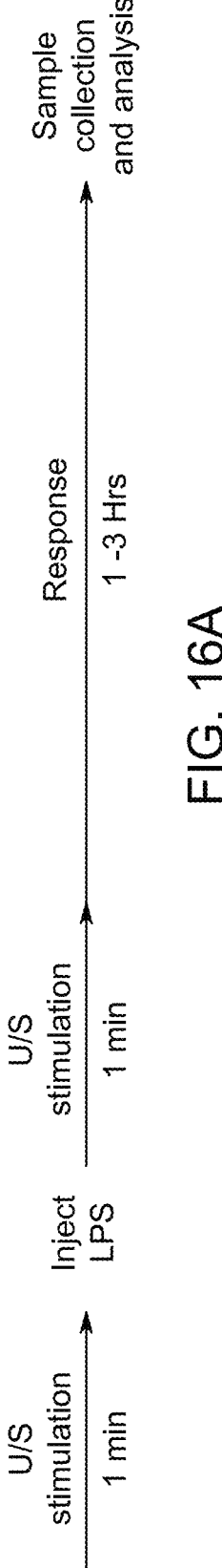
FIG. 16A is an experimental timeline of ultrasound energy application to a rat spleen.

Each cell type involved in the CAP was monitored under different ultrasound stimulation parameters in the rodent LPS-induced inflammation model (FIGS. 16A and B; The CAP (FIG. 15B) consists of three major cell types: the post-synaptic end axon terminals projecting from the splenic ganglia, intermediary T-cells, and macrophages that modulate circulating cytokine levels. CAP response to local ultrasound stimulation was monitored by measuring splenic concentrations of CAP-related neurotransmitters and cytokines including norepinephrine (NE), acetylcholine (ACh), and tumor necrosis factor (TNF-α).

Ultrasound stimulation was performed as provided herein and according to the timeline shown in FIG. 16A to show induced targeted physiological outcomes relative to control. One-minute ultrasound stimuli were given before and after an LPS injection; samples were collected and the induced changes caused in local (i.e., tissue) and systemic neurotransmitter and cytokines were measured (FIGS. 16B-E) to demonstrate the effect of ultrasound-induced CAP neuromodulation on the response to the LPS model. The response time was 1 hour for all data, except FIG. 16E. However, it should be understood that the depicted response time is by way of example only. That is, the inducement of changes as a result of neuromodulation at a region of interest may be within an hour and, in some embodiments, may persist for several hours or days. Accordingly, as provided herein, assessment of measurable induced changes induced by neuromodulation may occur at baseline (at or before neuromodulation) and at one or more time points (at minute intervals, at hour intervals, at day intervals) after neuromodulation. Certain subjects may be continuously or intermittently monitored to assess the concentration of one or more molecules or interest (or other measurable effects, such as organ displacement) as part of a treatment protocol.

Figure 16B:
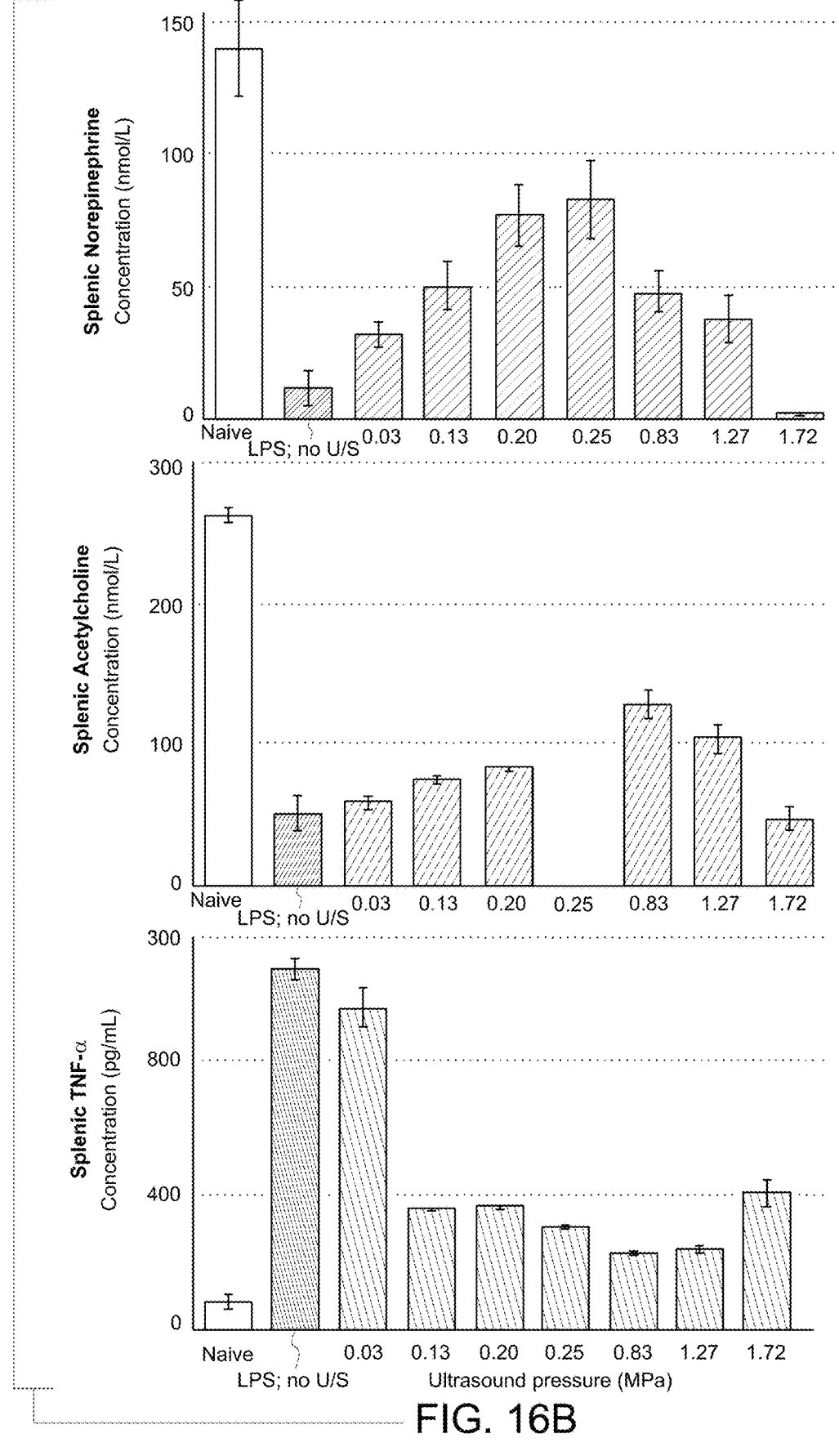
FIG. 16B shows splenic norepinephrine, acetylcholine, and TNF-α at different applied ultrasound energy levels to the rat spleen, shown as ultrasound pressure MPa.

Sham controls were performed by placing the ultrasound transducer on the targeted organ, but not applying the ultrasound stimulus. FIG. 16B shows the measured CAP response in naïve rats, sham controls (rats that received LPS but not ultrasound stimulation), and in animals that received LPS with various ultrasound stimulation pressures. Concentrations of norepinephrine (i), acetylcholine (ii), and TNF-α (iii) are shown for naïve animals, sham controls, and for animals with ultrasound stimulation pressures from 0.03-1.72 MPa. Note that the x-axis labels denoting naïve animals, sham controls, and ultrasound stimulation pressures in (iii) apply to all three graphs Splenic norepinephrine levels averaged 140 nmol/L in naïve animals, whereas the LPS-induced inflammation dropped norepinephrine levels to near zero, demonstrating suppression of CAP signaling at initial inflammation.

Figure 16C:
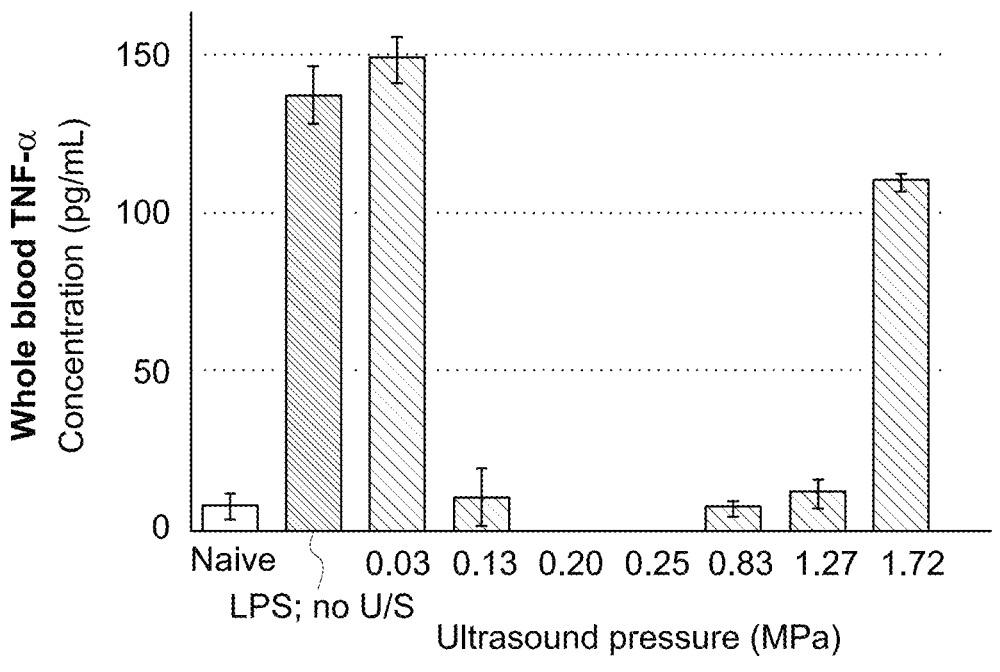
FIG. 16C shows circulating concentrations of TNF-α for the same conditions as FIG. 16B.
Figure 16D:
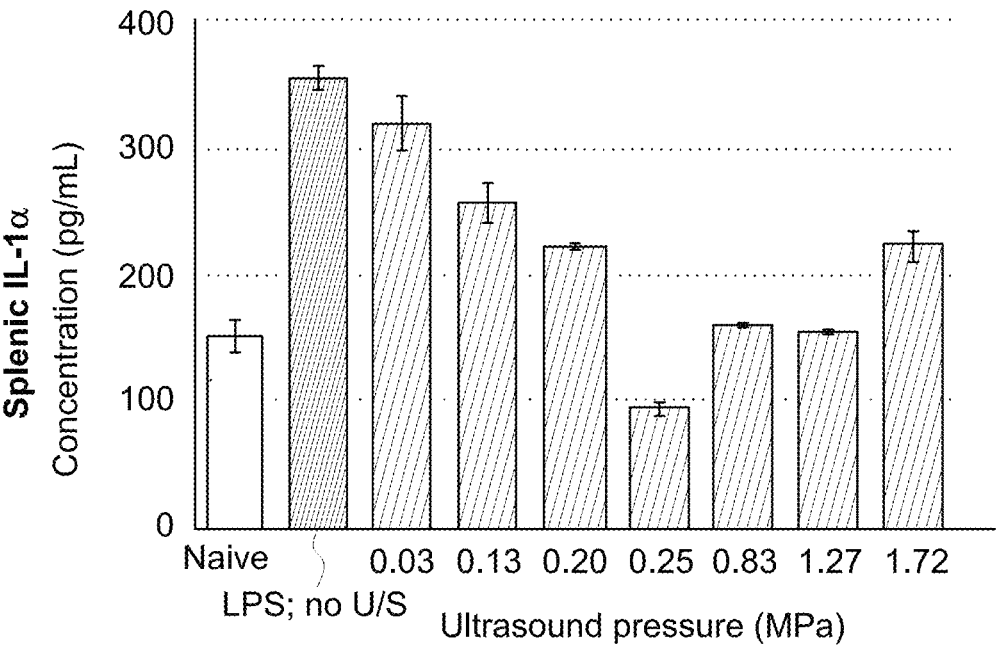
FIG. 16D shows splenic IL-1α concentrations for the same conditions as FIG. 16B.
Figure 16E:
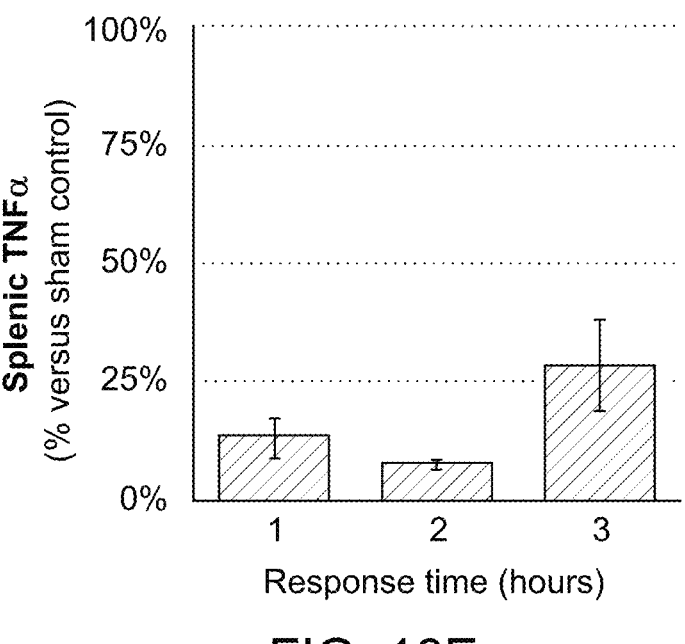
FIG. 16E shows response time for induced changes in splenic TNFα concentrations relative to control.

As shown, the ultrasound stimulus attenuated the LPS response toward levels measured in naïve animals (FIG. 16B.i.) Consistent with the CAP signaling process, the norepinephrine increase in the ultrasound-stimulated animals correlated with a splenic acetylcholine increase; at 0.83 MPa ultrasound pressure the average acetylcholine concentration was nearly three times that found in the sham animals (FIG. 16B.ii). FIG. 16C shows circulating concentrations of TNF-α for the same conditions as FIG. 16B. Note that the x-axis labels denoting naïve animals, sham controls, and ultrasound stimulation pressures in FIG. 16C apply to FIG. 16B as well. FIG. 16D shows splenic IL-la concentrations for the same conditions as FIG. 16B. Both splenic (FIG. 16B.iii) and circulating TNF-α (FIG. 16C) levels were significantly reduced compared to the sham animals. The response to treatment depended on ultrasound pressure (0.83 MPa was used in subsequent experiments). As additional evidence that splenic ultrasound stimulation specifically caused changes in the CAP, figure FIG. 16D shows that ultrasound stimulation affected concentrations of other proteins regulated by TNF-α-specific pathways, e.g., interlukin-1-alpha (IL-1α). Accordingly, the data demonstrate that controlling adjustable modulation parameters, such as ultrasound pressure, achieves targeted control of concentrations of molecules of interest. By varying the applied ultrasound pressure to the region of interest, the desired physiological outcomes (e.g., desired concentration changes in one or more molecules of interest) may be achieved. While the applied pressures may be determined empirically on a patient to patient basis, in some embodiments, ultrasound stimulation pressures from 0.03-1.72 MPa are used for the targeted neuromodulation. As provided herein, the ultrasound pressure may be a modulation parameter that is varied or adjusted as provided herein to achieve the targeted physiological response. Other adjustable parameters may be a treatment timeline (e.g., a duration of treatments, a separation between treatments, and a delay time for other clinical events or assessment via an assessment device).

Figure 16F:
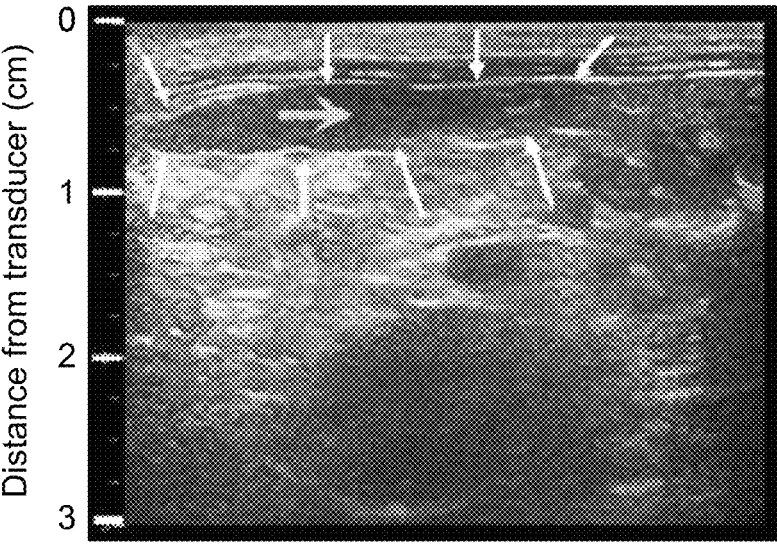
FIG. 16F shows a 2D ultrasound image of the rat spleen used to focus the ultrasound stimulus to spatially select the splenic target.
Figure 16G:
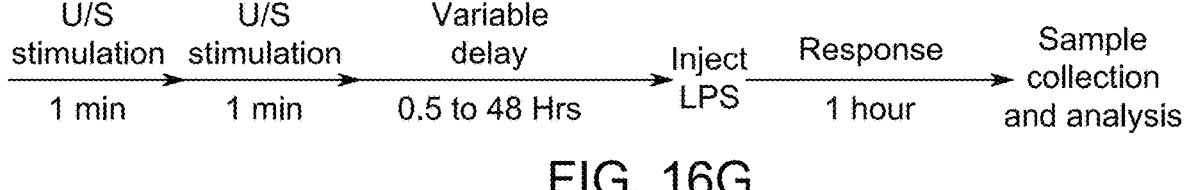
FIG. 16G shows the timeline of a study designed to measure the duration of effect of the stimulus on cholinergic anti-inflammatory pathway activation.
Figure 16H:
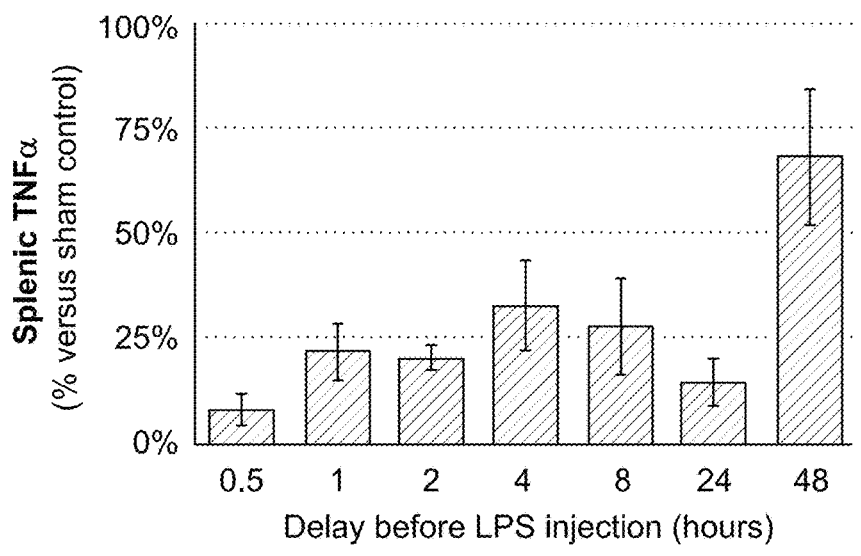
FIG. 16H shows the concentration of splenic TNF-α after protective ultrasound treatments.
Figure 16I:
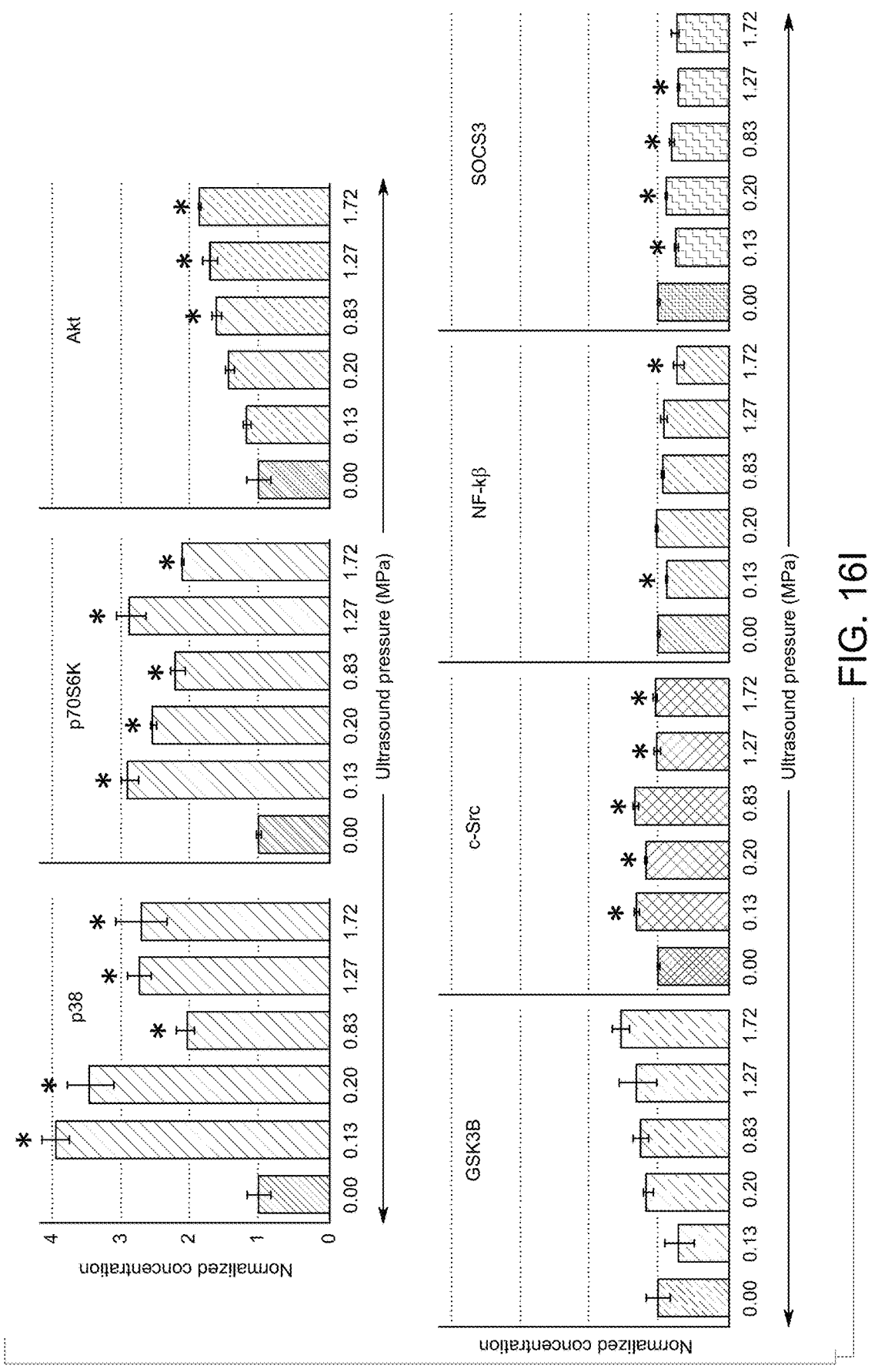
FIG. 16I shows the concentrations of activated/phosphorylated kinases as a result of splenic ultrasound modulation.

FIG. 16F shows a 2D ultrasound image of the rat spleen used to spatially select and focus the ultrasound stimulus to the splenic target shown with arrows to indicate an outline of the spleen and a targeted focal point (i.e., the region of interest of the spleen) for ultrasound stimulation. FIG. 16G shows a non-limiting embodiment of the timeline of a study designed to measure the duration of effect of the stimulus on CAP activation. In this study, the ultrasound stimulus was applied prior to the LPS injection and the delay time between the ultrasound stimulation and the LPS injection varied from 0.5 to 48 hours. FIG. 16H shows the concentration of splenic TNF-α, as a percentage (%) value of splenic TNF-α concentration measured in the sham control, after ultrasound treatments (i.e. ultrasound stimulus made prior to LPS injection) after variable delay times from 0.5 to 48 hours. FIG. 16I shows the concentrations of activated and/or phosphorylated kinases (p38, p70S6K, Akt, GSK3B, c-SRC, NF-κβ, SOCS3) with (shaded bars) or without (solid bars) ultrasound stimulation at ultrasound stimulus pressures ranging from 0.13-1.72 MPa.

A peak ultrasound-mediated response occurred 1-2 hours after treatment (FIG. 16E), similar to previous implant-based-VNS studies. Furthermore, splenic ultrasound may be provided to achieve a protective effect, when applied before the LPS injection (FIGS. 16G and 16H), also consistent with previous invasive VNS studies. FIG. 16H shows that the protective effect continued for 48 hours after treatment. To further characterize the protective effect, ultrasound activation of specific intracellular kinases were measured (FIG. 16I) that are associated with LPS, CAP or TNF-α-mediated signaling. These data show that ultrasound strongly enhanced activation of some kinases (e.g., p38 and p70S6K), and the ultrasound pressure-dependent response of some kinases (e.g. p38) roughly correlated with the ultrasound pressure dependence previously observed (FIG. 16B-D).

Figure 16J:
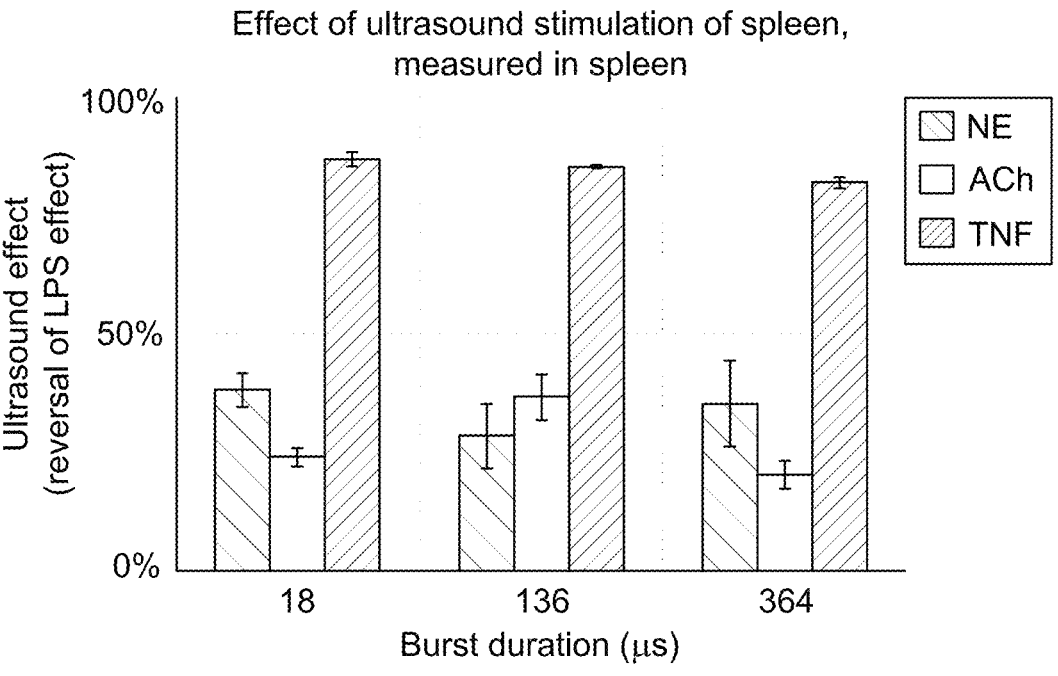
FIG. 16J shows example ultrasound burst durations and the effects on norepinephrine (NE), acetylcholine (ACh), and tissue necrosis factor alpha (TNF-α) concentrations in ultrasound-stimulated spleens (after LPS injection) using alternative ultrasound-stimulation parameters.
Figure 16K:
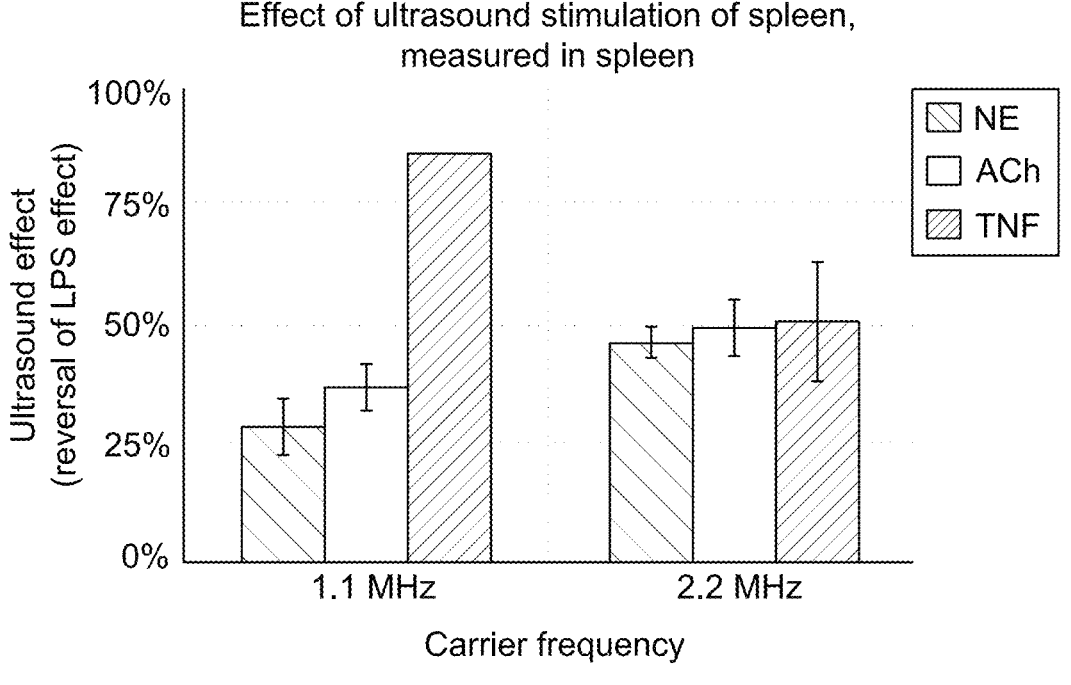
FIG. 16K shows example ultrasound carrier frequencies and the effects on norepinephrine (NE), acetylcholine (ACh), and tissue necrosis factor alpha (TNF-α) concentrations in ultrasound-stimulated spleens (after LPS injection) using alternative ultrasound-stimulation parameters.

FIGS. 16J and 16K show data for norepinephrine (NE), acetylcholine (ACh), and tissue necrosis factor alpha (TNF-α) concentrations in ultrasound-stimulated spleens (after LPS injection) using alternative ultrasound-stimulation parameters for burst durations and carrier frequencies. Data are shown in comparison to 0.83 MPa data of FIG. 16B in spleen samples taken after stimulation with alternative burst durations (left) or ultrasound carrier frequency (right).

Figure 17A:
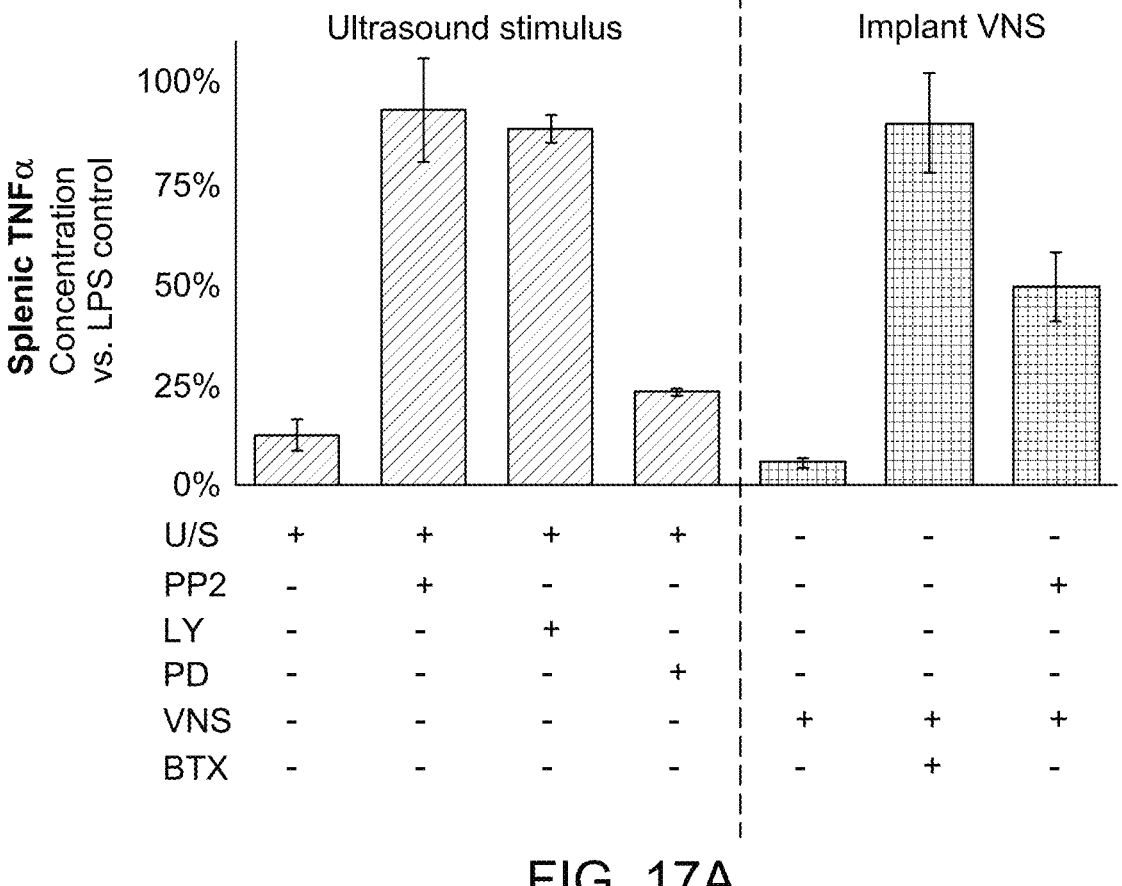
FIG. 17A shows the effect of splenic ultrasound modulation compared to standard electrode or implant-based vagal nerve stimulation (VNS) on splenic TNF-α and in the presence of various inhibitors.
Figure 17B:
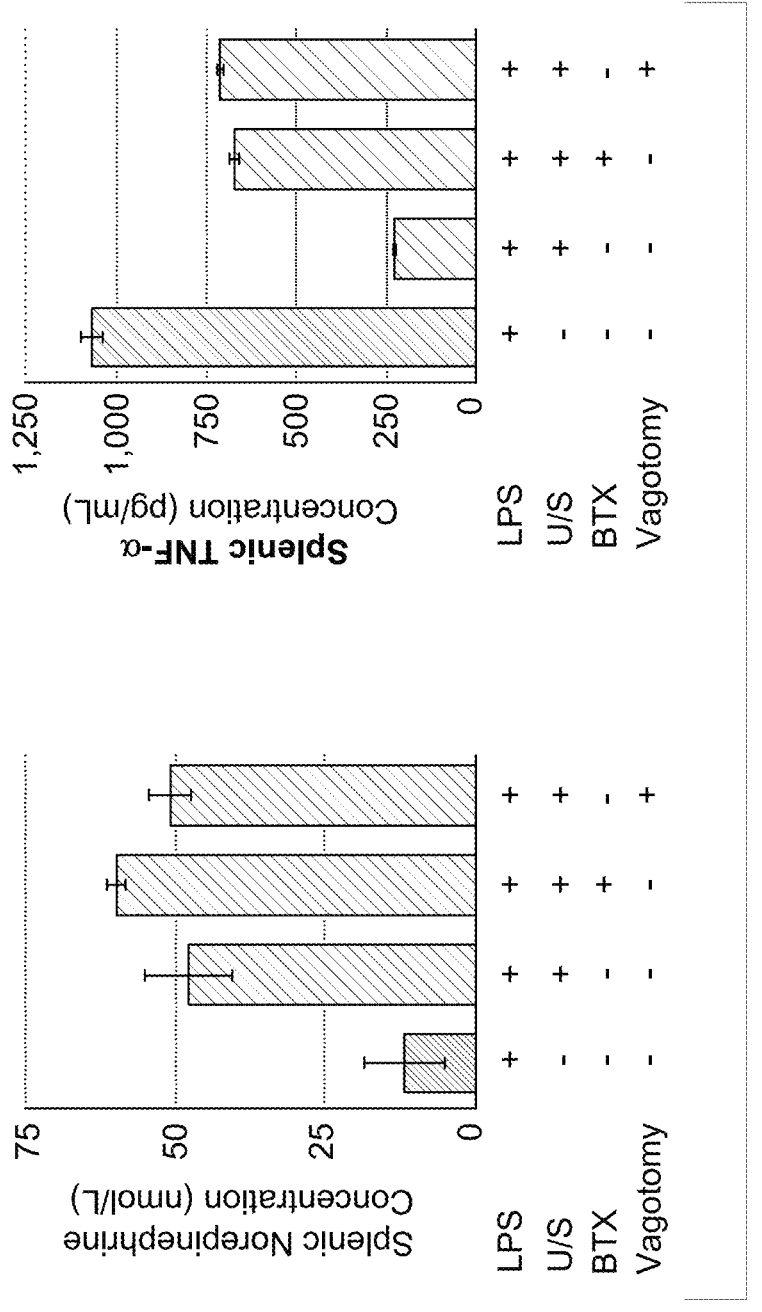
FIG. 17B shows the effect of α-bungarotoxin on splenic concentrations of (left) norepinephrine (NE) and (right) TNF-α after ultrasound stimulation of LPS-treated rodents with and without the effects of BTX or a surgical vagotomy.

The effect of splenic ultrasound modulation was compared to standard electrode or implant-based vagal nerve stimulation (VNS), which was performed as provided herein. In the FIGS. 17A and 17B, "+" is indicative of a present of the indicated event or inhibitor and "−" is indicative of the absence of the indicated event or inhibitor. In FIG. 17A, the X-axis represents induced changes in a rat spleen at different conditions (ultrasound vs. VNS and with different inhibitors) and the Y-axis shows relative concentrations of splenic TNF-$\alpha$ (versus LPS-treated controls) as a percent changes. The relative concentrations are shown for ultrasound stimulation (with ultrasound stimulus pressure of 0.83 MPa), and VNS stimulation with and without PP2 (partially selective Src kinase inhibitor), LY294002 (PI3-kinase selective inhibitor), PD98059 (MEK1 and MEK2 selective MAPK selective inhibitor), and $\alpha$-bungarotoxin (BTX; a known antagonist for $\alpha$7nAChR in the CAP pathway). FIG. 17B shows the effect of BTX on splenic concentrations of (left) norepinephrine (NE) and (right) TNF-$\alpha$ after ultrasound stimulation of LPS-treated rodents with and without the effects of BTX or a surgical vagotomy. FIG. 17A shows that invasive cervical VNS and noninvasive splenic ultrasound stimulation have a nearly equivalent effect on TNF-$\alpha$ production. Furthermore, FIG. 17B shows that splenic injection of $\alpha$-bungarotoxin (BTX; known antagonist for $\alpha$7nAChR) suppressed the effect of ultrasound stimulation on TNF-$\alpha$ concentration, demonstrating that (like VNS-based CAP activation) desired CAP modulation by ultrasound involves splenic $\alpha$7nAChR signaling. Consistent with the CAP model (FIG. 15B), NE concentration was unaffected by BTX (i.e. BTX blocked the effect of elevated NE through the $\alpha$7nAChR pathway). Vagotomy also suppressed CAP modulation by ultrasound, providing additional evidence that the ultrasound effect on CAP is nerve mediated (FIG. 17B). Finally, the kinase inhibitors PP2 (partially selective for Src kinase) and LY294002 (PI3-kinase selective) were shown to suppress the ultrasound effect, while PD98059 (MEK1- and MEK2-selective MAPK inhibitor) showed no effect (FIG. 17A). These results corroborate those in FIG. 16I, in which ultrasound stimulation caused a change in kinase activation within the PI3 (i.e., Akt, P70S6K), c-Src, and p38-MAPK pathways, but not kinases involved in bacterial antigen response (i.e., NFKB, GSK3B). Such changes may be part of a desired characteristic profile that is achieved through targeted neuromodulation and that is indicative of a targeted physiological outcome.

Figure 17C:
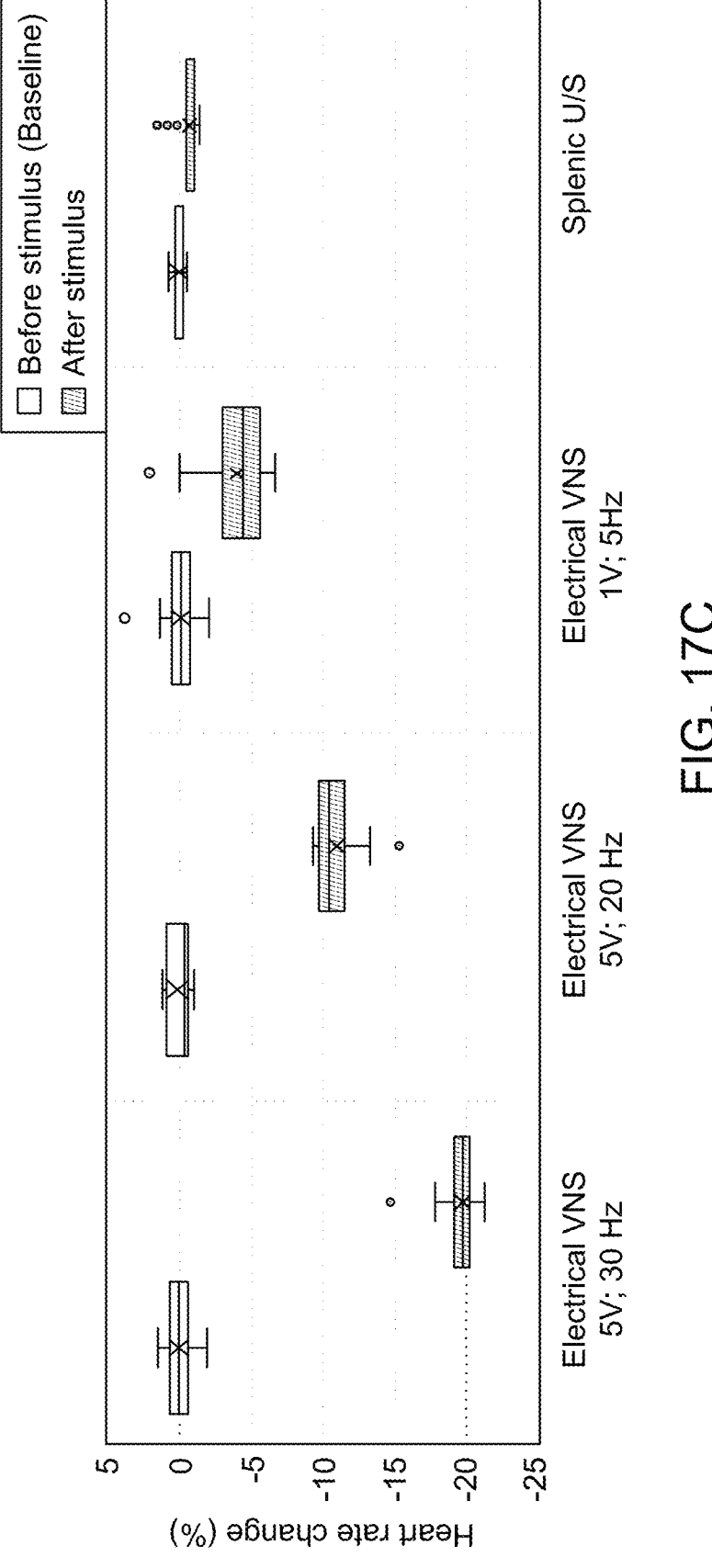
FIG. 17C shows data comparing the effect of VNS (at several stimulation intensities and frequencies) versus splenic ultrasound stimulation (at 0.83 MPa) on heart rate.

The physiological specificity of focused-ultrasound stimulation was examined by measuring several known side-effects of invasive VNS. FIG. 17C shows data comparing the effect of VNS (at several stimulation intensities and frequencies) versus splenic ultrasound stimulation (with ultrasound stimulus pressure of 0.83 MPa) on heart rate. FIG. 17C shows the change in heart rate caused by cervical VNS or splenic ultrasound stimulation. At 1 and 5 volt VNS intensities (known to activate CAP), heart rate significantly decreased. However, local splenic ultrasound stimulation showed no effect on heart rate.

Figure 17D:
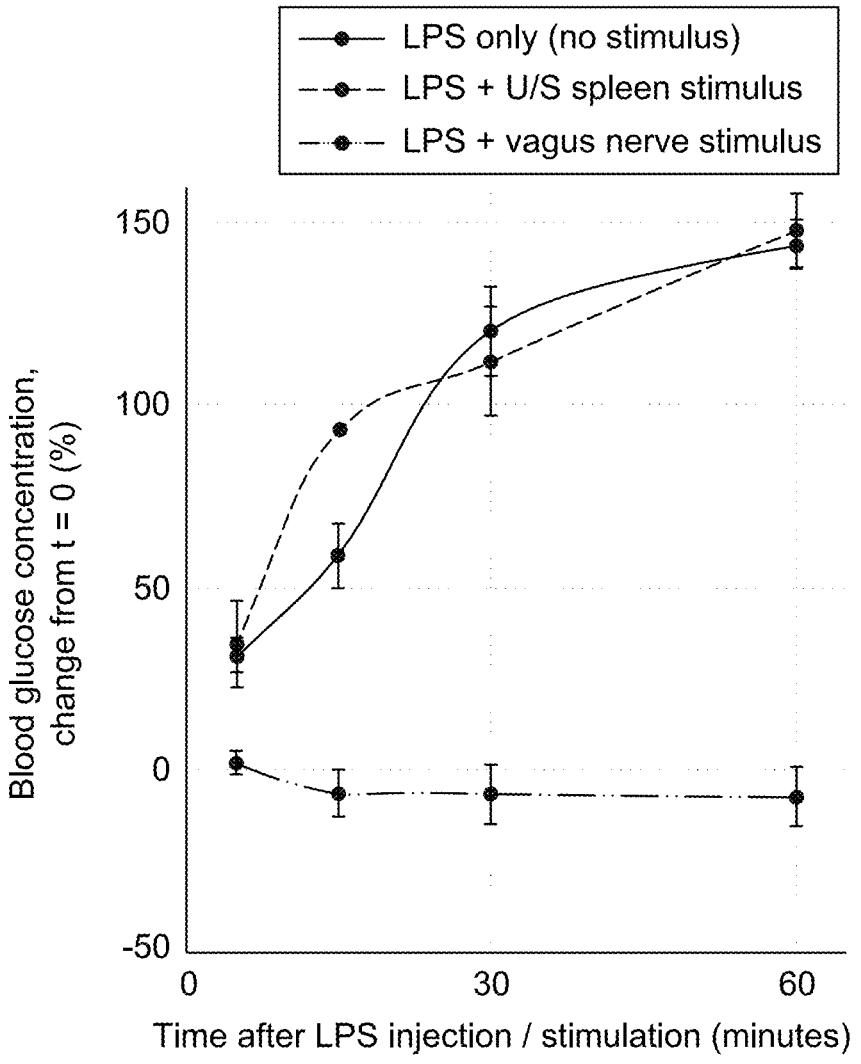
FIG. 17D shows data confirming the previously observed side effect of VNS on attenuation of LPS-induced hyperglycemia and absence of this side-effect when using splenic ultrasound stimulation.

FIG. 17D shows data confirming the previously observed side effect of VNS on attenuation of LPS-induced hyperglycemia and absence of this side-effect when using splenic ultrasound stimulation. The plot shows relative blood glucose concentrations (compared to pre-injection concentration) at times of 5, 15, 30, and 60 minutes after LPS injection for the LPS control (no ultrasound stimulus), or LPS-injection combined with splenic ultrasound stimulus or cervical VNS stimulation. FIG. 17D shows that ultrasound stimulation did not lead to changes in glucose concentration relative to the LPS only control, whereas VNS experiments exhibited the side-effect of attenuating hyperglycemia. This metabolic side-effect of CAP-targeted VNS may be due to off-target VNS of a second (non-CAP) vagal pathway. Such off-target effects are a result of the broader and less specific (i.e., less targeted) effects of VNS as compared to targeted peripheral neuromodulation as provided herein. A benefit of the targeted neuromodulation as provided is avoiding undesired off-target effects. The precision ultrasound stimulation technique was also used to investigate whether the VNS-mediated reduction in hyperglycemia was associated with direct stimulation of axons originating from metabolic sensory neurons.

In some embodiments, an ultrasound image may be used to guide the ultrasound stimulus to spatially select a region of interest for targeted delivery of ultrasound stimulus. As provided herein, spatial selection or spatially selecting may include obtaining an image of a tissue or organ (or a portion of a tissue or organ) and, based on image (e.g., the ultrasound image), identifying a region of interest within the organ. In some embodiments, the tissue or organ may have anatomical features that are used to guide the selection of the region of interest within the organ. Such features may, in some embodiments, include a site of blood vessel or nerve entry into an organ, a tissue type within an organ, an interior or edge of an organ, or a suborgan structure, by way of non-limiting example. In certain embodiments, the anatomical feature may include a liver porta hepatis, suborgans of a gastrointestinal tract (stomach, small intestines, large intestines), a pancreatic duct, or a splenic white pulp. By identifying the anatomical features in the image, the region of interest may be selected to overlap with or include the anatomical feature or be adjacent to the anatomical feature. In other embodiments, the anatomical feature may be excluded from the region of interest. For example, an intestinal tissue may be selected as a region of interest rather than a stomach tissue. The identification of the anatomical feature may be via morphological features that are visible in the image (e.g., visible in the ultrasound image) or by structure recognition features of the imaging modality used to obtain the image. As disclosed herein, the system 10 may be configured such that the energy application device 12 is configured to operate in an imaging mode to obtain the image and to subsequently operate in energy application mode after the image is obtained and the region of interest is spatially selected based on the image.

In other embodiments, the region of interest may be identified by the presence or absence of one or more biological markers. Such markers may be assessed by staining the organ or tissue and obtaining images indicative of the stain to identify regions of the organ or tissue that include the biological marker/s. In some embodiments, the biological marker information may be obtained by in vivo staining technologies to obtain location data of the biological marker/s in the tissue or organ specific for the subject in real time. In other embodiments, the biological marker information may be obtained by in vitro staining technologies to obtain location data for one or more representative images that is then used to predict the locations of the biological marker/s within the subject's tissue or organ. In some embodiments, the region of interest is selected to correspond with portion of the tissue or organ that are rich in a particular biological marker or that lack a particular biological marker. For example, the one or more biological markers may include markers for neuronal structures (e.g., myelin sheath markers).

The region of interest in the organ or tissue may be spatially selected based on operator input. For example, an operator may designate the region of interest on the obtained image by directly manipulating the image (i.e., drawing or writing the region of interest on the image) or by providing image coordinate information that corresponds to the region of interest. In another embodiment, the region of interest may be automatically selected based on the image data to achieve spatial selection. In some embodiments, the spatial selection includes storing data related to the region of interest in a memory and accessing the data.

Figure 18A:
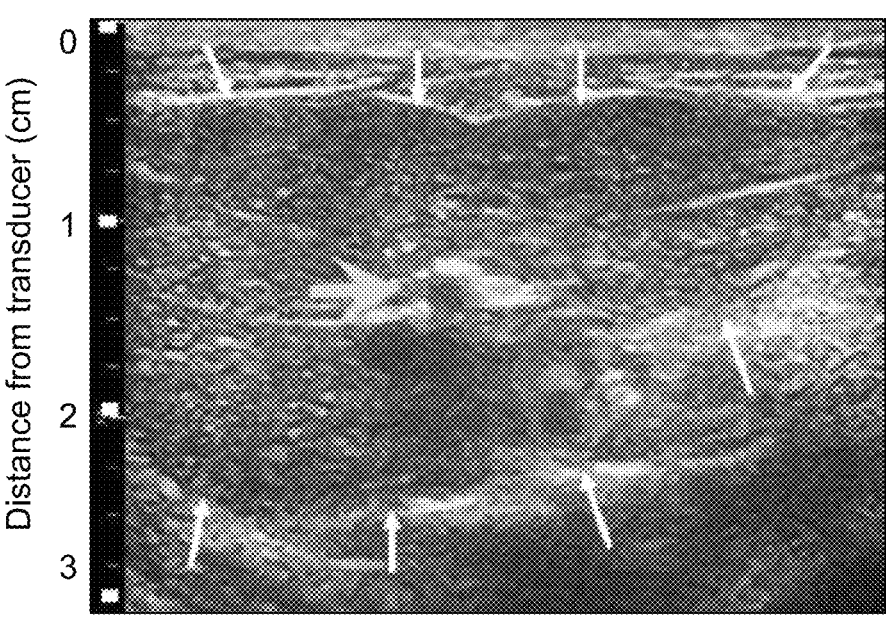
FIG. 18A is a 2D ultrasound image of the rat liver used to focus the ultrasound stimulus.

Once spatially selected, the system 10 is configured to apply energy to the region of interest as provided herein. For example, as illustrated in FIG. 18A, a 2D ultrasound image of a rat liver is used to guide the ultrasound stimulus to selectively focus on a target porta hepatis site, with white arrows indicating the outline of the liver and a center arrow indicating the region if interest. FIG. 18A shows that the ultrasound-image guidance enabled spatially selecting of a porta hepatis region of the liver and directing the ultrasound stimulus at the selected porta hepatis region, which contains glucose-sensitive neurons, for local targeted ultrasound neuromodulation.

Figure 18B:
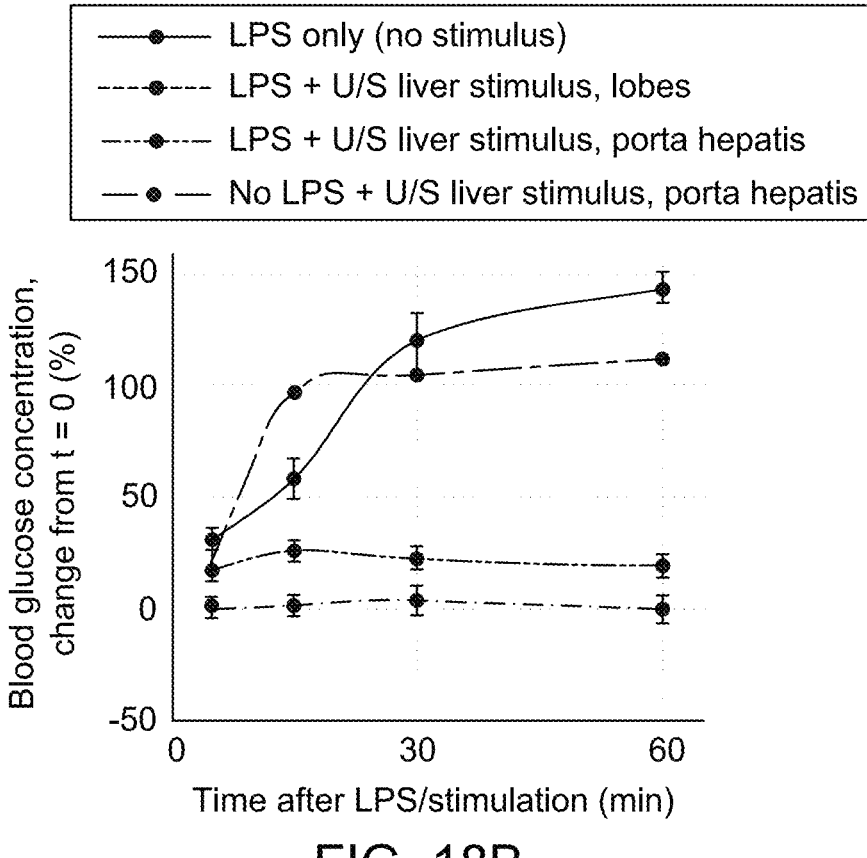
FIG. 18B shows the effect of ultrasound stimulation of the liver on LPS-induced hyperglycemia.

FIG. 18B provides a non-limiting example of selectively applying ultrasound stimulation on various regions of the liver of a LPS-induced hyperglycemia animal model to achieve targeted modulation of blood glucose concentration. The plot of FIG. 18B shows relative blood glucose concentrations (compared to pre-LPS injection concentration) at time points of 5, 15, 30, and 60 minutes after LPS injection. In a group that receives only LPS injection without ultrasound stimulus, LPS-induced hyperglycemia is observed. The data further shows that ultrasound stimulation of the distal lobes of the liver does not significantly affect the blood glucose concentration. In contrast, selectively applying ultrasound stimulation on the porta hepatis may be used to reverse LPS-induced hyperglycemia and modulate blood glucose concentration. Accordingly, the site of the region of interest yields different results, and a broad or untargeted liver treatment to the lobes would not achieve the same targeted effects as ultrasound treatment targeting (using a region of interest adjacent to or including) the porta hepatis region. As shown in the embodiment of FIG. 18B, applying ultrasound stimulation to a region of interest in liver, in accordance with the protocol as shown in FIG. 16G, provides protection against LPS-induced hyperglycemia of the model and limits and/or controls the increase of blood glucose concentration and modulates the concentration to below post-prandial concentrations. Furthermore, the modulation may be anatomically specific. FIG. 18B shows that directing the ultrasound stimulus toward the right or left lobe of the liver attenuated the ultrasound-induced effect on blood glucose. That is, not all areas of the liver responded in the same manner to ultrasound energy application. In some embodiments, the energy application may be used as a protective treatment or as a treatment applied in advance of an anticipated systemic challenge or disruption.

Figure 18C:
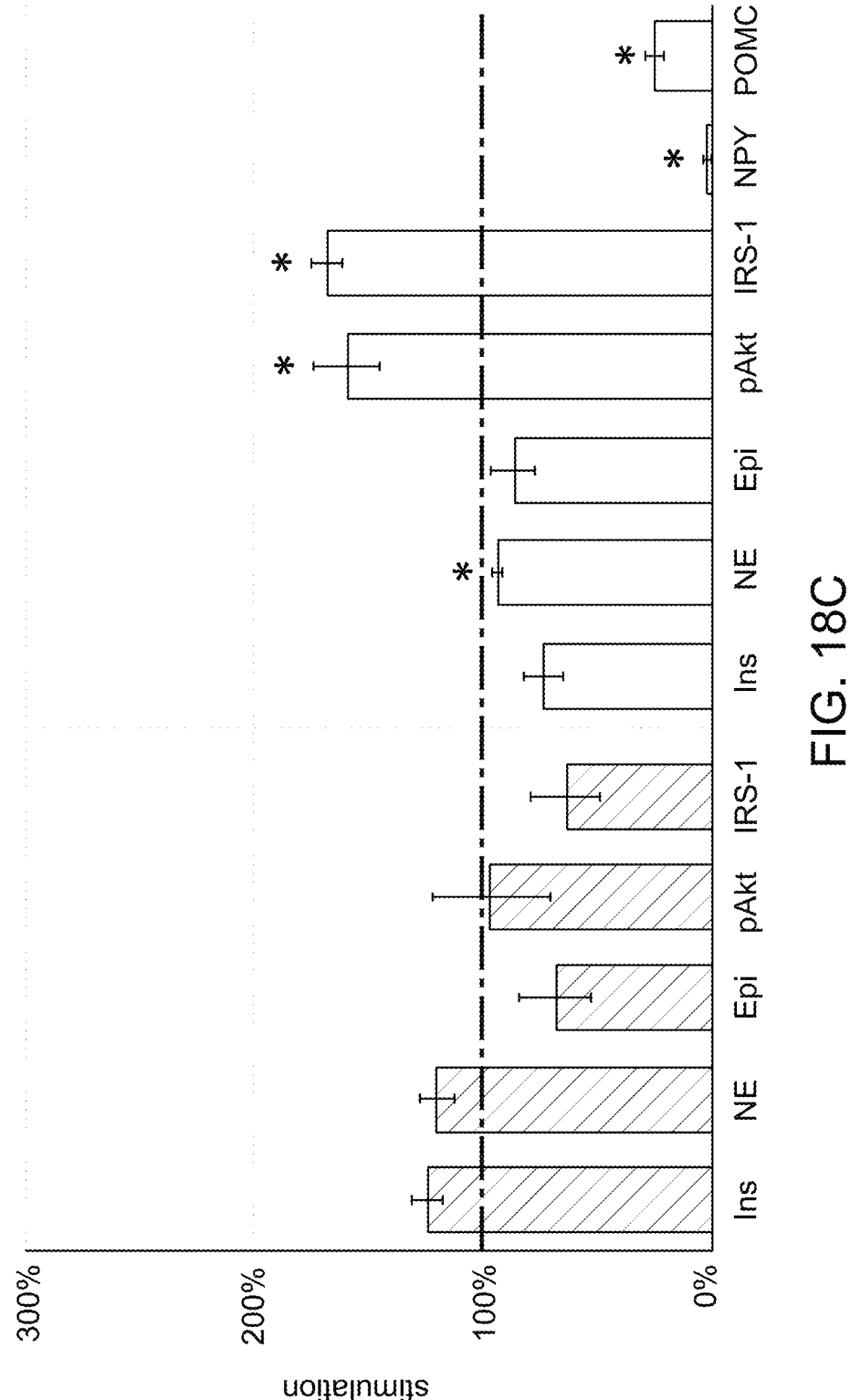
FIG. 18C shows measurements of relative concentrations (compared to no ultrasound stimulation) of several molecules associated with either insulin sensitivity and both insulin mediated as well as non-insulin dependent glucose uptake in the liver and changes in hypothalamic markers associated with metabolic function.

Selective modulation of one or more molecules of interest may be achieved at a site directly subjected to ultrasound stimulation, i.e., at the organ that includes the targeted region of interest. For example, targeted ultrasound stimulation of the liver at a region of interest induces changes in hepatic concentrations of signaling molecules within the liver tissue. Further, that are associated with glucose metabolism may remain unchanged (FIG. 18C, gray bars). Selective modulation of one or more molecules of interest may, additionally or alternatively, be achieved at a distal site not directly subjected to ultrasound stimulation. For example, FIG. 18C shows that applying ultrasound stimulation at a liver site may be used to induce significant changes of hypothalamic concentrations of NPY and NE, further inducing increased phosphorylation of ion channels indicative of increased activity of the insulin signaling pathway, which may indicated improved insulin sensitivity as well as improved glucose utilization.

FIG. 18C shows measurements of relative concentrations (compared to no ultrasound stimulation) of several molecules associated with either insulin sensitivity and both insulin mediated as well as non-insulin dependent glucose uptake in the liver and changes in hypothalamic markers associated with metabolic function. In the liver, epinephrine went down relative to changes in norepinephrine. Epinephrine may cause a prompt increase in blood glucose by driving release of stores from the liver. But, norepinephrine does not contribute significantly to hepatic glucose production in contrast to the norepinephrine effects on glucose uptake by skeletal muscle and adipose. Norepinephrine increases in the hypothalamus may specify an increase in hyperinsulinemia (indicating a decrease in insulin sensitivity) and glucose intolerance/hyperglycemia. Ultrasound stimulation may be used to selectively modulate or cause a change in the concentrations of one or molecules of interest at a distal site not directly subjected to the stimulation. For example, as illustrated in FIG. 18C, ultrasound stimulation may be used to modulate the concentration of molecules such as norepinephrine (NE), protein kinase B (pAkt), insulin receptor substrate 1 (IRS-1), and neuropeptide Y (NPY) at a distal hypothalamic site, when the direct ultrasound stimulation was applied to a site in the liver. In certain embodiments, ultrasound stimulation is selectively applied to a spatially selected region of interest of a tissue to achieve a desired (i.e., targeted) physiological outcome. The tissue may be selected from liver, pancreas, gastrointestinal tract, spleen, etc. The desired outcome may be a change in a concentration of a molecule or a marker of clinical relevance.

Figure 18D:
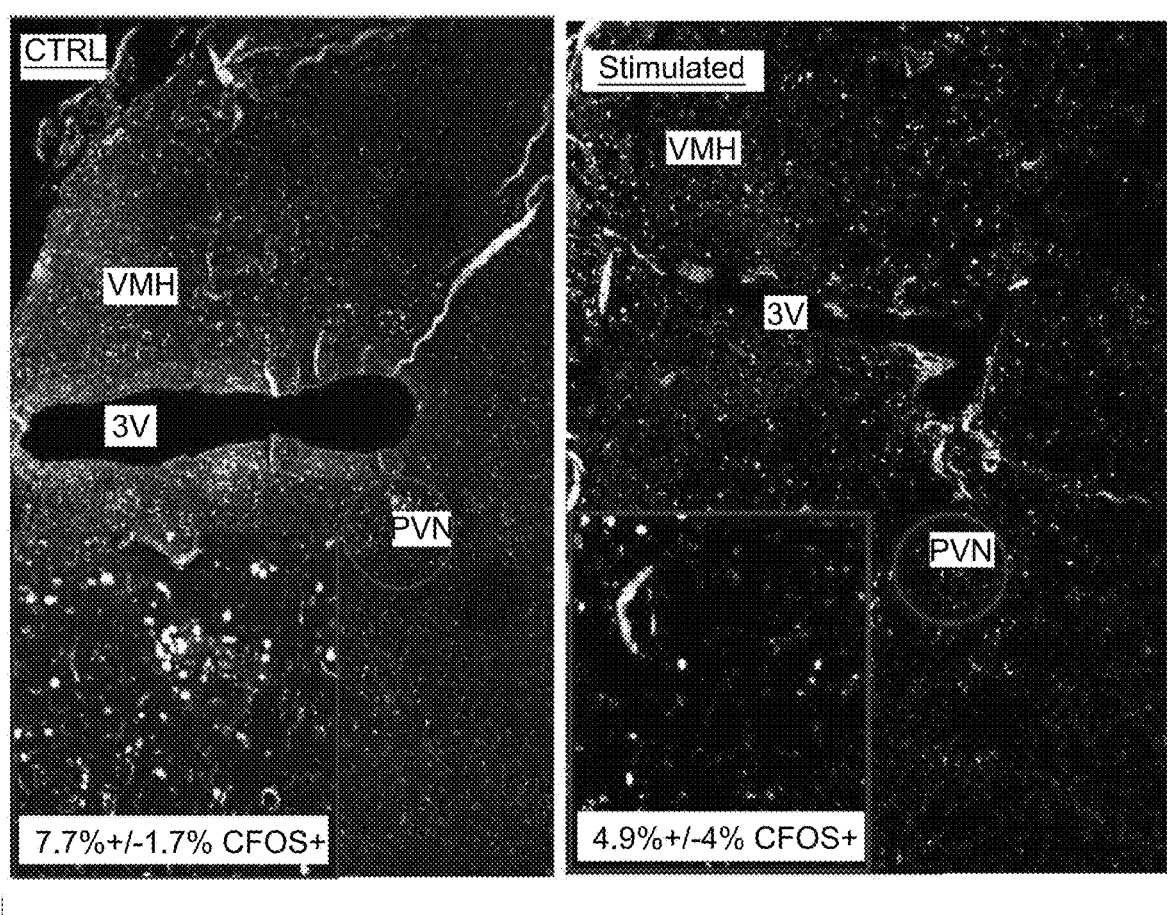
FIG. 18D shows cFOS immunohistochemistry images (left) and data showing the number of activated neurons in the LPS control and ultrasound stimulated samples (right)
Figure 18E:
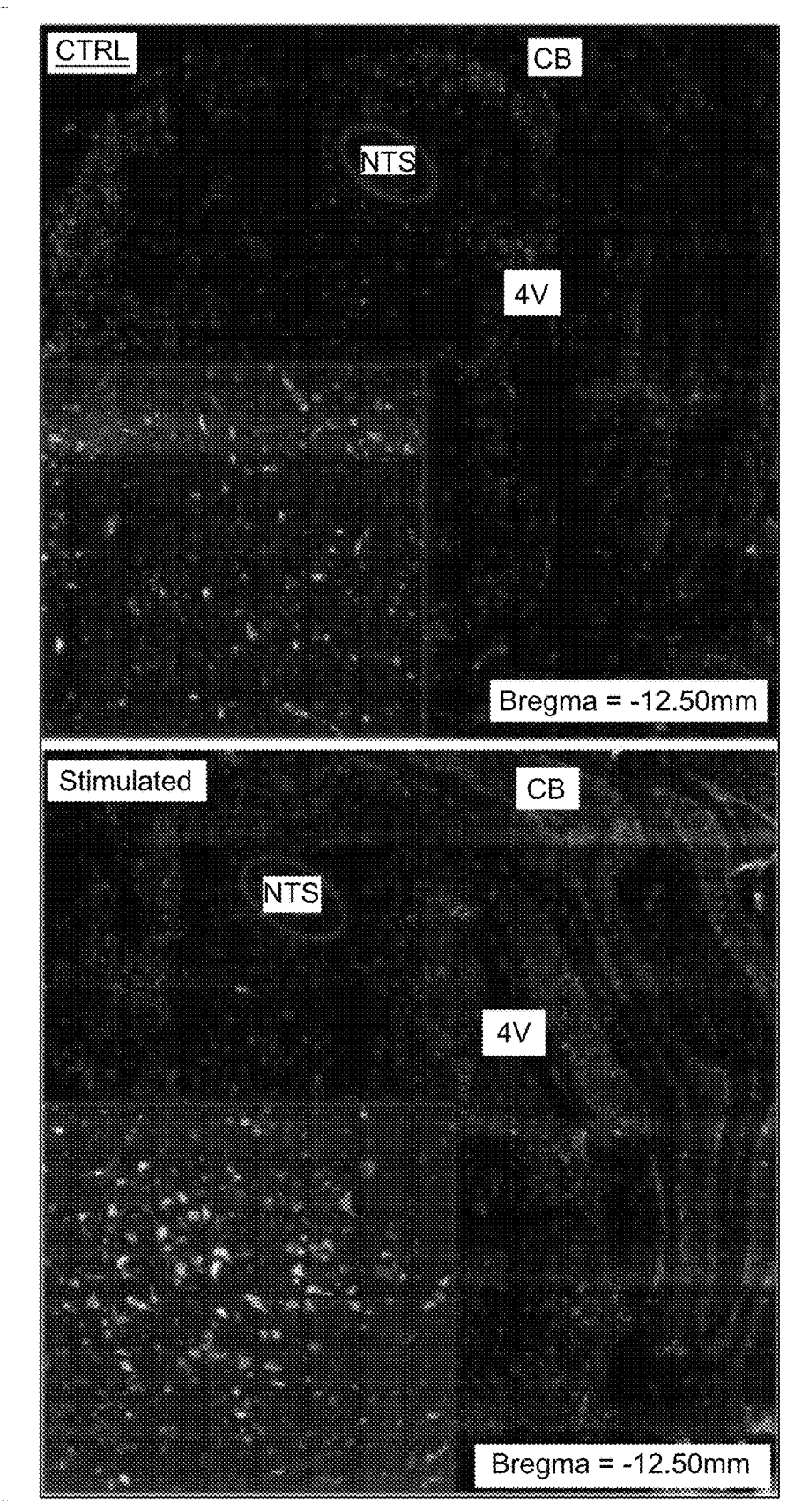
FIG. 18E shows additional immunohistochemistry images showing cFOS expression in the brainstem in LPS control (top) versus ultrasound stimulated samples (bottom)
Figure 18F:
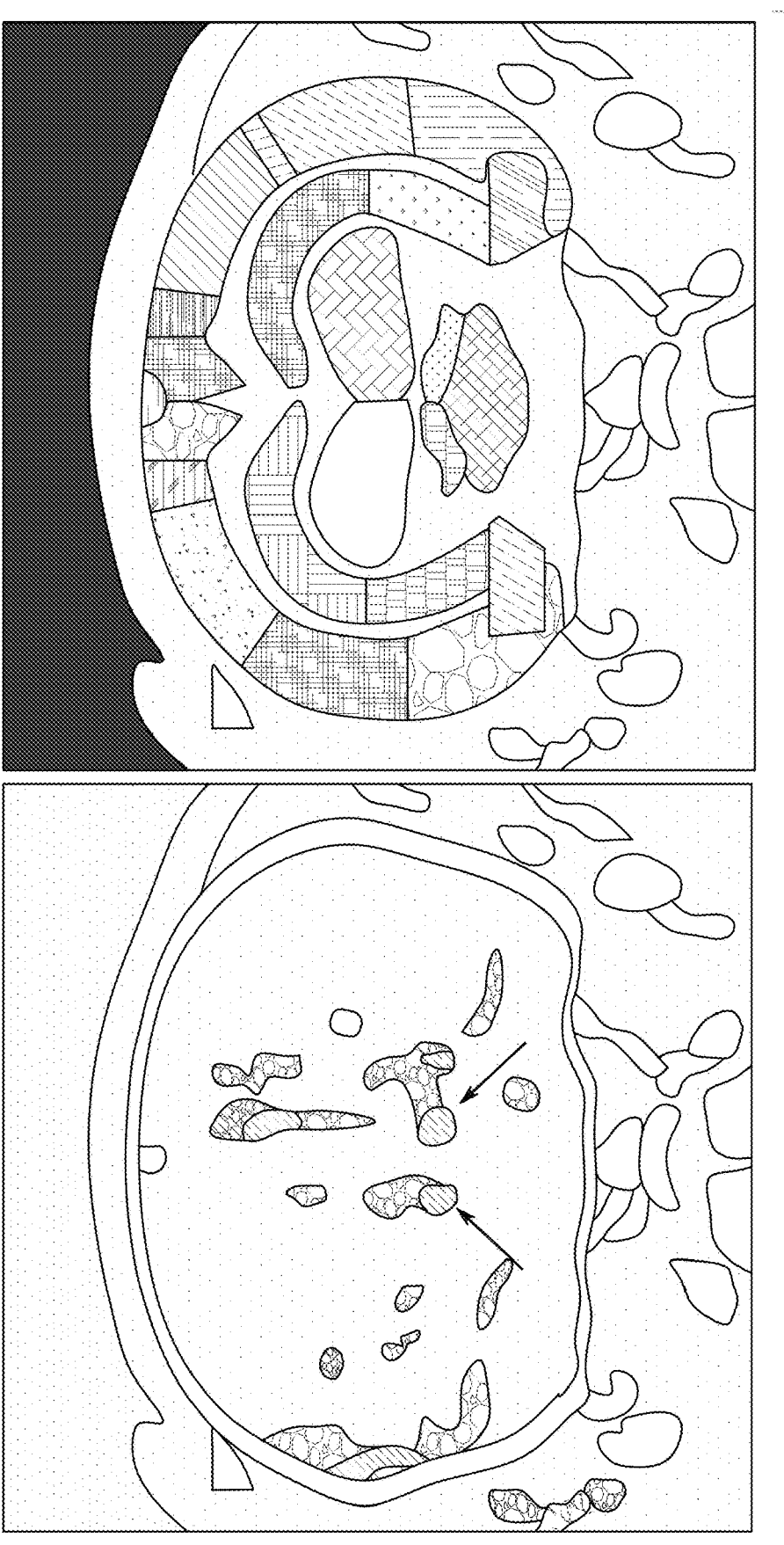
FIG. 18F shows example MRI overlays between activation maps (over SPGR volume; left) and a brain atlas (over SPBR volume; right)
Figure 18G:
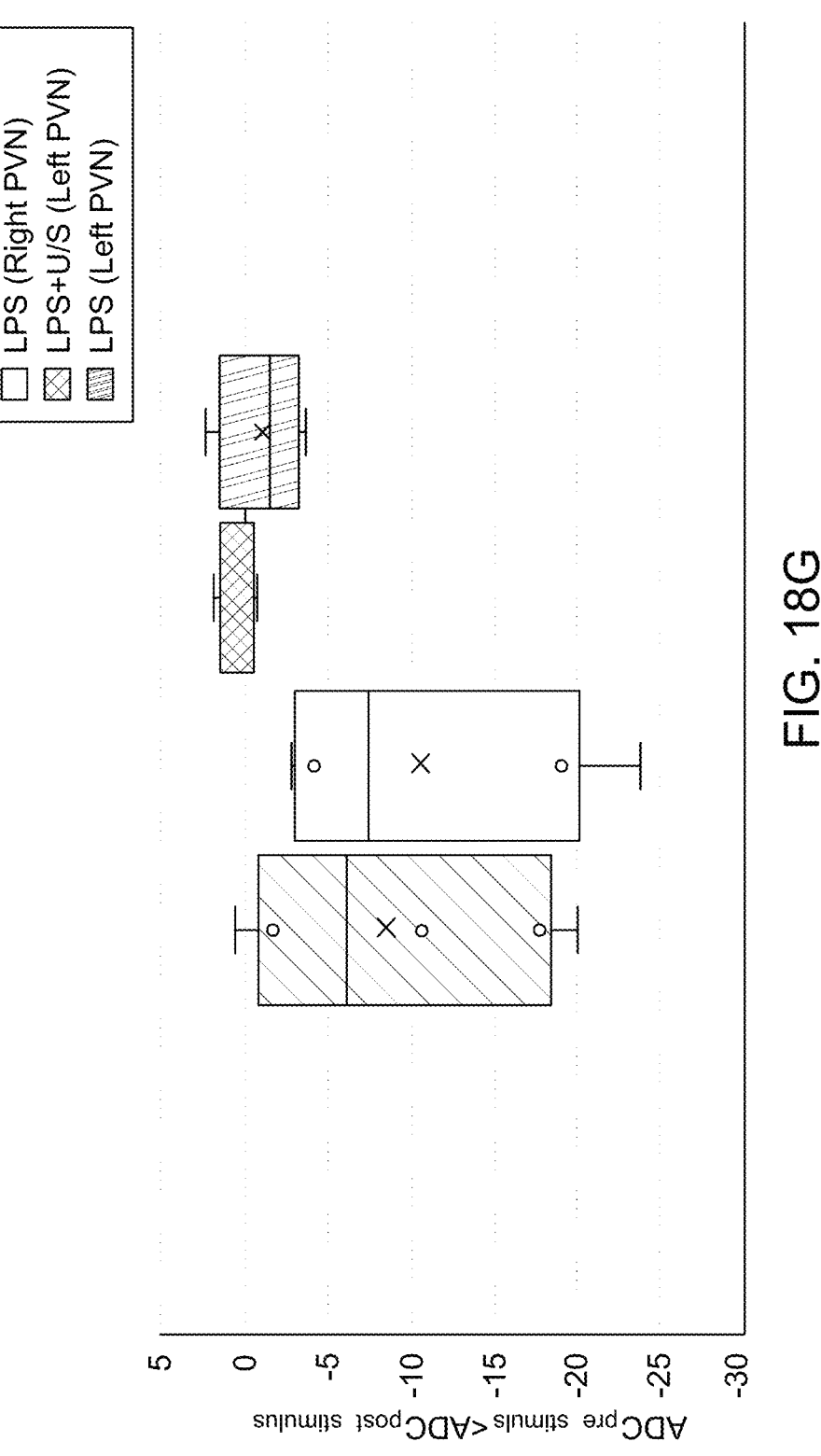
FIG. 18G shows t-test values from corresponding-pixel comparison between the pre- and post-treatment DWI images with the valid PVN ROIs applied to both images.

In certain embodiments, ultrasound-induced neuromodulation may be quantified by the extent of activity-dependent expression of the immediate early gene cFOS within defined hypothalamic and brainstem sub-nuclei (FIGS. 18D and 18E, respectively). FIG. 18D shows cFOS immunohistochemistry images (left) and data showing the percentage of activated neurons in the LPS control (left) and ultrasound stimulated samples (right). In the control image, the percentage of activated neurons is approximately 7.7%, while in the stimulated image, the percentage of stimulated neurons is approximately 4.9%. The images and data are segmented on the paraventricular nucleus (PVN). The decrease in neural activity, as represented by decreased percentage of activated neurons, following ultrasound stimulation provides further corroboration (in addition to data of FIG. 18C) of the effect of hepatic ultrasound neuromodulation on systemic glucose utilization and metabolic signaling. FIG. 18E shows additional immunohistochemistry images showing cFOS expression in the brainstem in LPS control (top) versus ultrasound stimulated samples (bottom). The images are segmented on the nucleus tractus solitaris (NTS), showing increased expression in the ultrasound stimulated samples. FIG. 18F shows example MRI overlays between activation maps (over spoiled gradient recalled echo volume; left) and a brain atlas (over spoiled gradient recalled echo volume; right). The example shows an ADC increase in both left and right paraventricular nuclei of the hypothalamus (PVNs) (arrows, left image), consistent with neuronal deactivation. FIG. 18G summarizes the results in a bar graph. Three of six rats showed significant deactivation in the PVNs; none of the control animals showed such deactivation. Furthermore, the hyperglycemia observed in the non-U/S-treated animals was not observed in the U/S-treated animals.

Table 2 shows t-test values obtained from the comparison of the ADC values within the validated PVN ROIs between the pre- and post-treatment scans.

TABLE 2

| | | Left PVN t-test values* | | | Right PVN t-test values* | | | Blood glucose concentration (mg/dL) | | |
|---|---|---|---|---|---|---|---|---|---|---|
| | | ROI min. | ROI ave. | ROI std. dev. | ROI min. | ROI ave. | ROI std. dev. | pre-LPS | 30-min-post-LPS | change |
| With | Rat 1 | −29.1 | −23.8 | 6.3 | −24.9 | −17.9 | 7.3 | N/A | 238 | N/A |
| U/S | Rat 2 | −3.8 | −2.8 | 1.1 | −2.8 | −1.6 | 0.8 | N/A | 196 | N/A |
| stimulation | Rat 3 | −7.2 | −4.2 | 2.3 | −1.0 | 0.6 | 1.4 | N/A | 204 | N/A |
| | Rat 4 | −12.6 | −10.6 | 1.5 | −12.1 | −10.6 | 1.2 | 233 | 246 | 13 |
| | Rat 5 | −22.0 | −19.1 | 1.9 | −22.8 | −20.2 | 2.6 | 146 | 171 | 25 |
| | Rat 6 | −3.9 | −2.9 | 0.6 | −1.3 | −1.3 | 2.3 | 124 | 183 | 59 |
| | Ave. | | −10.6 | | | −8.5 | | 168 | 206 | 39 |
| | St. dev. | | 2.1 | | | 2.4 | | 58 | 30 | |
| Without | Rat 7 | −2.7 | −1.3 | 1.2 | −2.1 | −0.6 | 1.2 | N/A | 440 | N/A |
| U/S | Rat 8 | −4.3 | −3.6 | 0.6 | −3.8 | −2.2 | 1.3 | 186 | 362 | 176 |
| stimulation | Rat 9 | −2.6 | −1.7 | 1.7 | −0.4 | −0.0 | 0.7 | 206 | 263 | 57 |
| | Rat 10 | 2.3 | 2.5 | 0.6 | 0.4 | 2.0 | 1.0 | 137 | 354 | 217 |
| | Ave. | | −1.0 | | | −0.2 | | 176 | 355 | 178 |
| | St. dev. | | 2.6 | | | 1.7 | | 36 | 72 | |

*t-test values obtained from the comparison of the ADC values within the validated PVN ROIs between the pre- and post-treatment scans.

The increases seen PVN ADC in 3 of 6 rats in response to the ultrasound stimulus were generally consistent with the c-Fos expression data, demonstrating ultrasound-induced deactivation of LPS-activated pathways communicating with the hypothalamus. Only some of the LPS+ ultrasound animals that exhibited this effect (rats 1, 4 and 5 in Table S2).

Compared to the controls, there was a significant decrease in cFOS positive (c-Fos+; FIG. 18D) cells within the paraventricular nucleus (PVN), suggesting ultrasound-induced modulation of the LPS-induced neural signaling. These data corroborate that concentrations of NPY and GABA significantly decreased following ultrasound stimulation because the arcuate nucleus (ARC) alters signals to the PVN based on peripheral sensory information via NPY-expressing neurons. Furthermore, the altered hypothalamic c-Fos expression was accompanied by significantly increased c-Fos expression within the nucleus tractus solitaris (NTS; FIG. 18E), indicating ultrasound-mediated modulation via signaling through afferent pathways.

The apparent diffusion coefficient (ADC) from diffusion-weighted functional magnetic resonance imaging (DfMRI) images in the hypothalamic sub-nuclei were compared before and after hepatic ultrasound stimulation. In response to the ultrasound stimulus the ADC increased within the PVN, corroborating both the chemical (POMC, NPY, and NE) and c-Fos expression data, which demonstrated ultrasound-induced deactivation of LPS-activated pathways communicating to the hypothalamus. These results are consistent with activation of a pathway that modulates the LPS-induced effect on energy metabolism via the NPY system and its effect on outgoing PVN signaling.

The disclosed techniques as provided herein permits precision neuromodulation with a simple, noninvasive technology. While demonstrated for two specific nerve pathways (the CAP in the spleen and metabolic sensory neurons in the liver), the techniques may be applied to modulate other peripheral nerve circuits.

Hyperglycemia Model

As provided herein, neuromodulation via application of energy to a region of interest may be used to treat a subject and/or to induce desired metabolic changes in a subject (e.g., a diseased subject, a healthy subject). In some embodiments, energy (e.g., ultrasound energy, mechanical energy) may be applied to one or more of a liver region of interest, a gastrointestinal region of interest, or a pancreatic region of interest, by way of example. Applying the energy may induce desired metabolic outcomes via selective neuromodulation of synapses in the region of interest to cause local effects at or near the site of energy application and systemic effects in distal tissues and in circulating molecules.

Figure 19:
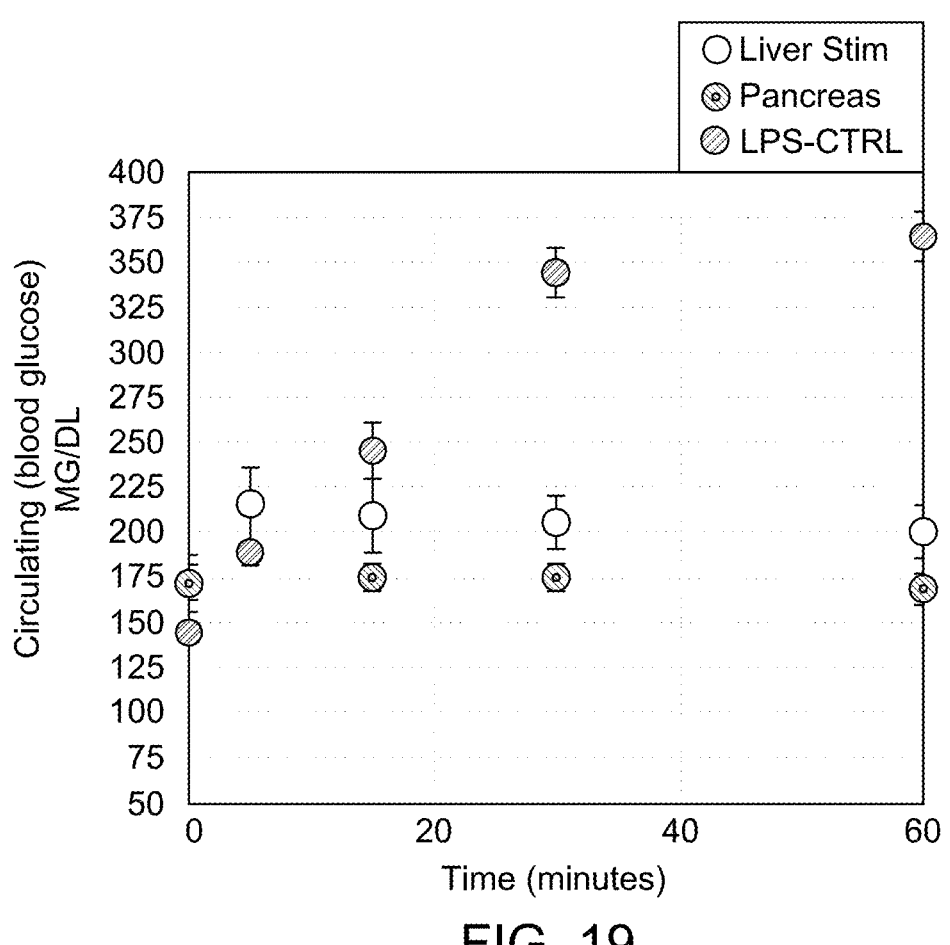
FIG. 19 shows circulating glucose levels decreased in response to pancreatic ultrasound stimulus in LPS rats.

FIGS. 19-44 are embodiments of ultrasound energy application in LPS rats. Insulin and glucagon are synthesized in the pancreatic islet cells and are involved in the regulation of blood glucose. LPS was used to generate acute insulin resistance and transient hyperglycemia in Sprague Dawley rats. In certain embodiments, ultrasound stimulus may be applied to a region of interest in the pancreas, to modulate the production of insulin and to induce a significant increase in circulating insulin concentration, in turn resulting in an acute decrease in circulating glucose concentration. As shown in FIG. 19, the circulating glucose concentration decreased in response to pancreatic ultrasound stimulus to a selected region of interest in the pancreas. The pancreatic ultrasound stimulation produced a reduction in circulating glucose concentration relative to a control LPS SD rat. As a comparison, applying an ultrasound stimulation at a region of interest at or near a liver porta hepatis, in accordance with techniques as provided herein, may also be used to achieve the similar outcome of reducing the circulating glucose concentration. Accordingly, in certain embodiments, a subject may be treated by applying energy to a pancreatic tissue according to the embodiments disclosed herein to induce a decrease in circulating glucose. A desired treatment outcome of the energy application to a pancreatic tissue may be assessed by evaluating circulating glucose concentration.

Figure 20:
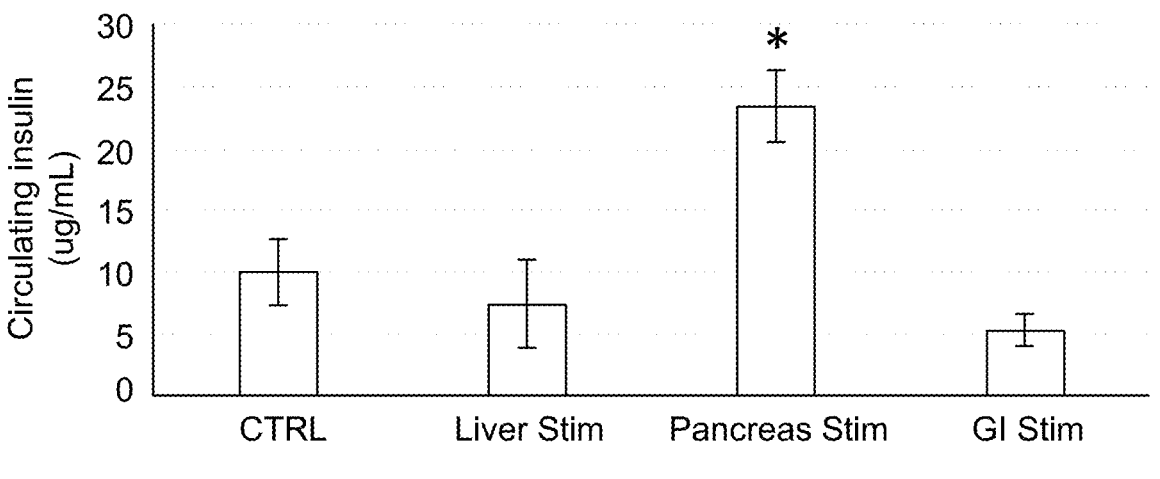
FIG. 20 shows the increase in circulating insulin in the pancreas-stimulated LPS SD rat.
Figure 21:
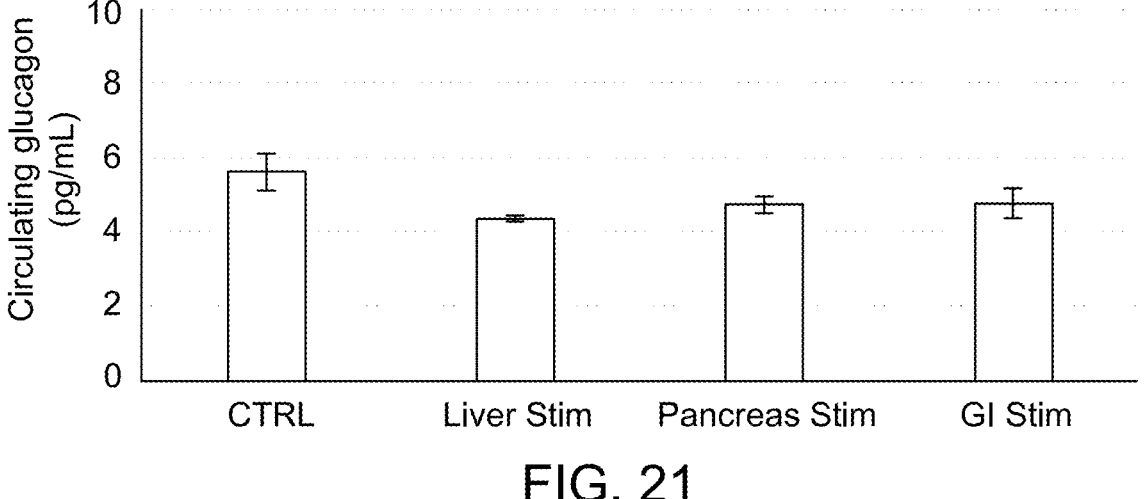
FIG. 21 shows no significant change in circulating glucagon concentration as a result of ultrasound stimulation in gastrointestinal, liver, and pancreas-stimulated LPS SD rats.

FIG. 20 shows that modulation of circulating insulin concentration may be achieved by selectively applying ultrasound stimulation to a region of interest in pancreas. For example, a significantly increased circulating insulin concentration is achieved by selectively applying ultrasound stimulation to a region of interest in the pancreatic tissue of a LPS SD rat. In comparison, ultrasound stimulations with modulation parameters as provided herein and applied to regions of interests selected to correspond to volumes in the liver or gastrointestinal tissue in a LPS SD rat does not induce significant change compared to the control LPS SD rat. This indicates that, while modulation of circulating glucose concentration may be achieved by directing ultrasound stimulation to pancreatic tissue or liver tissue, the mechanisms of reducing circulating glucose concentration may be different for pancreas stimulation relative to liver stimulation. For ultrasound stimulation of the pancreas, the induced increase in circulating insulin seen following direct ultrasound stimulation may contributes to the induced decrease in circulating glucose concentration, e.g., in a manner similar to early insulin resistance. FIG. 21 shows no significant change in circulating glucagon concentration as a result of ultrasound stimulation in gastrointestinal, liver, and pancreas-stimulated LPS SD rats. Accordingly, in certain embodiments, a subject may be treated by applying energy to a pancreatic tissue according to the embodiments disclosed herein to induce an increase in circulating insulin. A desired treatment outcome of the energy application to a pancreatic tissue may be assessed by evaluating circulating insulin concentration, either alone or together with circulating glucose concentration.

Figure 22:
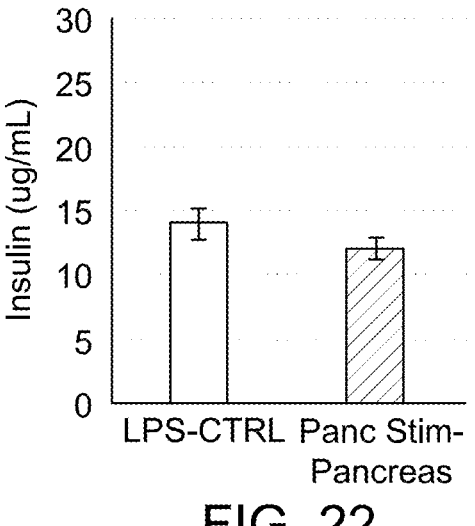
FIG. 22 shows levels of insulin in pancreatic tissue as a result of pancreatic ultrasound stimulation in the LPS SD rats.
Figure 23:
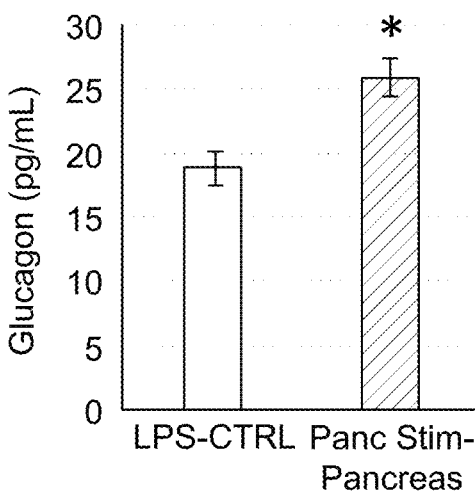
FIG. 23 shows levels of glucagon in pancreatic tissue as a result of pancreatic ultrasound stimulation in the LPS SD rats.

FIG. 22-23 show concentrations of molecules in pancreatic tissue as a result of applying ultrasound stimulation to a region of interest in the pancreatic tissue in the LPS SD rats. As shown in FIG. 22, pancreatic stimulation does not induce significant changes in insulin concentration in the pancreatic tissue. The lack of observable changes in insulin within the pancreatic tissue may be associated with the elevated circulating insulin via an expenditure of existing insulin stores within pancreas. That is, increased pancreatic insulin may result in subsequent increased circulating insulin and, in turn, a pancreatic insulin level that returns to baseline after expenditure during a refractory period while insulin levels are replenished after expenditure. In contrast, pancreatic ultrasound stimulus may be applied to induce a significant increase of glucagon concentration in the pancreatic tissue (FIG. 23), compared to control LPS SD rats that are not subjected to ultrasound stimulation. Glucagon is a protein that is involved in the regulation of glucose production in the liver (via glycogenolysis), independent of the present hyperglycemia in the depicted animal model. The data, as illustrated in FIGS. 22 and 23, demonstrates that applying ultrasound stimulation, for example, an image-guided application/delivery of ultrasound stimulation to a region of interest in the pancreas may be used to modulate (i.e., induces changes in) the glucagon concentration (for example, increase glucagon secretion by pancreatic alpha cells) and to modulate the concentration of circulating glucose. In certain embodiments, the application of ultrasound stimulation to a region of interest in the pancreas tissue may be used, as a standalone treatment or in combination with other treatment options, for treating recurrent hypoglycemia, for example, for treating type 1 diabetes.

Figure 24:
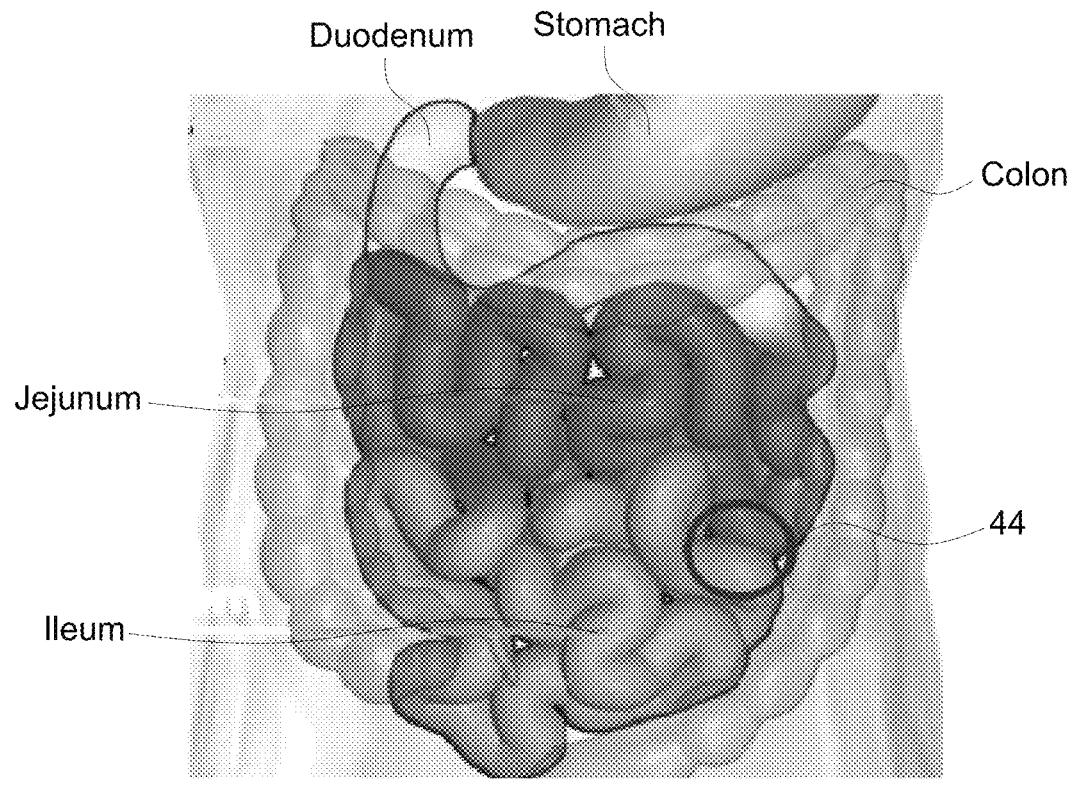
FIG. 24 shows a region of interest in the gastrointestinal tissue targeted for the gastrointestinal ultrasound stimulation in an LPS SD rat as provided herein.
Figure 25:
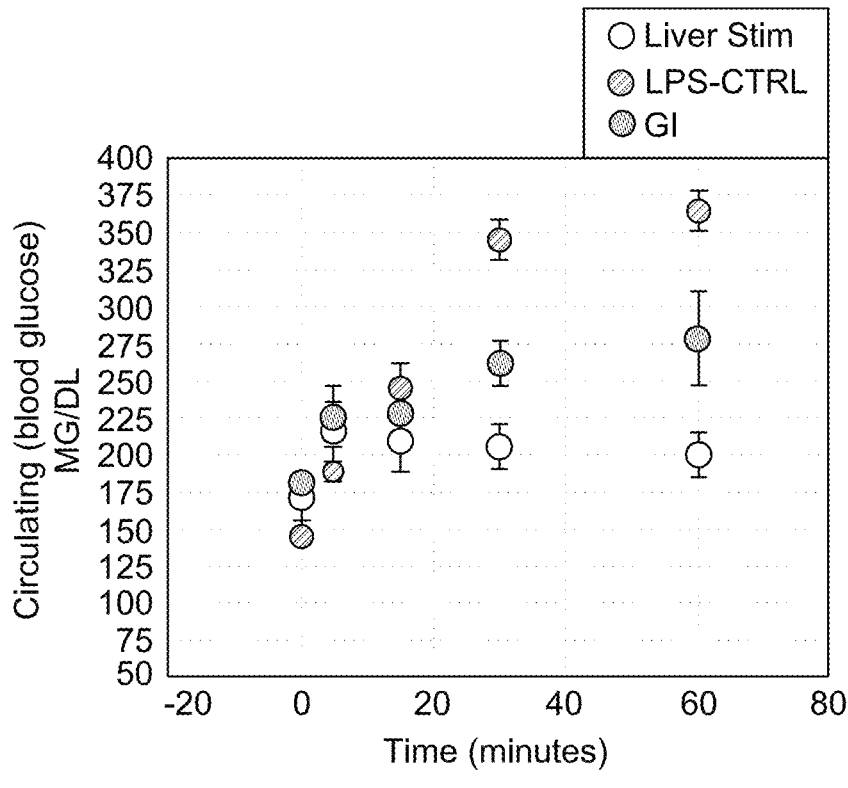
FIG. 25 shows a reduction in circulating glucose in response to gastrointestinal ultrasound stimulation in the rat model.
Figure 26:
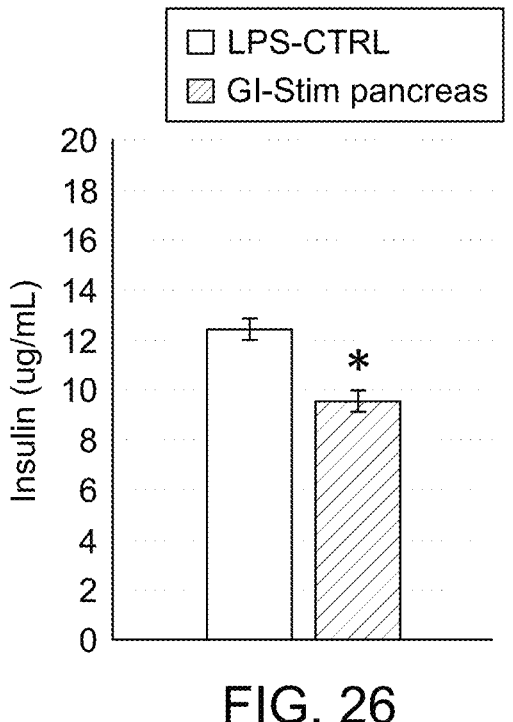
FIG. 26 shows insulin levels within the pancreas following gastrointestinal ultrasound stimulus.
Figure 27:
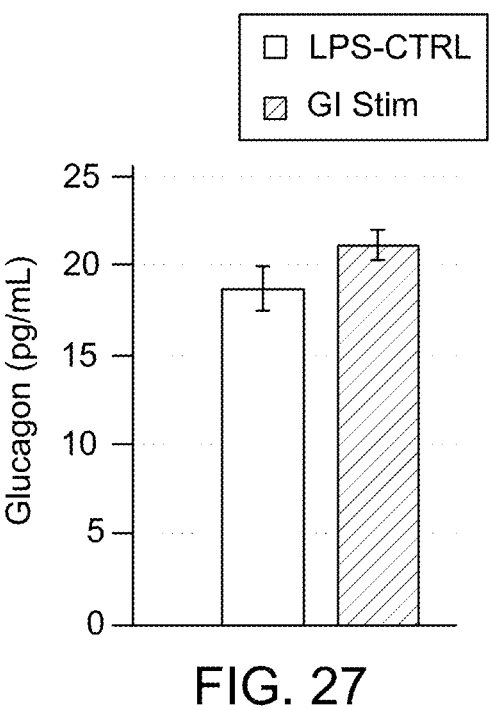
FIG. 27 shows glucagon levels within the pancreas following gastrointestinal ultrasound stimulus.
Figure 28:
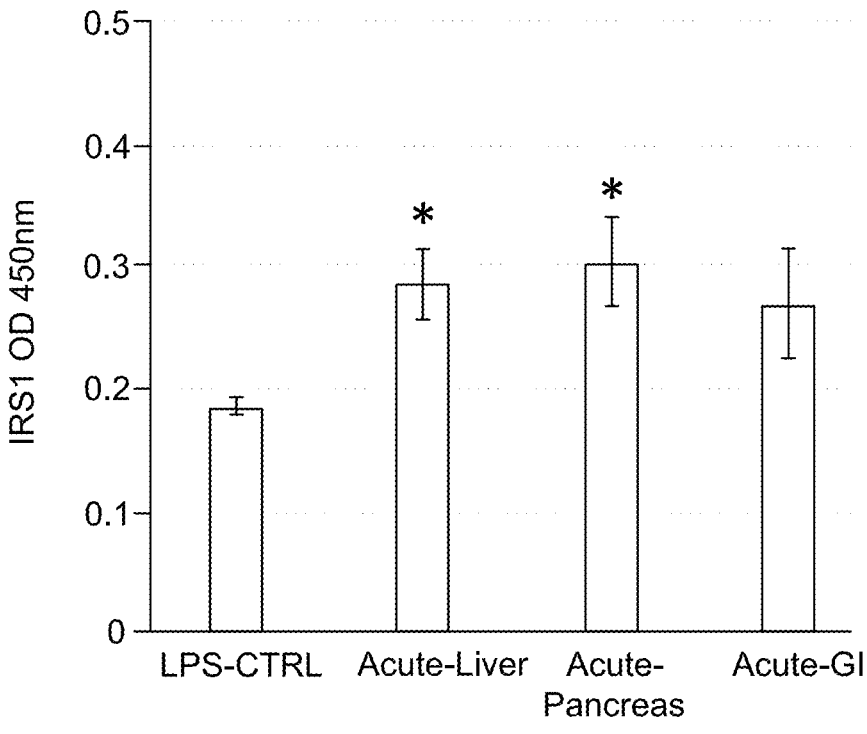
FIG. 28 shows hypothalamic IRS1 levels in response to gastrointestinal, liver, and pancreatic ultrasound stimulation relative to control.
Figure 29:
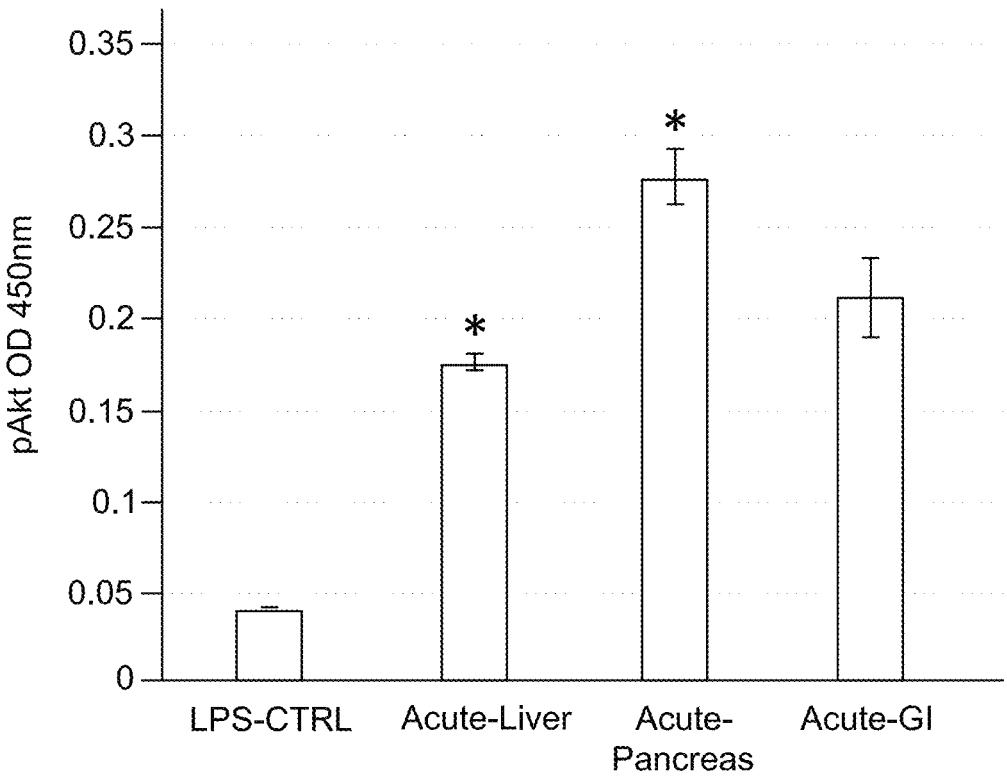
FIG. 29 shows hypothalamic phos-Akt levels in response to gastrointestinal, liver, and pancreatic ultrasound stimulation relative to control.
Figure 30:
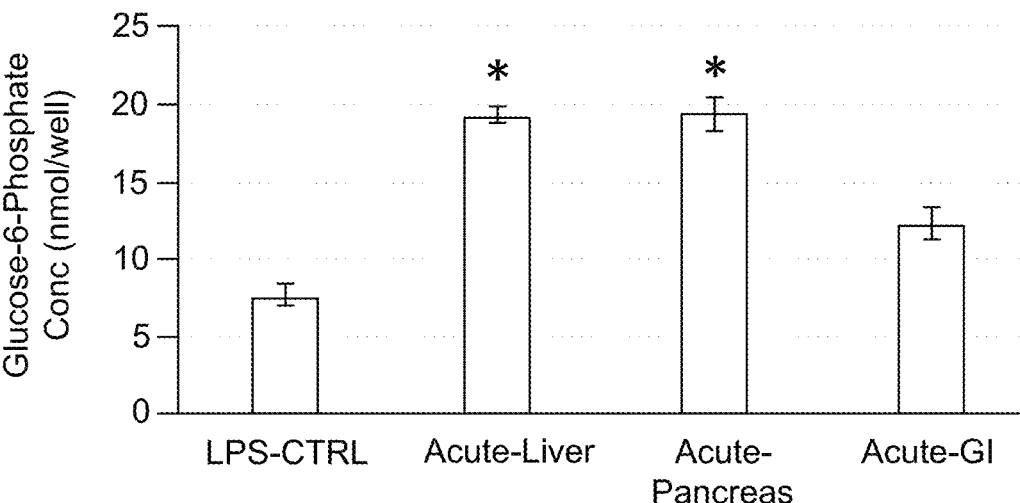
FIG. 30 shows hypothalamic glucose-6-phosphate levels in response to gastrointestinal, liver, and pancreatic ultrasound stimulation relative to control.

FIG. 24 shows a region of interest in the gastrointestinal tissue targeted for the gastrointestinal ultrasound stimulation in an LPS SD rat as provided herein. The region of interest in the gastrointestinal tissue may be spatially selected as provided herein. For example, the region of interest may be selected using image analysis to identify sections of the stomach and the intestines and their locations relative to other organs. For example, certain sections of the intestines may be spaced apart from or located away from other organs (i.e., the pancreas), while the stomach is relatively close to the pancreas. Targeting the intestines permits relatively straightforward spatial selection while avoiding relatively more complex spatial selection of the stomach tissue while avoiding the pancreas. FIG. 25 shows a reduction in circulating glucose in response to gastrointestinal ultrasound stimulation in the rat model. There was a minor albeit significant decrease in insulin within the pancreas (FIG. 26) following ultrasound stimulus. A minor but significant change in glucagon in the pancreas (FIG. 27) was observed. Accordingly, as provided herein, neuromodulation via application of energy (e.g., ultrasound energy) to a gastrointestinal tissue in a region of interest may be used to control circulating glucose in a subject. A hyperglycemic subject may be treated by applying energy to a gastrointestinal tissue according to the embodiments disclosed herein to induce a decrease in circulating glucose. After the treatment, a concentration of circulating glucose may be assessed on an ongoing or intermittent basis to determine additional treatment parameters. In certain embodiments, the effect may persist for hours and/or days. Further, neuromodulation via application of energy to a gastrointestinal tissue in a region of interest may be used to control metabolic processes that influence insulin levels in the pancreas. A subject may be treated by applying energy to a gastrointestinal tissue according to the embodiments disclosed herein to induce a decrease in circulating glucose. A desired treatment outcome of the energy application to a gastrointestinal tissue may be assessed by evaluating one or more of the circulating glucose concentration, the concentration of pancreatic insulin, and the concentration of glucagon in the pancreas. For example, an induced decrease in circulating glucose without significant changes in pancreatic glucagon may be indicative of a desired characteristic profile of glucose metabolism in the treated subject.

Figure 31:
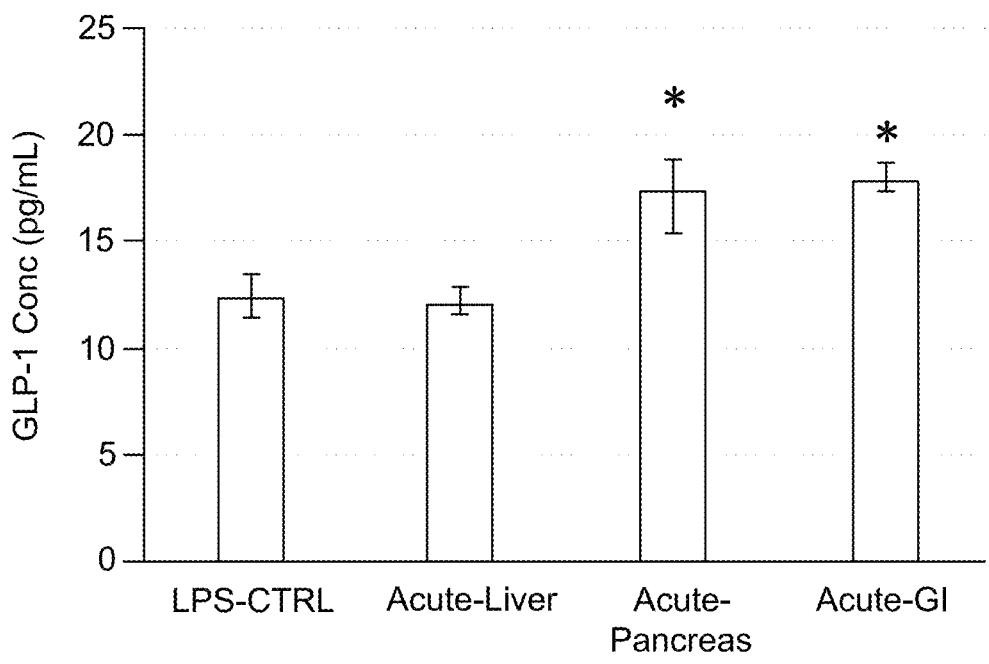
FIG. 31 shows hypothalamic GLP-1 levels in response to gastrointestinal, liver, and pancreatic ultrasound stimulation relative to control.
Figure 32:
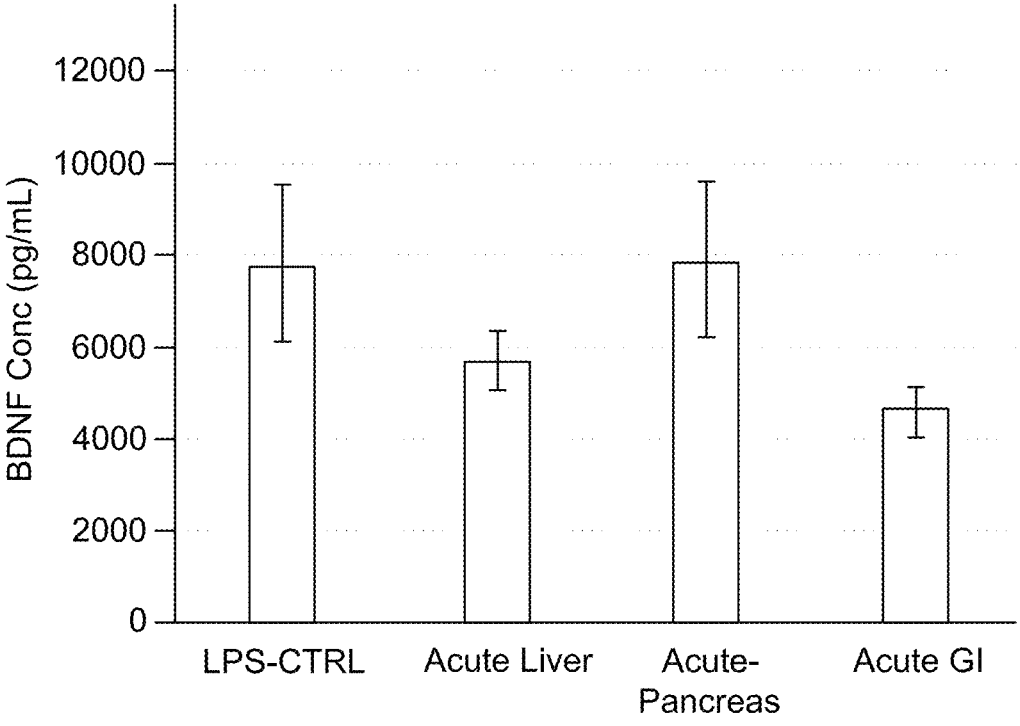
FIG. 32 shows hypothalamic BDNF levels in response to gastrointestinal, liver, and pancreatic ultrasound stimulation relative to control.
Figure 33:
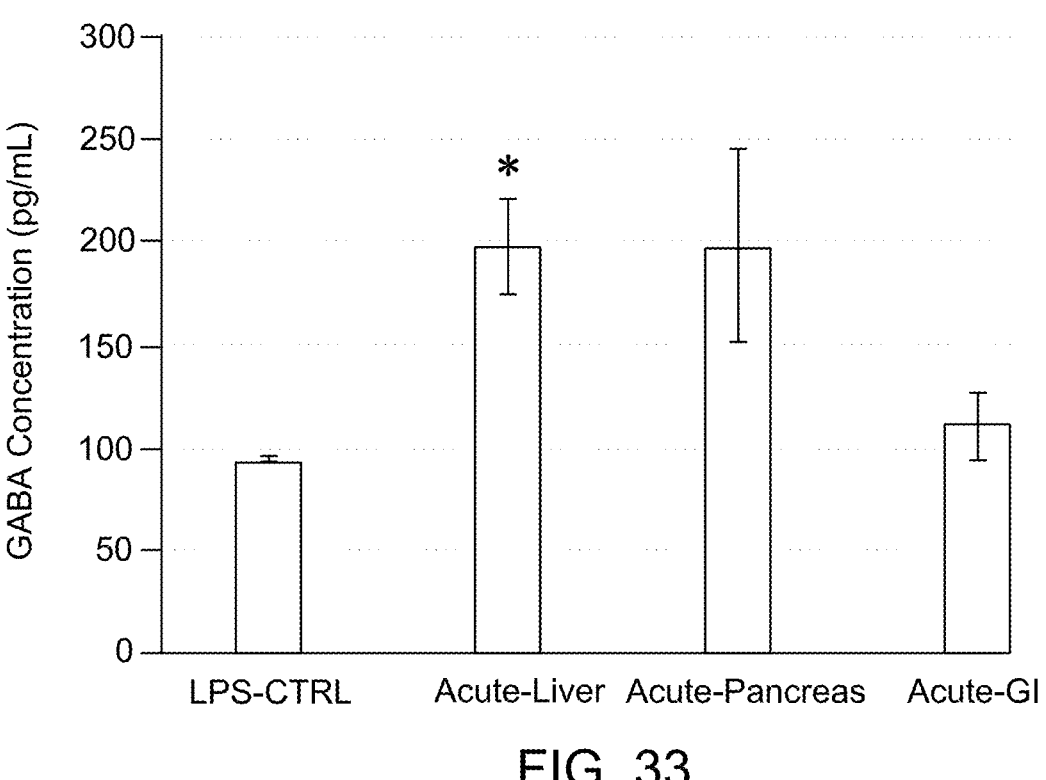
FIG. 33 shows hypothalamic GABA levels in response to gastrointestinal, liver, and pancreatic ultrasound stimulation relative to control.
Figure 34:
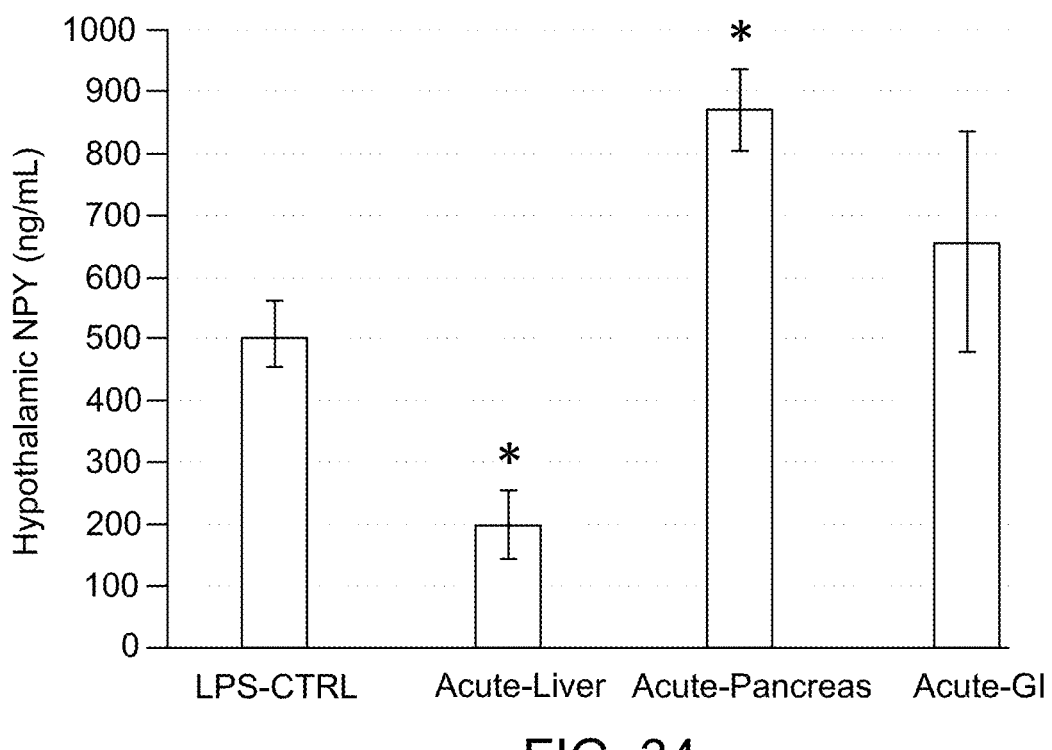
FIG. 34 shows hypothalamic NPY levels in response to gastrointestinal liver, and pancreatic ultrasound stimulation relative to control.

FIGS. 28-33 show hypothalamic markers (IRS1, phosAKt, GLP-1, hypothalamic NPY, or glucose-6-phosphate) in response to gastrointestinal, liver, and pancreatic ultrasound stimulation relative to control. There was a significant increase in protein subunits involved in the insulin signaling/insulin mediated glucose uptake pathways in pancreatic ultrasound-treated animals. This pathway is known to be dysfunctional in the hypothalamus of rodent and humans showing insulin resistance a common hallmark of type 2 diabetes mellitus. Increase in this signaling pathway coupled with an increase in glucose-6-phosphate concentration in the hypothalamus is an indicator of insulin signaling and systemic insulin sensitivity. Limited response relating to insulin signaling was seen following gastrointestinal stimulus. An increase in GLP-1 and the associated receptor activation is known to promote weight loss and improve glucose tolerance and is a current target of pharmacologic intervention in diabetics (e.g. GLP-1 agonists; exenatide). GLP-1 increases were seen as a result of pancreatic and gastrointestinal ultrasound stimulation (FIG. 31). GABA increases (as seen in the liver-stimulated rat in the results in FIG. 33) in the hypothalamus may influence known hypothalamic markers (e.g. NPY) resulting to peripheral glucose control by modulation of the magnitude of glucagon and sympathoadrenal response to glucose. Hypothalamus markers may include markers of energy balance, such as NPY, POMC, and BDNF, among others. Hypothalamic NPY was shown to decrease as a result of liver stimulation (FIG. 34). As disclosed herein, the characteristic induced changes, or lack thereof, in hypothalamic markers that occur concurrently with other changes (e.g., changes in glucose or insulin concentrations as a result of gastrointestinal, liver, and/or pancreatic ultrasound stimulation) may form a suite of changes or a characteristic profile that is associated with the targeted physiological outcome. The system may be configured to assess one or more of these changes as a proxy for the targeted physiological outcome or as a characteristic profile of desired glucose metabolism in the treated subject.

Figure 35:
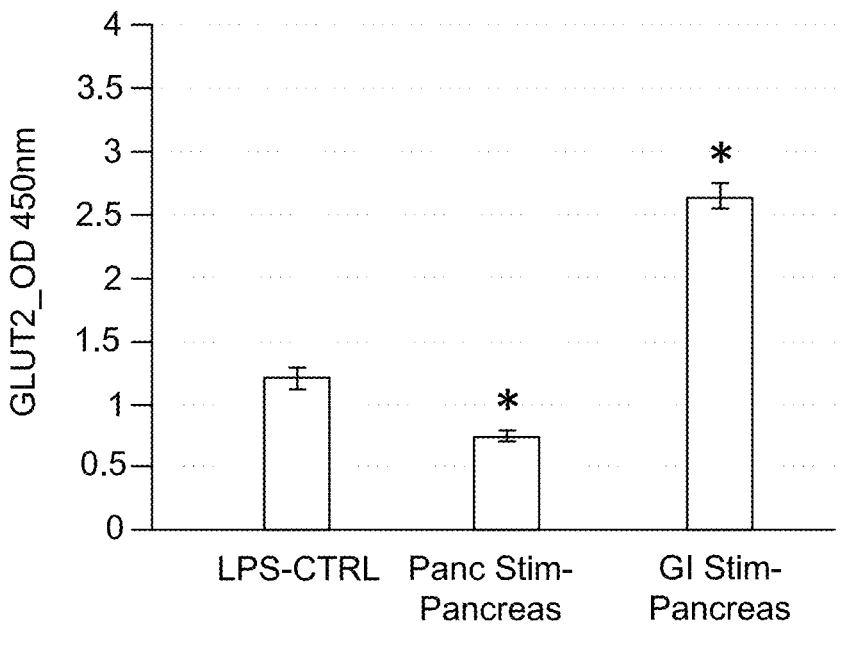
FIG. 35 shows pancreatic GLUT2 levels and the effects of liver, gastrointestinal, or pancreatic ultrasound stimulation.
Figure 36:
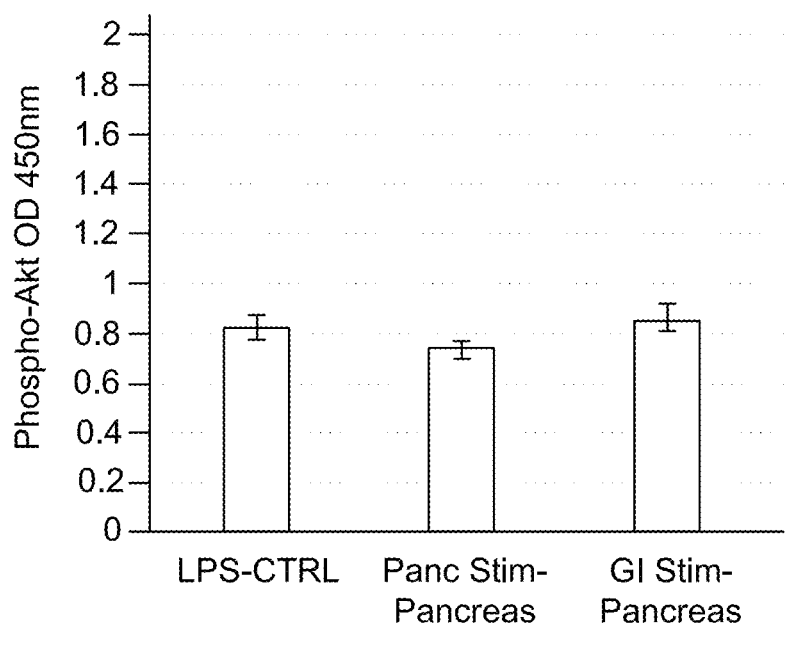
FIG. 36 shows pancreatic phosphor-Akt levels and the effects of liver, gastrointestinal, or pancreatic ultrasound stimulation.
Figure 37:
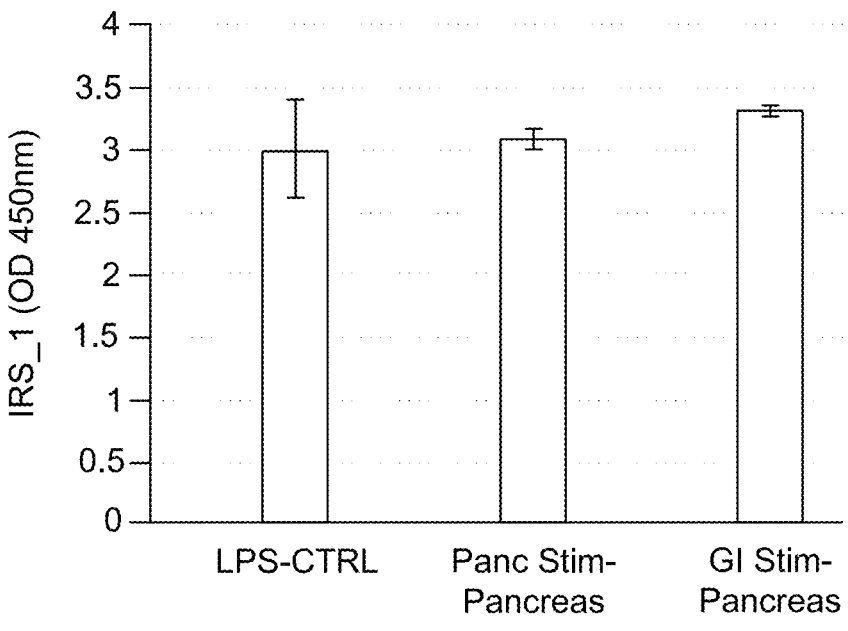
FIG. 37 shows pancreatic IRS1 levels and the effects of liver, gastrointestinal, or pancreatic ultrasound stimulation.
Figure 38:
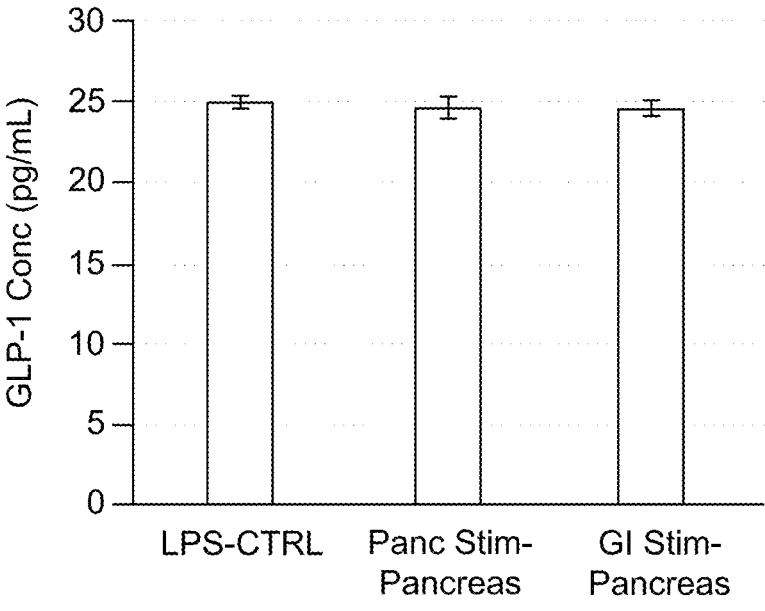
FIG. 38 shows pancreatic GLP-1 levels and the effects of liver, gastrointestinal, or pancreatic ultrasound stimulation.
Figure 39:
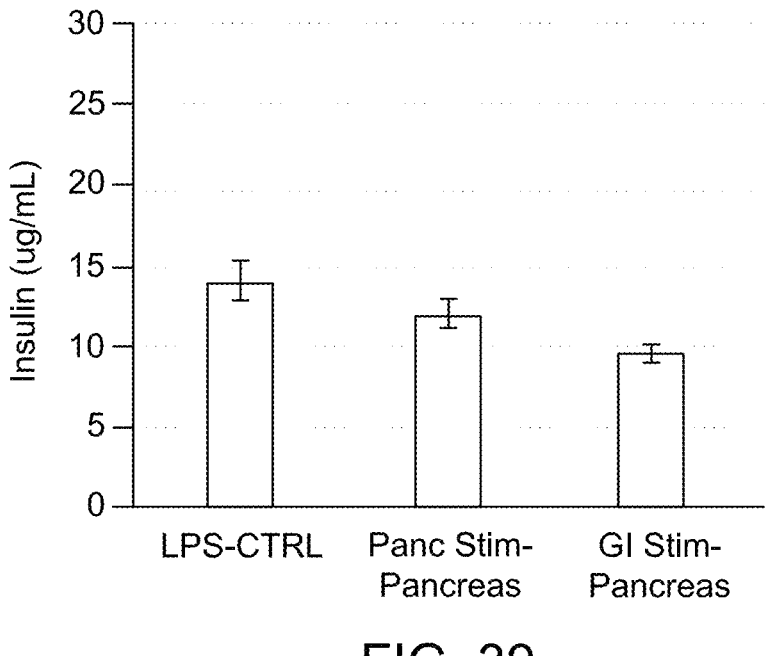
FIG. 39 shows pancreatic insulin levels and the effects of liver, gastrointestinal, or pancreatic ultrasound stimulation.
Figure 40:
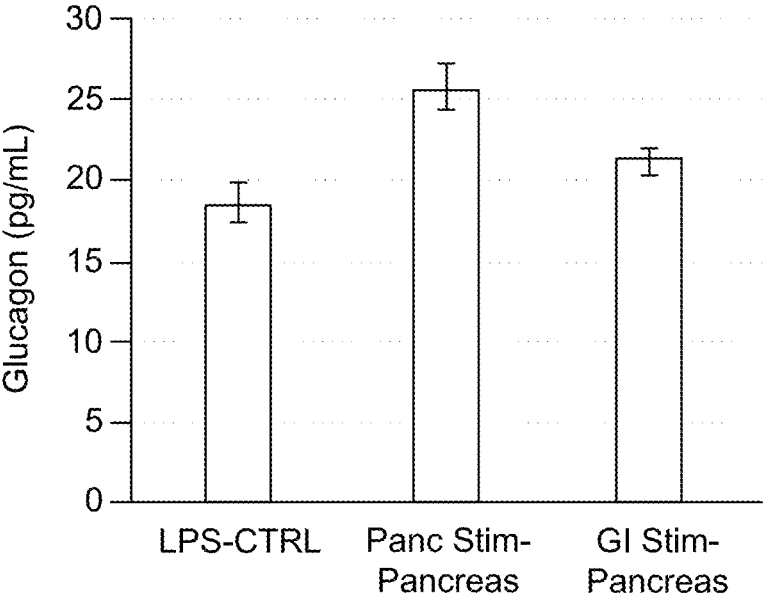
FIG. 40 shows pancreatic glucagon levels and the effects of liver, gastrointestinal, or pancreatic ultrasound stimulation.
Figure 41:
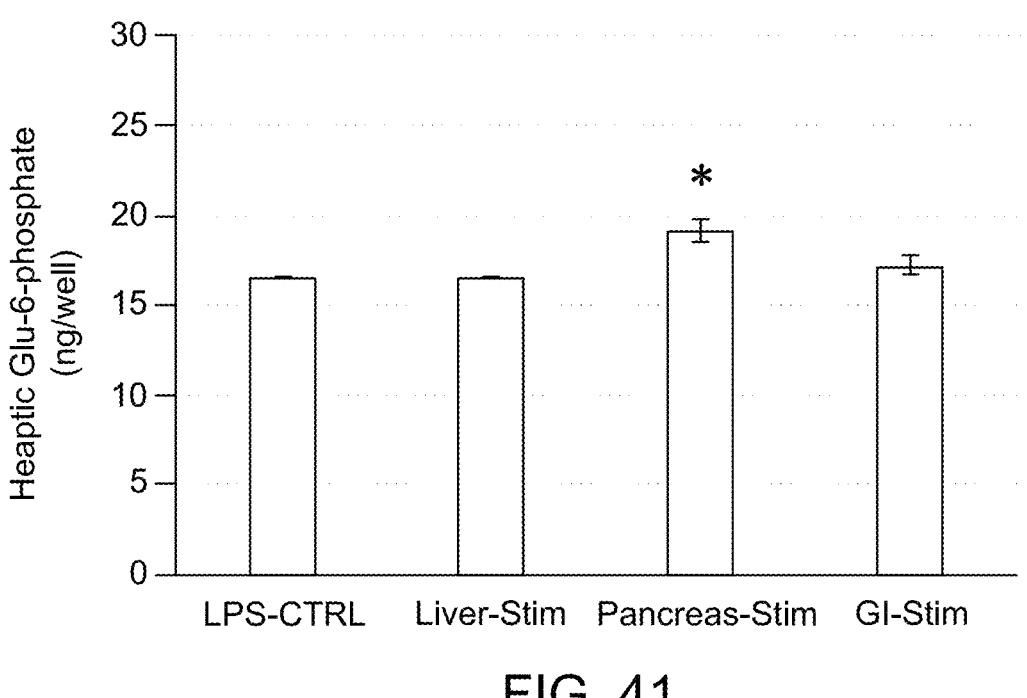
FIG. 41 shows hepatic glucose-6-phosphate levels and the effects of liver, gastrointestinal, or pancreatic ultrasound stimulation.
Figure 42:
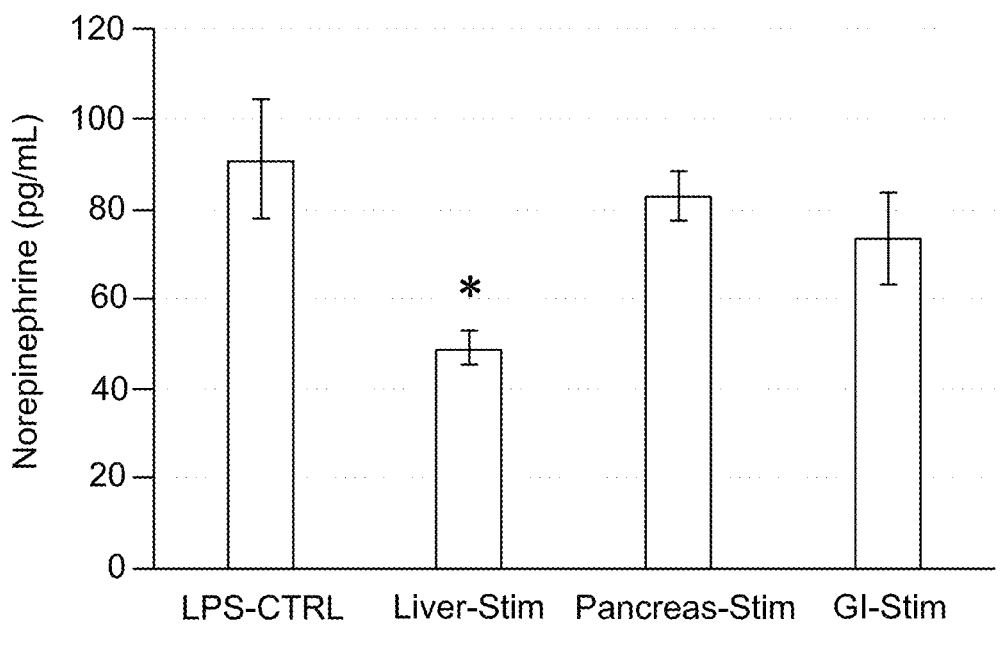
FIG. 42 shows hepatic norepinephrine levels and the effects of liver, gastrointestinal, or pancreatic ultrasound stimulation.
Figure 43:
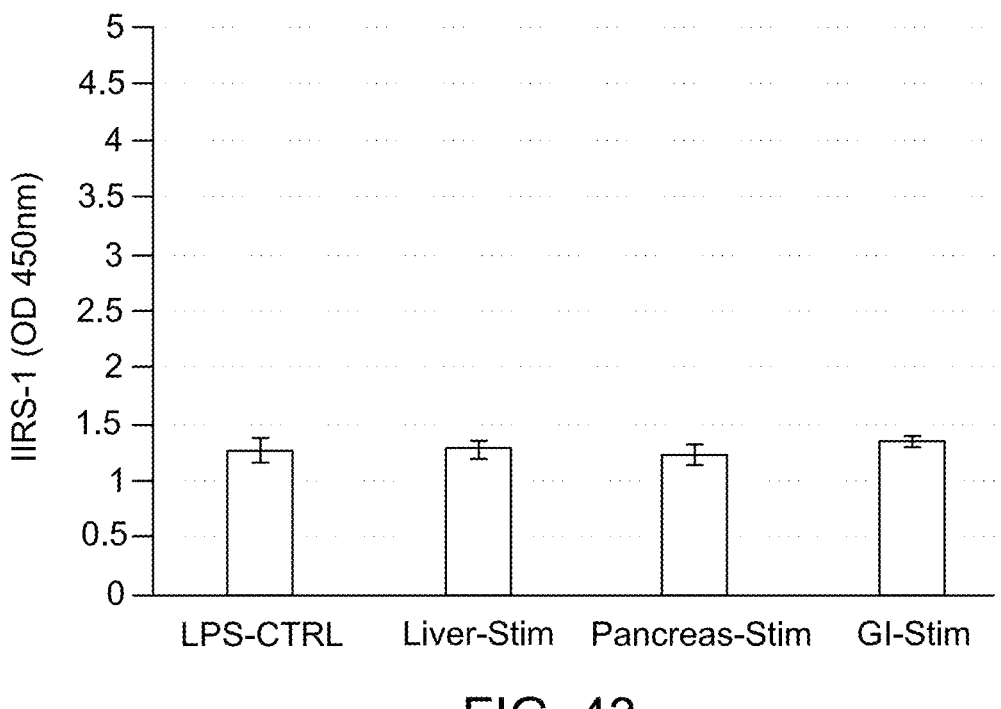
FIG. 43 shows hepatic IRS-1 levels and the effects of liver, gastrointestinal, or pancreatic ultrasound stimulation.
Figure 44:
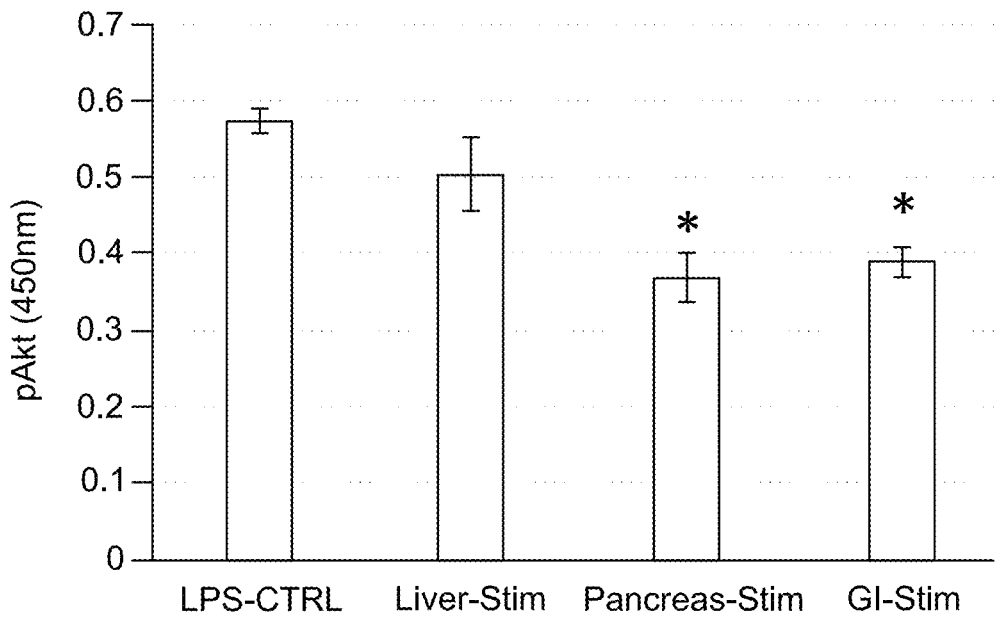
FIG. 44 shows hepatic phos-Akt levels and the effects of liver, gastrointestinal, or pancreatic ultrasound stimulation.

FIGS. 35-37 show pancreatic markers of the insulin mediated glucose uptake pathway for pancreatic β cells and the effects of liver, gastrointestinal, or pancreatic ultrasound stimulation on these markers. IRS-1 and pAKT did not change, but GLUT2 increased likely indicates that, in the pancreas, ultrasound energy application caused increasing glucose uptake by GLUT2 in a non-insulin dependent manner. FIGS. 38-40 show pancreatic hormones involved in glucose regulation by the pancreas and the effects of liver, gastrointestinal, or pancreatic ultrasound stimulation on these markers. GLUT2 showed a significant decrease in response to pancreatic stimulation and a significant increase in response to gastrointestinal stimulation. Accordingly, pancreatic and liver stimulation may activate opposing or bi-directional pathways involved in glucose regulation. To avoid overstimulation of the glucose regulatory pathways in the liver, both the pancreas and the liver tissue may be targets of ultrasound (or other energy) application in a subject such that glucose regulatory pathways are activated but also subject to signaling molecules associated with downregulation. By stimulating bi-directional pathways, a stable glucose concentration may be achieved for subjects that are at risk for hyper or hypoglycemia. It should be understood that GLUT2 is an example of a marker of bi-directional pathways and that other mechanisms or pathways may also be targeted. Bi-directional stimulation may be implemented as provided herein to a first region of interest in a first organ or first tissue and a second region of interest in a second organ or second tissue. In another embodiment, multi-site neuromodulation may be performed on different sites that enhance that same pathways. The energy application to the first region of interest and the second region of interest may be in parallel or in series. In one embodiment, the first region of interest is in a liver and a second region of interest is in a pancreas. In another embodiment, the first region of interest is in a gastrointestinal tissue and a second region of interest is in a liver.

FIGS. 41-44 show hepatic markers and the effects of liver, gastrointestinal, or pancreatic ultrasound stimulation on these markers. The increase of glucose-6-phosphate indicates modulating hepatic glycolytic and gluconeogenic pathways. As disclosed herein, the characteristic changes, or lack thereof, in hepatic markers that occur concurrently with other changes (e.g., changes in glucose or insulin concentrations as a result of ultrasound stimulation) may form a suite of changes or a characteristic profile that is associated with the targeted physiological outcome. The system may be configured to assess one or more of these changes as a proxy for the targeted physiological outcome.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A modulation system comprising:
a non-invasive ultrasound probe, configured to emit one or more imaging beams and one or more therapy beams using the same or different transducers; and
a controller configured to:
direct the non-invasive ultrasound probe on a first region of interest of a first tissue comprising a liver or sub-region of the liver;
adjustably control the non-invasive ultrasound probe to apply a first energy dose to the liver or the sub-region of the liver, wherein applying the first energy dose to the liver or the sub-region of the liver decreases circulating glucose concentration;
direct the non-invasive ultrasound probe or a different non-invasive ultrasound probe on a second region of interest comprising a gastrointestinal tissue; and
adjustably control the non-invasive ultrasound probe or the different non-invasive ultrasound probe to apply a second energy dose to the gastrointestinal tissue, wherein applying the second energy dose to the gastrointestinal tissue decreases circulating insulin concentration.

2. The modulation system of claim 1, wherein application of the first energy dose to the first region of interest improves insulin sensitivity via a first molecular pathway.

3. The modulation system of claim 2, wherein application of the second energy dose to the second region of interest improves insulin sensitivity via a second molecular pathway.

4. The modulation system of claim 1, further comprising adjusting an activation time and/or duration of one or both of applying the first energy dose or the second energy dose.

5. The modulation system of claim 1, wherein applying the first energy dose to the liver or the sub-region of the liver and the second energy dose to the gastrointestinal tissue regulates a glucose concentration within a predefined range.

6. The modulation system of claim 1, wherein insulin sensitivity is mediated via one of a plurality of molecules of interest measured as a biomarker profile and wherein the biomarker profile characterizes expected concentrations or changes in concentration of the plurality of molecules of interest in response to applying the first energy dose to the liver or the sub-region of the liver and the second energy dose to the gastrointestinal tissue.

7. The modulation system of claim 6, wherein the plurality of molecules comprises two or more of glucose, insulin, glucagon, glucagon-like peptide 1, glucose transporter 2, norepinephrine, acetylcholine, protein kinase B, insulin receptor substrate 1, proopiomelanocortin or neuropeptide Y.

8. A method of changing insulin sensitivity of a subject, comprising:
applying a first ultrasound therapy beam to a liver or sub-region of the liver to stimulate a first insulin sensitivity regulating molecular pathway distal from the liver, wherein the first ultrasound therapy beam to the liver or the sub-region of the liver decreases circulating glucose concentration; and
applying a second ultrasound therapy beam to a gastrointestinal tissue to stimulate a second insulin sensitivity regulating molecular pathway, wherein the second ultrasound therapy beam to the gastrointestinal tissue decreases circulating insulin concentration.

9. The method of claim 8, wherein the first insulin sensitivity regulating molecular pathway and the second insulin sensitivity regulating molecular pathway work in opposition to one another.

10. The method of claim 8, comprising acquiring an input indicative of a profile of molecules of interest that comprises glucose and at least one additional molecule of interest.

11. The method of claim 10, wherein the at least one additional molecule of interest comprises one or more of insulin, glucagon, glucagon-like peptide 1, glucose transporter 2, norepinephrine, acetylcholine, protein kinase B, insulin receptor substrate 1, proopiomelanocortin, or neuropeptide Y.

12. The method of claim 8, wherein applying the first ultrasound therapy beam to the liver or the sub-region of the liver and the second ultrasound therapy beam to the gastrointestinal tissue regulates the circulating glucose concentration within a predefined range.

13. The method of claim 8, further comprising adjusting an activation time and/or duration of one or both of applying the first ultrasound therapy beam or the second ultrasound therapy beam based upon an input indicative of the circulating glucose concentration.

14. A modulation system comprising:

a non-invasive ultrasound probe, configured to emit one or more imaging beams and one or more therapy beams using the same or different transducers; and a controller configured to:

using an imaging mode of the non-invasive ultrasound probe, direct the non-invasive ultrasound probe toward a porta hepatis of a subject;

using a treatment mode of the non-invasive ultrasound probe, adjustably control the non-invasive ultrasound probe to apply a first therapy beam to the porta hepatis;

using the imaging mode of the non-invasive ultrasound probe or a different non-invasive ultrasound probe, direct the non-invasive ultrasound probe or the different non-invasive ultrasound probe toward a gastrointestinal tissue of the subject;

using the treatment mode of the non-invasive ultrasound probe or the different non-invasive ultrasound probe, adjustably control the non-invasive ultrasound probe or the different non-invasive ultrasound probe to apply a second therapy beam to the gastrointestinal tissue, wherein the second therapy beam to the gastrointestinal tissue decreases circulating insulin concentration; and receive an input indicative of at least a circulating glucose concentration.

\* \* \* \* \*